United States Patent
Heletjaris

(10) Patent No.: US 7,041,476 B2
(45) Date of Patent: May 9, 2006

(54) PLANT SUGAR TRANSPORT PROTEINS

(75) Inventor: Timothy G. Heletjaris, Ankeny, IA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 322 days.

(21) Appl. No.: 10/051,909

(22) Filed: Jan. 17, 2002

(65) Prior Publication Data

US 2002/0199217 A1   Dec. 26, 2002

(51) Int. Cl.
  *C12P 21/06*   (2006.01)
(52) U.S. Cl. .................. 435/69.1; 435/7.1; 435/6; 435/320.1; 435/325; 435/252.3; 536/23.1; 536/23.4; 536/23.6; 530/350
(58) Field of Classification Search ............... 435/69.1, 435/6, 7.1, 320.1, 419; 536/23.1, 23.4, 23.6; 530/350; 800/295; 514/44
  See application file for complete search history.

(56) References Cited

OTHER PUBLICATIONS

Kull et al., J. Genet. And Breed, vol. 49, No. 1, pp. 69-76, 1995.*
Kossmann et al., Progress in Biotechnology, vol. 10, pp. 271-278, 1995.*
National Center For Biotechnology Information General Identifier No. 3080420, Apr. 1, 1999, M. Bevan et al.
National Center For Biotechnology Information General Identifier No. 12039327, Aug. 28, 2001, C. R. Buell et al., Oryza Sativa Chromosome 10 Bac Osjnbb0064p21 Genomic Sequence.
National Center For Biotechnology Information General Identifier No. 1778093, Aug. 29, 1997, T. J. Chiou et al., Isolation And Molecular Characteristics Of Two Putative Sugar Transporters From Sugar Beet.
Tzyy-Jen Chiou et al., Plant Phys., vol. 113:663-665, 1997, Isolation And Molecular Characteristics Of Two Putative Sugar Transporters From Sugar Beet.
National Center For Biotechnology Information General Identifier No. 8347248, Jun. 8, 2000, A Weber et al., Identification, Purification, And Molecular Cloning Of A Putative Plastidic Glucose Translocator.
Andreas Weber et al., Plant Cell, vol. 12:787-801, 2000, Identification, Purification, And Molecular Cloning Of A Putative Plastidic Glucose Translocator.
National Center For Biotechnology Information General Identifier No. 5091611, Jun. 17, 1999, V. S. Vysotskaia et al, Oryza Sativa Chromosome 1 Bac 10a19i.

* cited by examiner

*Primary Examiner*—Kathleen M. Kerr
*Assistant Examiner*—Hope A. Robinson
(74) *Attorney, Agent, or Firm*—Morgan & Finnegan, L.L.P.

(57) ABSTRACT

This invention relates to an isolated nucleic acid fragment encoding a sugar transport protein, more specifically an *Arabidopsis*-like or *Beta-vulgaris*-like sugar transport protein. The invention also relates to the construction of a recombinant DNA construct encoding all or a portion of the sugar transport protein, in sense or antisense orientation, wherein expression of the recombinant DNA construct results in production of altered levels of the *Arabidopsis*-like or *Beta-vulgaris*-like sugar transport protein in a transformed host cell.

10 Claims, 11 Drawing Sheets

FIGURE 1A

```
SEQ ID NO:29   MSGAVLVAIAAAVGNLLQGWDNATIAGAVLYIKKEFNLESNPSVEGLIVAMSLIGATLIT
SEQ ID NO:2    MGGAVMVAIAASIGNLLQGWDNATIAGAVLYIKKEFNLQSEPLIEGLIVAMFLIGATVIT
SEQ ID NO:4    MAGAVLVAIAASIGNLLQGWDNATIAGAVLYIKKEFNLHSDPLIEGLIVAMSLIGATIIT
SEQ ID NO:6    ------------------------------------------------------------
SEQ ID NO:8    MKGAVLVAIAASIGNFLQGWDNATIAGANGYIKKDLALGTT--MERLVVGMSLIGATVIT
SEQ ID NO:10   ------------------------------------------------------------
SEQ ID NO:12   MSGAALVAIAASIGNLLQGWDNATIAGAVLYIKKEFQLENNPTVEGLIVA----------
SEQ ID NO:14   ------------------------------------------------------------
SEQ ID NO:16   ------------------------------------------------------------
SEQ ID NO:32   MSGAVLVAIVASIGNLLQGWDNATIAAAVLYIKKEFQNEPTVEGLIVSMSLIGATIVT
SEQ ID NO:37   MAGAVLVAIAASIGNLLQGWDNATIAGAVLYIKKEFNLQSEPLIEGLIVAMSLIGATIIT

SEQ ID NO:29   TCSGGVADWLGRRPMLILSSILYFVGSLVMLWSPNVYVLLLGRLLDGFGVGLVVTLVPIY
SEQ ID NO:2    TSPGPRADCVGRRPMLVASAVLYFVSGLVMLWAPIVYILLLARLIDGFGLAVTLVPLY
SEQ ID NO:4    TXS---------------------------------------------------------
SEQ ID NO:6    ------------------------------------------------------------
SEQ ID NO:8    TCSGPIADWLGRRPMMIISSVLYFLGGLVMLWSPNVYVLCLARLLDGFGIGLAVTLVPVY
SEQ ID NO:10   ------------------------------------------------------------
SEQ ID NO:12   ------------------------------------------------------------
SEQ ID NO:14   ------------------------------------------------------------
SEQ ID NO:16   ------------------------------------------------------------
SEQ ID NO:32   TFSGPLSDSIGRRPMLILSSILYFFSGLIMLWSPNVYVLLLARFVDGFGIGLAVTLVPLY
SEQ ID NO:37   TFSGAVADSFGRRPMLIASAVLYFVSGLVMLWAPNVYVLLLARLIDGFGIGLAVTLVPLY
```

FIGURE 1B

```
SEQ ID NO:29  ISETAP-PEIRGLLNTLPQFTG-SGGMFLSYCMVFGMSLMPSPSWRLMLGVLFIPSLVFF
SEQ ID NO:2   ISETAPHRXSWGXXNTLPQFIGVXGGMFLSYCMVFGMSLMPKPDWRLMLGVLSIPSLXYF
SEQ ID NO:4   ------------------------------------------------------------
SEQ ID NO:6   ------------------------------------------------------------
SEQ ID NO:8   ISETAP-SEIRGSLNTLPQFSG-SGGMFLSYCMVFGMSLSPAPSWRLMLGVLSIPSLLYF
SEQ ID NO:10  ------------------------------------------------------------
SEQ ID NO:12  ------------------------------------------------------------
SEQ ID NO:14  ---------SWK------------------------------------------------
SEQ ID NO:16  ------------------------------------------------------------
SEQ ID NO:32  ISEIAP-SEIRGLLNTLPQFSG-SGGMFLSYCMVFGMSLSPSPDWRIMLGVLAIPSLFFF
SEQ ID NO:37  ISETAP-TDIRGLLNTLPQFSG-SGGMFLSYCMVFGMSLMPQPDWRIMLGVLSIPSLIYF

SEQ ID NO:29  FLTVFFLPESPRWLVSKGRMLEAKRVLQRLRGREDVSGEMALLVEGLGLGIGGETTIEEYII
SEQ ID NO:2   GLTVFYLPESPRWLVSKGRMLEAKKVLQRLRGREDVSXEXALLVEGLGVGKDTRIXEYII
SEQ ID NO:4   ------------------------------------------------------------
SEQ ID NO:6   ------------------------------------------------------------
SEQ ID NO:8   ALTIFFLPESPRWLVSKGRMLEAKKVLQRLRGREDVSGEMALLVEGLGIGGDTSIEEYII
SEQ ID NO:10  ----DPSR----------------------------------------------------
SEQ ID NO:12  ------------------------------------------------------------
SEQ ID NO:14  ------------------------------------------------------------
SEQ ID NO:16  ------------------------------------------------------------
SEQ ID NO:32  GLTIFYLPESPRWLVSKGRMAEAKKVLQKLRGKDDVSGELSLLEGLEVGGDTSIEEYII
SEQ ID NO:37  ALTIFYLPESPRWLVSKGRMAEAKRVLQGLRGREDVSGEMALLVEGLGVGKDTKIEEYII
```

FIGURE 1C

```
SEQ ID NO:29    GPADEVTDDHDIAVDKDQIKLYGAEEGLSWVARPVKG----GSTMSVLSRHGSTMSRRQG
SEQ ID NO:2     GPATEAADDLVTDGDKEQITLYGPEEGQSWIARPSKGPIMLGSVLSLASRHGS-MVNQSV
SEQ ID NO:4     ------------------------------------------------------------
SEQ ID NO:6     ------------------------------------------------------------
SEQ ID NO:8     GPADDVADGHEHATEKDKIRLYGSQAGLSWLSKPVTGQ-----SSIGLASHHGS-IINQSM
SEQ ID NO:10    ------------EKDQIKLYGPEQGQSWVARPVAGP-----NSVGLVSRKGS-MANPS-
SEQ ID NO:12    ------------------------------------------------------------
SEQ ID NO:14    ------------------------------------------------------------
SEQ ID NO:16    GPATEAADDLVTDGDKEQITLYGPEEGQSWIARPSKGPIMLGSVLSLASRHGS-MVNQSV
SEQ ID NO:32    GPATEAADDLVTDGDKEQITLYGPEEGQSWVARPVHGQSALGSALGLISRHGS-MVSQGK
SEQ ID NO:37    GPDDELADEGLAP-DPEKIKLYGPEEGLSWVARPVHGQSALGSALGLISRHGS-MVSQGK

SEQ ID NO:29    SLIDPLVTLFGSVHEKMPDT----GSMRSALFPHFGSMFSVGGNQPRHEDWDEENLVGEGE
SEQ ID NO:2     PLMDPIVTLFGSVHENMPQAG---GSMRSTLFPNFGSMFSVTDQHAKNEQWDEENLHRDDE
SEQ ID NO:4     ------------------------------------------------------------
SEQ ID NO:6     ------------------------------------------------------------
SEQ ID NO:8     PLMDPLVTLFGSIHEKLPETGARGSMRSTLFPNFGSMFSTAEPHAKIEQWDEESLQRERE
SEQ ID NO:10    SLVDPLVTLFGSVHEKLPETG-------STLFPHFGSMFSVGGNQPRNEDWDEESLAREGD
SEQ ID NO:12    ------------------------------------------------------------
SEQ ID NO:14    ------------------------------------------------------------
SEQ ID NO:16    PLMDPIVTLFGSVHENMPQAG---GSMRSTLFPNFGSMFSVTDQHAKNEQWDEENLHRDDE
SEQ ID NO:32    PLVDPVVTLFGSVHEKMPEIM---GSMRSTLFPNFGSMFSVAEQQAKGDWDAES-QREGE
SEQ ID NO:37    PLVDPVVTLFGSVHEKMPEIM---GSMRSTLFPNFGSMFSVAEQQAKGDWDAES-QREGE
```

FIGURE 1D

```
SEQ ID NO:29   DYPSDH--GDDSEDDLHSPLISRQTTSME-KDMPHTAH--GTLSTERHGSQVQGAQGEGAG
SEQ ID NO:2    EYASDGAGGDYEDNLHSPLLSRQTTSLE-KDLPPPSHGSILGSMRRHSSIMQSSGEQGG
SEQ ID NO:4    ----------------------------------------------------------
SEQ ID NO:6    DYMSDATRGDSDDNLHSPLISRQTTSLE-KDLPPPSHGSILGSMRRHSSIMQSSGEQGG
SEQ ID NO:8    DYVSDA--GDSDDNLQSPLISRQTTSLD-KDIPPHAH--SNLASMRQGSLLHGNSGEPTG
SEQ ID NO:10   ----------------------------------------------------------
SEQ ID NO:12   --------------------------------------------------EGGEAVS
SEQ ID NO:14   ----------------------------------------------------------
SEQ ID NO:16   EYASDGAGGDYEDNLHSPLLSRQATGAEGKDIVHHGHRGSALS-MRRQTLL-GEGGDGVS
SEQ ID NO:32   DYGSDHGGDDIEDSLQSPLISRQATSVEGKEIA--APHGSIMGAVGRSSSL-MQGGEAVS
SEQ ID NO:37

SEQ ID NO:29   SMGIGGGWQVAWKWTEREDESGQKEEGF------PGSRRGSIVSLPGGDGT--GEA
SEQ ID NO:2    STDIGGGWQLAWKWSEKEGENGRKEGGFKRVYLHQEGVPGSRRGSIVSLPGGDVLEG-S
SEQ ID NO:4    ----------------------------------------------------------
SEQ ID NO:6    STGIGGGWQLAWKWTDK-GEDGKQQGGFKRIYLHEEGVSASRRGSIVSIPGEG------
SEQ ID NO:8    STGIGGGWQLAWKWSEREGPDGKKEGGFKRIYLHQDGGSSGSRRGSVVSLPGGD--LPTDS
SEQ ID NO:10   ------------------------VLTL------------------------------
SEQ ID NO:12   STGIGGGWQLAWKWSERQGEDGKKEGGFKRIYLHQEGVADSRRGSVVSLPGGDATQGGS
SEQ ID NO:14   ----------------------------------------------------------
SEQ ID NO:16   STDIGGGWQLAWKWSEKEGENGRKEGGFKRVYLHQEGVPGSRRGSIVSLPGGDVFEG-S
SEQ ID NO:32   SMGIGGGWQLAWKWTEREGADGEKEGGFQRIYLHEEGVTGDRRGSILSLPGGD--VPPGG
SEQ ID NO:37   
```

FIGURE 1E

```
SEQ ID NO:29   DFVQASALVSQPALYSKDLLKEH-TIGPAMVHPSETT-KGSIWHDLHDPGVKRALVVGVG
SEQ ID NO:2    EFVHAAALVSQSALFSKGLAEPRMS-DAAMVHPSEVAAKGSRWKDLFEPGVRRALLVGVG
SEQ ID NO:4    ------------------------------------------------------------
SEQ ID NO:6    EFVQAAALVSQPALYSKELIDGH-PVGPAMVHPSETASKGPSWKALLEPGVKHALVVGVG
SEQ ID NO:8    EVVQAAALVSQPALYNEDLMRQR-PVGPAMIHPSETIAKGPSWSDLFEPGVKHALIVGVG
SEQ ID NO:10   ------------------------------------------------------------
SEQ ID NO:12   GFIHAAALVSHSALYSKDLMEERMAAGPAMIHPLEAAPKGSIWKDLFEPGVRRALFVGVG
SEQ ID NO:14   ----------------------------------------EPGVKHALFVGIG
SEQ ID NO:16   EFVHAAALVSQSALFSKGLAEPRMS-DAAMVHPSEVAAKGSRWKDLFEPGVRRALLVGVG
SEQ ID NO:32   ------------------------------------------------------------
SEQ ID NO:37   EFVQAAALVSQPALYSKELMEQRLA-GPAMVHPSQAVAKGPKWADLFEPGVKHALFVGIG

SEQ ID NO:29   LQILQQFSGINGVLYYTPQILEQAGVGILLSNMGISSSSASLLISALTTFVMLPAIAVAM
SEQ ID NO:2    IQILQQFAGINGVLYYTPQILEQAGVAVILSKFGLSSASASILISSLTTLLMLPCIGFAM
SEQ ID NO:4    ------------------------------------------------------------
SEQ ID NO:6    IQILQQFSGINGVLYYTPQILEEAGVEVLLSDIGIGSESASFLISAFTTFLMLPCIGVAM
SEQ ID NO:8    IQILQQFAGINGVGYLLSSLGLGSTSSSFLISAVTTLLMLPCIAIAM
SEQ ID NO:10   ------------------------------------------------------------
SEQ ID NO:12   MQILQQFSGINGVLYYTPQILEQAGVAVLLSNLGLSSASASILISSLTTLLMLPSIGVAM
SEQ ID NO:14   IQMLQQFAGINGVLYYTPQILEQAGVAVLLSNLGLSSASASILISSLTTLLMLPSIGVAM
SEQ ID NO:16   LQILQQFAGINGVLYYTPQILEQAGVGVLLSNIGLSSSSASILISALTTLLMLPSIGIAM
SEQ ID NO:32   IQILQQFAGINGVLYYTPQILEQAGVAVILSKFGLSSASASILISSLTTLLMLPCIGFAM
SEQ ID NO:37   IQILQQFAGINGVLLANIGLSSSSASILISGLTTLLMLPSIGIAM
```

FIGURE 1F

```
SEQ ID NO:29   RLMDLSGRRTLLLTTIPILIASLLVLVISNLVHMNSIVHAVLSTVSVVLYFCFFVMGFGP
SEQ ID NO:2    LLMDLSGRRFLLLGTIPILIASLVILVVSNLIDLGTLAHALLSTISVIVYFCCFVMGFGP
SEQ ID NO:4    ------------------------------------------------------------
SEQ ID NO:6    ------------ILVNILDVGTMVHASLSTVSVILYFCFFVMGFGP
SEQ ID NO:8    KLMDVSGRRQLLLTTIPVLIVSLILIVIGSLVNFGNVAHAAISTVCVVVYFCCFVMGYGP
SEQ ID NO:10   RLMDISGRRTLLLSTIPVLIAALLILVLGSLVDLGSTANASISTISVIVYFCFFVMGFGP
SEQ ID NO:12   ------------------------------------------------------------
SEQ ID NO:14   RLMDISGRRFLLLGTIPILIASLIVLGVVNVINLSTVPHAVLSTVSVIVYFCCFVMGFGP
SEQ ID NO:16   RLMDMSGRRFFLLSTIPVLIVALAVLVLVNVLDVGTMVHAALSTISVIVYFCFFVMGFGP
SEQ ID NO:32   LLMDLSGRRFLLLGTIPILIASLVIIVVSNLIDLGTLAHALLSTVSVIVYFCCFVMGFGP
SEQ ID NO:37   RLMDMSGRRFLLLATIPILIVALALILVNILDVGTMVHASLSTVSVILYFCFFVMGFGP

SEQ ID NO:29   APNILCSEIFPTRVRGICIAICALTFWICDIIVTYSLPVLLKSIGLAGVFGMYAIVCCIS
SEQ ID NO:2    IPNILCAEIFPTRVRGLCIAICAFTFWIGDIIVTYSLPVMLNAIGLAGVFSIYAVVCLIS
SEQ ID NO:4    ------------------------------------------------------------
SEQ ID NO:6    IPNILCAEIFPTTVRGICIAICALTFWIGDIIVTYTLPVMLNAIGLAGVEGIYAVVCFIS
SEQ ID NO:8    IPNILCSEIFPTRVRGLCIAICALVFWIGDIIITYSLPVMLGSLGLGGVFAIYAVVCFIS
SEQ ID NO:10   IPNILCAEIFPTRVRGLCIAICALCFWICDIIVTYTLPVMLPVMLNSVGLAGVFGIYAVVCFIA
SEQ ID NO:12   ------------------------------------------------------------
SEQ ID NO:14   IPNILCAEIFPTRVRGVCIAICALTFWICDIIVTYSLPVMLNAIGLAGVFGIYAVVCCIA
SEQ ID NO:16   IPNILCAEIFPTSVRGICIAICALTFWIGDIIVTYTLPVMLNAIGLAGVFGIYAIVCVLA
SEQ ID NO:32   IPNILCAEIFPTRVRGLCIAICAETFWIGDIIVTYSLPVMLNAIGLAGVFSIYAVVCLIS
SEQ ID NO:37   IPNILCAEIFPTTVRGICIAICALTFWIGDIIVTYTLPVMLNAIGLAGVFGIYAVVCILA
```

FIGURE 1G

```
SEQ ID NO:29    WVFVFEIKVPETKGMPLEVITEFFSVGARQAEAAKNE
SEQ ID NO:2     FVFVELKVPETKGMPLEVITEFFAVGAKQ-AAAK-A
SEQ ID NO:4     ------------------------------------
SEQ ID NO:6     FLEVFMKVPETKGMPLEVITEFFSVGAKQ-AKE---D
SEQ ID NO:8     WIFVFELKVPETKGMPLEVISEFFSVGAKQAASAKNE
SEQ ID NO:10    WVFVFELKVPETKGMPLEVIIEFFSVGAKQEDDAKHN
SEQ ID NO:12    ------------------------------------
SEQ ID NO:14    FVFVYLKVPETKGMPLEVITEFFAVGAKQ-AQATIA
SEQ ID NO:16    FVFVYMKVPETKGMPLEVITEFFSVGAKQ-GKEATD
SEQ ID NO:32    FVFVELKVPETKGMPLEVITEFFAVGAKQ-AAAK-A
SEQ ID NO:37    FLEVFMKVPETKGMPLEVITEFFSVGAKQ-AKE---D
```

FIGURE 2A

```
SEQ ID NO:30   MSE------------------------------GTNKAMSDPPPTASKVIAD-----------
SEQ ID NO:18   SR--------------------------------------AQSEPSTMASAP-----------
SEQ ID NO:20   M-------------------------------------------------ASDE---------
SEQ ID NO:22   ---------------------------------------------------------------
SEQ ID NO:24   MTE-----------------------------------------MASAA--------------
SEQ ID NO:26   ------------------------------------GK--LVEA--AEAHKTLQD--------
SEQ ID NO:28   MKM-----------------------------------------MDRAA--------------
SEQ ID NO:38   M---------------------------------SPERKGAEDKEEGSRMASAA---------
SEQ ID NO:36   M-----------------------------SFRGE-------------------ESGGEDG------GRTASASDLRKPFL
               -----------------------------GGG---SNRGG---------------AGAGEES------G-SDHDGVLRRPLL

SEQ ID NO:30   --------------F-DPLKKPPK------RN----K------FAFACATLASMTSVLLGYDIG
SEQ ID NO:18   --------------L--PAAIEPG------KKGNVK-------FAFACXILASMTSILLGYDIG
SEQ ID NO:20   --------------LAK--AVEPR------KKGNVK-------YASICAILASMASVILGYDIG
SEQ ID NO:22   --------------L--PEAVAPK------KKGNVR-------FAFACAILASMTSILLGYDIG
SEQ ID NO:24   --------------F-DPPKKKR-K-----RN----K------YAFACAMLASMTSILLGYDIG
SEQ ID NO:26   --------------L--PAAVEPK------KKGNVR-------FAFACAILASMTSILLGYDIG
SEQ ID NO:28   --------------LPEPGAVHPR------NKGNFK-------YAFTCALCASMATIVLGYDVG
SEQ ID NO:38   HT--GSWYKMSSAGGGGMGSRLGSSAYSLRDSSVSAVLCTL------IVALGPIQFGFTCG
SEQ ID NO:36   NT--GSWYRMSSRQSSFAPGT---SSMAVLRESHVSAFLCTL------IVALGPIQFGFTSG

SEQ ID NO:30   VMSGAIIYLKEDWHISDTQI-----GVLVGILNIYCLFGSFAAGRTSDWIGRRYTIVLAGA
SEQ ID NO:18   VMSGASLYIKKDLKISDVKL-----EILMGILNVYSLIGSXAAGRTSDWIGRRXTIVFAAV
SEQ ID NO:20   VMSGAAMYIKKDLNITDVQL-----EILIGILSLYSLFGSFAGARTSDRIGRRLTVVFAAV
SEQ ID NO:22   VMSGASLYIKKDFNISDGKV-----EVLMGILNLYSLIGSFAAGRTSDWIGRRYTIVFAAV
SEQ ID NO:24   VMSGAAIYIKRDLKVSDEQI-----EILLGIINLYSLIGSCLAGRTSDWIGPRYTIVFAGT
SEQ ID NO:26   VMSGASLYIQKDLKINDTQL-----EVLMGILNVYSLIGSFAAGRTSDWIGRRFTIVFAAV
SEQ ID NO:28   VMSGASLYIKRDLQITDVQL-----EIMMGILSVVALIGSFLGARTSDWVGRRVTVVFAAA
SEQ ID NO:38   FSSPTQDAIISDLGLT-----LSEFSLFGSLSNVGAMVGAIASGQIAEYIGRKGSLMIAAI
SEQ ID NO:36   FSSPTQDAMVRDLNLS------ISEFSAFGSLSNVGGMVGAIASGQMAEYIGRKGSLMIAAI
```

FIGURE 2B

```
SEQ ID NO:30    IFFVGALLMGFATNYAFLMVGRFVTGIGVGYALMIAPVYTAEVSPASSRGFLTSFPEVFI
SEQ ID NO:18    IFFAGAXIMGFAVNYWMLMFGRFVAGIGVGYALMIATVYTAEVSPXSARGFLTSFPEVFI
SEQ ID NO:20    IFFVGSLLMGFAVNYGMLMAGRFVAGVGVGYGGMIAPVYTAEISPAASRGFLTTFPEVFI
SEQ ID NO:22    IFFAGXFLMGFAVNYAMLMFGRFVAGIGVGYALMIAPVYTAEVSPASARGFLTSFPEVFI
SEQ ID NO:24    IFFVGALLMGFSPNYSFLMFGRFVAGIGIGYALMIAPVYTAEVSPASSRGFLTSFPEVFI
SEQ ID NO:26    IFFAGALIMGFSVNYAMLMFGRFVAGIGVGYALMIAPVNTGEVSPASARGVLTSFPEVFI
SEQ ID NO:28    IFNNGSLLMGFAVNYAMLMVGRFVTGIGVGYAIMVAPVYTPEVSPASARGFLTSFTEVFI
SEQ ID NO:38    PNIIGWLAISFAKDSSFLFMGRLLEGFGVGVISYVVPVYIAEIAPQTMRGALGSVNQLSV
SEQ ID NO:36    PNIIGWLAISFAKDASFLYMGRLLEGFGVGIISYTVPVYIAEISPQNMRGALGSVNQLSV

SEQ ID NO:30    NAGILLGYISNLAFSSLPTHLSWRFMLGIGAIPSIFLAIGVLAMPESPRWLVMQGRLGDA
SEQ ID NO:18    ------------------------------------------------------------
SEQ ID NO:20    NIGILLGYLSNFAFARLPLHLGWRVMLAIGAVPSGLLALLVFCMPESPRWLVLKGRLADA
SEQ ID NO:22    NFGILLGYVSNYAFSRLPLNLGWRIMLGIGAAPSVLLALMVLGMPESPRWLVMKGRLADA
SEQ ID NO:24    NGGILIGYISNYAFSKLTLKVGWRMMLGVGAIPSVLLTVGVLAFMVLGMPESPRWLVMRGRLGEA
SEQ ID NO:26    NEGILLGYVSNFAFARLSRLGWRIMLGIGAVPSVLLAFMVLGMPESPRWLVMKGRLADA
SEQ ID NO:28    NVGILLGYVSNYAFARLPLHLSWRVMLGIGAVPSALLALMVFGMPESPRWLVMKGRLADA
SEQ ID NO:38    TIGILLAYLLGMFVP--------WRILSVLGILPCSILIPGLFFIPESPRWLAKMGKMEDF
SEQ ID NO:36    TFGIFLAYLLGMFIP--------WRLLAVIGALPCTMLIPGLFFIPESPRWLAKMNLTEDC

SEQ ID NO:30    KKVLNRISDSPEEAQLRLSEIKQTAGIPAECDEDIYKVEKTKIKSGNA-VWKELFFNPTP
SEQ ID NO:18    ------------------------------------------------------------
SEQ ID NO:20    RAVLEKTSATPEEAAERLADIKAAAGIPKGLDGDVVTVPGKEQGGELQVWKKLILSPTP
SEQ ID NO:22    KVVLEKTSDTAEEAAERLADIKAAAGIPEELDGDVVTVPK-RGSGNEKRVWKELILSPTP
SEQ ID NO:24    RKVLNKTSDSKEEAQLRLAEIKQAAGIPESCNDDVVQVNKQS--NGEG-VWKELFLYPTP
SEQ ID NO:26    KVVLAKTSDTPEEAAERIADIKTAAGIPLGLDGDVVPVPKNKGSSEEKRVLKDLILSPTI
SEQ ID NO:28    RAVLAKTSDTPEEAVERLDQIKAAAGIPRELDGDVVVMP-KTKGGQEKQVWKELIFSPTP
SEQ ID NO:38    ESSLQ--------VLRGFETDIAVEVN-EIKRSV-----QSSRRTTIRFADIK----QK
SEQ ID NO:36    ETSLQ--------VLRGFETDITTEVN-DIKRAV-----ASSSKRTTISFQELN----QK
```

FIGURE 2C

| | | |
|---|---|---|
| SEQ ID NO:30 | AVRRAVIAGIGIHFFQQASGIDAVVLYSPRIFQSAGITNARKQLLATVAVGVVKTLFILV |
| SEQ ID NO:18 | -------------------------------------------------------- |
| SEQ ID NO:20 | AVRRILLSAVGLHFFQQASGSDSVVQYSARLFKSAGITDDNKLLGVTCAVGVTKFFILV |
| SEQ ID NO:22 | AMRRILLSGIGIHFFQHALGIHSVVFYSPLVFKSPGLTNDKHFLGTTWPFGVTKRLFLL |
| SEQ ID NO:24 | AIRHIVIAALGIHFFQQASGVDAVVLYSPRIFEKAGITNDTHKLLATVAVGFVKTVFILA |
| SEQ ID NO:26 | AMRHILIAGIGIHFFQQSSGIDAVVLYSPLVFKSACITGDSRLRGTTVAVGATNTVFLV |
| SEQ ID NO:28 | AMRRILLAALGIHFFQQATGSDSVVLYSPRVFQSAGITGDNHLLGATCAMGVMKTLFILV |
| SEQ ID NO:38 | RYSVPLMVGIGLLVLQQLSGVNGILFYAASIFKAAGLTNSN---LATFGLGVVQVVATGV |
| SEQ ID NO:36 | KYRTPLLLGIGLLVLQNLSGINGVLFYASSIFKAAGVTNSD---LATCSLGAIQVLATGV |

| | | |
|---|---|---|
| SEQ ID NO:30 | ATFQLDKYGRRPLLLTSVGGMIIAILTLAMSLTVID-HSHHKITWAI--ALCITMVCAVV |
| SEQ ID NO:18 | -------------------------------------------------------- |
| SEQ ID NO:20 | ATFLLDRAGRRPLLLISTGGMIVSLICLGSGLTVAGHHPDTKVAWAV--ALCIASTLSYI |
| SEQ ID NO:22 | ATFFIDGVGRRPLLLGSTGGIILSLIGLGAGLTVVGQHPDAKIPWAI--GLSIASTLAYV |
| SEQ ID NO:24 | ATFTLDRVGRRPLLLTSTGGMVLSLLTLAISLTVID-HSERKLMWAV--GSSIAMVLAYV |
| SEQ ID NO:26 | ATFLLDRIRRRPLVLTSTGGMLVSIVGLATGLTVISRHPDEKITWAI--VLCIFCIMAYV |
| SEQ ID NO:28 | ATFQLDRVGRRPLLLTSTAGMLACIIGLGTGLTVVGRHPDAKVPWAI--GLCIVSILAYV |
| SEQ ID NO:38 | TTWLTDKAGRRLLL1ISTTGMTITLVVVSVSFFVKDNITNGSHLYSVMSMLSLVGLVAFV |
| SEQ ID NO:36 | TTWLLDRAGRRILLIISTSGMTLCLLAVSVVFFLKDNISQDSNSYYILTMISLVGIVSFV |

| | | |
|---|---|---|
| SEQ ID NO:30 | ASFSIGLGPITWVYSSEVFPLRLRAQGTSMGVAVNRVVSGVISIFFLPLSHKITTGGAFF |
| SEQ ID NO:18 | -------------------------------------------------------- |
| SEQ ID NO:20 | AFFSIGLGPITWVYSSEIFPLQVRALGFAVGVASNRVTSAVISMTFLSLSKAITIGGSFF |
| SEQ ID NO:22 | AFFSIGLGPITWVYSSEIFPLQVRALGCSLGVAANRVTSGVISMTFLSLSKAITIGGSFF |
| SEQ ID NO:24 | ATFSIGAGPITWVYSSEIFPLRLRAQGAAAGVAVNRTTSAVVSMTFLSLTRAITIGGAFF |
| SEQ ID NO:26 | AFFSIGLGPITWVYSSEIFPLHVRALGCSLGVAVNRLTSGVISMTFISLSKAMTIGGAFF |
| SEQ ID NO:28 | SFFSIGLGPLTSVYTSEVFPLRVRALGFALGTSCNRVTSAAVSMSFLSLSKAITIGGSFF |
| SEQ ID NO:38 | ISFSLGLGAIPWIIMSEILPVNIKSLAGSVATLANWLTAWLITMT-ASLMLSWSNGGTFA |
| SEQ ID NO:36 | ITFSFGMGAIPWLMMSEILPVSIKSLGGSIATLANWLTSFAITMT-TNLMLTWSVGGTFL |

FIGURE 2D

```
SEQ ID NO:30   LFGGIAIIAWFFFLTFLPETRGR-TLENMHELFEDFRWRESFPGNKSNNDENSTRKQSNG
SEQ ID NO:18   ------------------------------------------------------------
SEQ ID NO:20   LYSGIAAVAWVFFFTCLPETRGR-TLEEMGKLFGM--------------PDTGMAEEAED
SEQ ID NO:22   LYSGIAALAWVFFYTYLPETRGR-TLEEMSKLFGD---------------TAAASESDEPA
SEQ ID NO:24   LYCGIATVGWIFFYTVLPETRGK-TLEDMEGSFGTFRSKSN--ASKAVENENG-------
SEQ ID NO:26   LFAGIASFAWVFFFAYLPETRGR-TLEDMSSLFGN---------------TATHKQGAAEA
SEQ ID NO:28   LYAGIAAIGWIFFFTFIPETRGL-PLEEIGKLFGM---------------TDTAVEAQDTA
SEQ ID NO:38   IYAAVCAGTLVFVCLWVPETKGR-TLEEI---AF--------------------------
SEQ ID NO:36   SYMVVSAFTIVFVVLWVPETKGXNSRGDT--IFVSLSIQRQLQ-----------------

SEQ ID NO:30   NDKSQVQLGETTTSTTVTNDNH
SEQ ID NO:18   ------------TS--------
SEQ ID NO:20   A-AAKEKVVELPSSK-------
SEQ ID NO:22   KEK---KKVEMAATN-------
SEQ ID NO:24   -QVAQVQLG-------TNVQT
SEQ ID NO:26   DDDAGEKKVEMAATN-------
SEQ ID NO:28   T-KDKAKVGEM----N------
SEQ ID NO:38   ---------------SFR----
SEQ ID NO:36   ----------------WLPECLS
```

PLANT SUGAR TRANSPORT PROTEINS

FIELD OF THE INVENTION

This invention is in the field of plant molecular biology. More specifically, this invention pertains to nucleic acid fragments encoding sugar transport proteins in plants and seeds.

BACKGROUND OF THE INVENTION

Sugar is one form of carbohydrate produced in photosynthesizing cells in most higher plants and is the main form of transported carbon in most annual field crops such as corn, rice, soybeans and wheat. As such its movement and concentration across various plant membranes is critical to plant growth and development. In addition sugar is the main form of carbon that moves into developing seeds of soybeans, rice, corn and wheat. This movement and concentration is accomplished by the action of carrier proteins that act to transport sugar against a concentration gradient often by coupling sugar movement to the opposite vectoral movement of a proton. Specific sugar carrier proteins from these crop plants could be manipulated in efforts to control carbon flux and the timing and extent of sugar transport phenomena (e.g., grain fill duration) that are important factors in crop yield and quality. Accordingly, the availability of nucleic acid sequences encoding all or a portion of sugar transport proteins would facilitate studies to better understand carbon flux and sugar transport in plants, provide genetic tools for the manipulation of sugar transport, and provide a means to control carbohydrate transport and distribution in plant cells.

All patents, patent publications, and documents noted herein are hereby incorporated by reference in their entirety.

SUMMARY OF THE INVENTION

In a first embodiment, the present invention concerns isolated polynucleotides comprising a nucleotide sequence encoding a polypeptide having sugar transport protein activity wherein the amino acid sequence of the polypeptide and the amino acid sequence of SEQ ID NO:32 or 36 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence. More specifically, the present invention concerns isolated polynucleotides encoding the polypeptide sequence of SEQ ID NO:32 or 36 or nucleotide sequences comprising the nucleotide sequence of SEQ ID NO:31 or 35.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a fifth embodiment, the present invention concerns a method for producing a transgenic plant comprising transforming a plant cell with any of the isolated polynucleotides of the present invention and regenerating a plant from the transformed plant cell. The invention also concerns the transgenic plant produced by this method, and the seed obtained from this transgenic plant.

In a sixth embodiment, the invention concerns a method for isolating a polypeptide encoded by the polynucleotide of the present invention comprising isolating the polypeptide from a cell containing a recombinant DNA construct comprising the polynucleotide operably linked to a regulatory sequence.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A, 1B, 1C, 1D, 1E, 1F and 1G show a comparison of the amino acid sequences set forth in SEQ ID NOs:2, 4, 6, 8, 10, 12, 14, 16, and 32 with the *Arabidopsis thaliana*-like sugar transport protein amino acid sequence set forth in SEQ ID NOs:29 and 37. Amino acid designations in small case letters represent regions that are thought to be *Arabidopsis thaliana*-like sugar transport protein signatures.

FIGS. 2A, 2B, 2C and 2D show a comparison of the amino acid sequences set forth in SEQ ID NOs:18, 20, 22, 24, 26, 28, and 36 with the *Beta vulgaris*-like sugar transport protein amino acid sequence set forth in SEQ ID NO:30 and 38.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Plant Sugar Transport Proteins

| Sugar Transport Protein | Clone Designation | SEQ ID NO: (Nucleotide) | SEQ ID NO: (Amino Acid) |
|---|---|---|---|
| *Arabidopsis*-like | contig of: cil1c.pk001.f21 cr1n.pk0143.h10:fis p0002.cgevb73r p0032.crcba66r p0072.comgi92r p0097.cqran41r p0106.cjlpm67r p0114.cimml81r p0128.cpict38r | 1 | 2 |
| *Arabidopsis*-like | contig of: rds1c.pk007.n17 rlr12.pk0013.d11 | 3 | 4 |
| *Arabidopsis*-like | rls6.pk0003.d5:fis | 5 | 6 |
| *Arabidopsis*-like | contig of: sdp3c.pk012.i1 sfl1.pk0079.a4 sgs4c.pk005.c9 | 7 | 8 |
| *Arabidopsis*-like | ssl.pk0022.f1 | 9 | 10 |
| *Arabidopsis*-like | wlk8.pk0001.a12 | 11 | 12 |
| *Arabidopsis*-like | contig of: wlm96.pk043.e19 wre1n.pk0062.g6 | 13 | 14 |

TABLE 1-continued

Plant Sugar Transport Proteins

| Sugar Transport Protein | Clone Designation | SEQ ID NO: (Nucleotide) | SEQ ID NO: (Amino Acid) |
|---|---|---|---|
| Arabidopsis-like | wre1n.pk0006.b4 | 15 | 16 |
| Arabidopsis-like | p0110.cgsmx44r | 31 | 32 |
| Beta vulgaris-like | cc1.mn0002.h1 | 17 | 18 |
| Beta vulgaris-like | cepe7.pk0018.g3 | 19 | 20 |
| Beta vulgaris-like | contig of:<br>rl0n.pk102.p24<br>rl0n.pk107.p2<br>rlr6.pk0005.b10 | 21 | 22 |
| Beta vulgaris-like | contig of:<br>sfl1.pk0058.h12<br>sgs2c.pk004.o17<br>sr1.pk0061.g8<br>sre.pk0032.h6 | 23 | 24 |
| Beta vulgaris-like | wlk8.pk0001.a11 | 25 | 26 |
| Beta vulgaris-like | wlm1.pk0012.h1 | 27 | 28 |
| Beta vulgaris-like | p0127.cntak13r | 33 | 34 |
| Beta vulgaris-like | p0127.cntas61r | 35 | 36 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single-or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:31 or 35, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to a regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NO:31 or 35, and the complement of such nucleotide sequences may be used to affect the expression and/or function of a sugar transport protein in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein.

Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNAS-TAR Inc., Madison, Wis). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to at least one regulatory sequence in a sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) Nature (London) 327:70–73; U.S. Pat. No. 4,945,050), or an Agrobacterium-mediated method using an appropriate Ti plasmid containing the transgene (Ishida Y. et al., 1996, Nature Biotech. 14:745–750). The term "transformation" as used herein refers to both stable transformation and transient transformation.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence encoding a sugar transport protein polypeptide having at least 75%, 80%, 82%, 85%, 90%, 92%, 95%, 98% or 100% identity, based on the Clustal method of alignment, when compared to a polypeptide of SEQ ID NO:32 or 36. It is well understood by one skilled in the art that many levels of sequence identity are useful in identifying related polypeptide sequences. Thus, any integer percentage from 75% to 100% is also within the scope of this invention.

This invention also relates to the isolated complement of such polynucleotides. In a more preferred embodiment, the complement and the polynucleotide comprise essentially the same number of nucleotides, and the nucleotide sequences of the complement and the polynucleotide have 100% complementarity.

Nucleic acid fragments encoding at least a portion of several sugar transport proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sugar transport protein, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NO:31 or 35 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein.

Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of sugars in those cells. This can lead to changes in metabolism and alterations in starch levels in plant tissues.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide (or recombinant DNA construct) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a sugar transport protein polypeptide having an amino acid sequence that is at least 75%, 80%, 82%, 85%, 87%, 90%, 92% 95%, 97% or 100% identical, based on the Clustal method of alignment, to a polypeptide of SEQ ID NO:32 or 36.

The instant polypeptides (or portions thereof may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded sugar transport proteins. An example of a vector for high level expression of the instant polypeptides in a bacterial host is provided (Example 7).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean, or wheat tissues were prepared. The characteristics of the libraries are described below.

TABLE 2 cDNA Libraries from Corn, Rice, Soybean, and Rice

| Library | Tissue | Clone |
|---|---|---|
| cil1c | Corn (*Zea mays* L., EB90) pooled immature leaf tissue at V4, V6 and V8. | cil1c.pk001.f21 |
| p0110 | SA infiltrated V3/V4 leaf tissue (*minus midrib*), screened 1 pool of A63 + SA 4 h; A63 + SA 24 hr; and A63 + SA 7 days | p0110.cgsmx44r |
| rlr12 | Rice Leaf 15 Days After Germination, 12 Hours After Infection of Strain *Magnaporthe grisea* 4360-R-62 (AVR2-YAMO); Resistant | rlr12.pk0013.d11 |
| rls6 | Rice Leaf 15 Days After Germination, 6 Hours After Infection of Strain *Magnaporthe grisea* 4360-R-67 (AVR2-YAMO); Susceptible | rls6.pk0003.d5:fis |
| sgs4c | Soybean (*Glycine max* L.) seeds 2 days after germination. | sgs4c.pk005.c9 |
| ssl | Soybean Seedling 5–10 Days After Germination | ssl.pk0022.fl |
| wlk8 | Wheat Seedlings 8 Hours After Treatment With KQ926** | wlk8.pk0001.a12 |
| wlm96 | Wheat Seedlings 96 Hours After Inoculation With *Erysiphe graminis* f. sp tritici | wlm96.pk043.e19 |
| wre1n | Wheat Root From 7 Day Old Etiolated Seedling* | wre1n.pk0006.b4 |
| cc1 | Corn Undifferentiated Callus | cc1.mn0002.h1 |
| cepe7 | Corn 7 Day Old Epicotyl From Etiolated Seedling | cepe7.pk0018.g3 |
| p0127 | Nucellus tissue, 5 days after silking, screened 1 | p0127.cntak13r |
| p0127 | Nucellus tissue, 5 days after silking, screened 1 | p0127.cntas61r |
| rl0n | Rice 15 Day Old Leaf* | rl0n.pk102.p24 |
| sr1 | Soybean Root | sr1.pk0061.g8 |
| wlk8 | Wheat Seedlings 8 Hours After Treatment With KQ926** | wlk8.pk0001.a11 |
| wlm1 | Wheat Seedlings 1 Hour After Inoculation With *Erysiphe graminis* f. sp tritici | wlm1.pk0012.h1 |

*These libraries were normalized essentially as described in U.S. Pat. No. 5,482,845, incorporated herein by reference.
**KQ926: Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding sugar transport proteins were identified by conducting BLAST (Basic Local Alignment Search Tool; Altschul et al. (1993) *J. Mol. Biol.* 215: 403–410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "plog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Arabidopsis-like Sugar Transport Proteins The BLASTX search using the EST sequences from clones listed in Table 3 revealed similarity of the polypeptides encoded by the cDNAs to Arabidopsis-like sugar transport proteins from Arabidopsis thaliana (NCBI General Identifier No. gi 3080420, SEQ ID NO:29). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Arabidopsis-like Sugar Transport Proteins

| Clone | Status | BLAST pLog Score [NCBI Identifier No. gi 3080420] |
|---|---|---|
| contig of:<br>cil1c.pk001.f21<br>crln.pk0143.h10:fis<br>p0002.cgevb73r<br>p0032.crcba66r<br>p0072.comgi92r<br>p0097.cqran41r<br>p0106.cjlpm67r<br>p0114.cimml81r<br>p0128.cpict38r | Contig | >250.0 |
| contig of:<br>rds1c.pk007.n17<br>rlr12.pk0013.d11 | Contig | 27.70 |
| rls6.pk0003.d5:fis | FIS | 54.00 |
| contig of:<br>sdp3c.pk012.i1<br>sfl1.pk0079.a4<br>sgs4c.pk005.c9 | Contig | >250.00 |
| ssl.pk0022.f1 | EST | >250.00 |
| wlk8.pk0001.a12 | EST | 21.30 |
| contig of:<br>wlm96.pk043.e19<br>wre1n.pk0062.g6 | Contig | 149.00 |
| wre1n.pk0006.b4 | EST | 117.00 |

The sequence of the entire cDNA insert in the clones listed in Table 3 was determined. Further sequencing and searching of the DuPont proprietary database allowed the identification of another corn clone encoding an Arabidopsis-like sugar transport protein. The BLASTX search using the EST sequences from clones listed in Table 3 revealed similarity of the polypeptides encoded by the cDNAs to Arabidopsis-like sugar transport proteins from rice (Oryza sativa) (NCBI General Identifier No. gi 12039327, SEQ ID NO:37). Shown in Table 4 are the BLAST results for individual ESTs ("EST"), sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences derived from an FIS, a contig, or an FIS and PCR and encoding the entire protein ("CGS"):

TABLE 4

BLAST Results for Sequences Encoding a Polypeptides Homologous to an Arabidopsis-like Sugar Transport Protein

| Clone | Status | BLAST pLog Score NCBI Identifier No. gi 12039327 |
|---|---|---|
| p0110.cgsmx44r | FIS | >180.00 |

FIGS. 1A, 1B, 1C, 1D, 1E, 1F and 1G present an alignment of the amino acid sequences set forth in SEQ ID NOs: 2, 4, 6, 8, 10, 12, 14, 16, and 32, and the Arabidopsis and rice sequences (SEQ ID NOs:29 and 37). The data in Table 5 represents a calculation of the percent identity of the amino acid sequences set forth in SEQ ID NOs:2, 4, 6, 8, 10, 12, 14, 16, and 32, and the Arabidopsis and rice sequences (SEQ ID NOs:29 and 37). The BLAST pLog score for the corn sequence is the highest possible under the new BLAST format (i.e. >180.00), under the previous search (Table 3) this score would have been >250.00.

The sequence alignments disclose several conserved sequence elements distributed throughout the polypeptide sequences. For instance, some conserved elements include, but are not limited to: DGFGXGLXVTLVPXYISE (SEQ ID NO:45), NTLPQFXGXXGGMFLSYCMVFGMSL (SEQ ID NO:46), MLGVLXIPSL (SEQ ID NO:47), RWLVSKGRMXEAK (SEQ ID NO:48), EYIIGP (SEQ ID NO:49), DPXVTLFGSXHE (SEQ ID NO:50), GSMRSX-LFPXFGSMFS (SEQ ID NO:51), IGGGWQXAWKW (SEQ ID NO:52), LQQFXGINGVLYYTPQILEXAGV (SEQ ID NO:53), LMDXSGRRXLLLXTIPXLI (SEQ ID NO:54), YFCXFVMGFGPXPNILCXEIFPTXVRGL-CIAICA (SEQ ID NO:55), or KVPETKGMPLEVIXEFF (SEQ ID NO:56), where each letter represents an amino acid except "X" which can be any, or no, amino acid. Any, or all, of these elements can be used to identify proteins involved in sugar transport in plants. Minor modifications, such as conserved amino acid substitutions, may be found in some plant sequences.

TABLE 5

Percent Identity of Amino Acid Sequences Deduced From the Nucleotide Sequences of cDNA Clones Encoding Polypeptides Homologous to Arabidopsis-like Sugar Transport Proteins

| Clone | SEQ ID NO. | Percent Identity to gi 3080420 |
|---|---|---|
| contig of:<br>cil1c.pk001.f21<br>crln.pk0143.h10:fis<br>p0002.cgevb73r<br>p0032.crcba66r<br>p0072.comgi92r<br>p0097.cqran41r<br>p0106.cjlpm67r<br>p0114.cimml81r<br>p0128.cpict38r | 2 | 65.6% |

TABLE 5-continued

Percent Identity of Amino Acid Sequences Deduced From the Nucleotide Sequences of cDNA Clones Encoding Polypeptides Homologous to *Arabidopsis*-like Sugar Transport Proteins

| Clone | SEQ ID NO. | Percent Identity to |
|---|---|---|
| contig of: rds1c.pk007.n17 rlr12.pk0013.d11 | 4 | 85.7% |
| rls6.pk0003.d5:fis | 6 | 74.0% |
| contig of: sdp3c.pk012.i1 sfl1.pk0079.a4 sgs4c.pk005.c9 | 8 | 67.9% |
| ssl.pk0022.f1 | 10 | 65.8% |
| wlk8.pk0001.a12 | 12 | 88.0% |
| contig of: wlm96.pk043.e19 wre1n.pk0062.g6 | 14 | 65.2% |
| wre1n.pk0006.b4 | 16 | 75.9% gi 12039327 |
| p0110.cgsmx44r | 32 | 72.8% |

Sequence alignments and percent identity calculations were performed using the Megalign program of the LASER-GENE bioinformatics computing suite (DNASTAR Inc., Madison, Wis.) Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a *Arabidopsis*-like sugar transport proteins. These sequences represent the first corn, soybean, or wheat sequences encoding *Arabidopsis*-like sugar transport proteins known to Applicant.

Example 4

Characterization of cDNA Clones Encoding *Beta-vulgaris*-like Sugar Transport Proteins The BLASTX search using the EST sequences from clones listed in Table 3 revealed similarity of the polypeptides encoded by the cDNAs to *Beta-vulgaris*-like sugar transport proteins from *Beta vulgaris* (NCBI General Identifier No. gi 1778093, SEQ ID NO:30). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 6

BLAST Results for Sequences Encoding Polypeptides Homologous to *Beta-vulgaris*-like Sugar Transport Proteins

| Clone | Status | BLAST pLog Score [NCBI Identifier No. gi 1778093] |
|---|---|---|
| cc1.mn0002.h1 | EST | 53.70 |
| cepe7.pk0018.g3 | EST | 164.00 |

TABLE 6-continued

BLAST Results for Sequences Encoding Polypeptides Homologous to *Beta-vulgaris*-like Sugar Transport Proteins

| Clone | Status | BLAST pLog Score [NCBI Identifier No. gi 1778093] |
|---|---|---|
| contig of: rl0n.pk102.p24 rl0n.pk107.p2 rlr6.pk0005.b10 | Contig | >250.00 |
| contig of: sfl1.pk0058.h12 sgs2c.pk004.o17 sr1.pk0061.g8 sre.pk0032.h6 | Contig | >250.00 |
| wlk8.pk0001.a11 | EST | >250.00 |
| wlm1.pk0012.h1 | EST | >250.00 |

The sequence of the entire cDNA insert in the clones listed in Table 3 was determined. Further sequencing and searching of the DuPont proprietary database allowed the identification of other corn, rice, soybean and/or wheat clones encoding *Beta-vulgaris*-like sugar transport proteins. The BLASTX search using the EST sequences from clones listed in Table 6 revealed similarity of the polypeptides encoded by the cDNAs to *Beta-vulgaris*-like sugar transport proteins from corn (*Zea mays*) (NCBI General Identifier No. gi 8347248) and from rice (*Oryza sativa*) (NCBI General Identifier No. gi 5091611, SEQ ID NO:38). Shown in Table 7 are the BLAST results for individual ESTs ("EST"), sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences derived from an FIS, a contig, or an FIS and PCR and encoding the entire protein ("CGS"):

TABLE 7

BLAST Results for Sequences Encoding Polypeptides Homologous to *Beta-vulgaris*-like Sugar Transport Proteins

| Clone | Status | BLAST pLog Score |
|---|---|---|
| | | NCBI Identifier gi 8347248 |
| p0127.cntak13r | EST | >180.00 |
| | | NCBI Identifier gi 5091611 |
| p0127.cntas61r | Contig | >180.00 |

FIGS. 2A, 2B, 2C and 2D present an alignment of the amino acid sequences set forth in SEQ ID NOs:18, 20, 22, 24, 26, 28, and 36, and the *Beta vulgaris* and rice sequences (SEQ ID NOs:30 and 38). The data in Table 5 represents a calculation of the percent identity of the amino acid sequences set forth in SEQ ID NOs:18, 20, 22, 24, 26, 28, and 36, and the *Beta vulgaris* and rice sequences (SEQ ID NOs:30, and 38). The BLAST pLog score for the corn sequence is the highest possible under the new BLAST format (i.e. >180.00), under the previous search (Table 3) this score would have been >250.00.

The sequence alignments disclose several conserved sequence elements distributed throughout the polypeptide sequences. For instance, some conserved elements include, but are not limited to: PESPRWL (SEQ ID NO:39), PETXG (SEQ ID NO:40), LGYDXIGVMSGA (SEQ ID NO:41), GRXXXGXGVG (SEQ ID NO:42), GIHFFQ (SEQ ID NO:43), or FSXGXG (SEQ ID NO: 44), where each letter represents an amino acid except "X" which can be any, or no, amino acid. Any, or all, of these elements can be used to identify proteins involved in sugar transport in plants. Minor modifications, such as conserved amino acid substitutions, may be found in some plant sequences.

TABLE 8

Percent Identity of Amino Acid Sequences Deduced From the Nucleotide Sequences of cDNA Clones Encoding Polypeptides Homologous to Beta-vulgaris-like Sugar Transport Proteins

| Clone | SEQ ID NO. | Percent Identity to |
|---|---|---|
| | | NCBI Identifier No. gi 1778093 |
| cc1.mn0002.h1 | 18 | 65.3% |
| cepe7.pk0018.g3 | 20 | 56.5% |
| contig of: rl0n.pk102.p24 rl0n.pk107.p2 rlr6.pk0005.b10 | 22 | 60.8% |
| contig of: sfl1.pk0058.h12 sgs2c.pk004.o17 sr1.pk0061.g8 sre.pk0032.h6 | 24 | 65.6% |
| wlk8.pk0001.a11 | 26 | 60.7% |
| wlm1.pk0012.h1 | 28 | 56.0% |
| | | NCBI Identifier No. gi 8347248 |
| p0127.cntak13r | 34 | 99.4% |
| | | NCBI Identifier No. gi 5091611 |
| p0127.cntas61r | 36 | 68.9% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a *Beta-vulgaris*-like sugar transport proteins. These sequences represent the first soybean and wheat sequences encoding *Beta-vulgaris*-like sugar transport proteins known to Applicant.

Example 5

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic ™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 6

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Recombinant DNA Constructs in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM TRIS® HCl (hydroxymethyl)aminomethane hydrochloride at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having sugar transport protein activity, wherein said polypeptide is at least 91% identical to SEQ ID NO: 32 or 36, or
   (b) the full complement of the nucleotide sequence of (a).

2. The polynucleotide of claim 1, wherein the amino acid sequence of the polypeptide and the amino acid sequence of SEQ ID NO:32 or 36 have at least 92% identity.

3. The polynucleotide of claim 1, wherein the amino acid sequence of the polypeptide and the amino acid sequence of SEQ ID NO:32 or 36 have at least 95% identity.

4. The polynucleotide of claim 1, wherein the amino acid sequence of the polypeptide and the amino acid sequence of SEQ ID NO:32 or 36 have at least 98% identity.

5. The polynucleotide of claim 1, wherein the amino acid sequence of the polypeptide comprises the amino acid sequence of SEQ ID NO:32 or 36.

6. The polynucleotide of claim 1 wherein the nucleotide sequence comprises the nucleotide sequence of SEQ ID NO:31 or 35.

7. A vector comprising the polynucleotide of claim 1.

8. A recombinant DNA construct comprising the polynucleotide of claim 1 operably linked to at least one regulatory sequence.

9. A method for transforming a cell, comprising transforming a cell with the polynucleotide of claim 1.

10. A cell comprising the recombinant DNA construct of claim 8.

* * * * *

UNITED STATES PATENT AND TRADEMARK OFFICE
CERTIFICATE OF CORRECTION

PATENT NO.        : 7,041,476 B2                                            Page 1 of 1
APPLICATION NO. : 10/051909
DATED             : May 9, 2006
INVENTOR(S)       : Timothy G. Helentjaris It is certified that error appears in the above-identified patent and that said Letters Patent is hereby corrected as shown below:

Title page, item (75) Inventors, please delete "Heletjaris" and insert therefore --Helentjaris--.

Signed and Sealed this

Thirty-first Day of July, 2007

JON W. DUDAS
*Director of the United States Patent and Trademark Office*

SEQUENCE LISTING

```
<160> NUMBER OF SEQ ID NOS: 38

<210> SEQ ID NO 1
<211> LENGTH: 2824
<212> TYPE: DNA
<213> ORGANISM: Zea mays
<220> FEATURE:
<221> NAME/KEY: unsure
<222> LOCATION: (29)
<221> NAME/KEY: unsure
<222> LOCATION: (622)
<221> NAME/KEY: unsure
<222> LOCATION: (636)
<221> NAME/KEY: unsure
<222> LOCATION: (638)
<221> NAME/KEY: unsure
<222> LOCATION: (669)
<221> NAME/KEY: unsure
<222> LOCATION: (771)
<221> NAME/KEY: unsure
<222> LOCATION: (822)
<221> NAME/KEY: unsure
<222> LOCATION: (856)
<221> NAME/KEY: unsure
<222> LOCATION: (889)
<221> NAME/KEY: unsure
<222> LOCATION: (896)
<221> NAME/KEY: unsure
<222> LOCATION: (944)

<400> SEQUENCE: 1
cccacccccc tccactccac taccacggng gcacggcctg cctctgcagc tctgccctgc      60
tccgcacccc tcgctctcca accccaacgc gcggcgttgc taaaattcac ctcagcgcgt     120
```

```
actccagttt ggccacctca ccacccgccg ccgctgttta agaaggcccc gcgcccgatc    180
ggggatcacg aaccttggcc gccgctgccg gagtggggc gtagatttcc ggcggccatg     240
gggggcgccg tgatggtcgc catcgcggcc tctatcggca acttgctgca gggctgggac    300
aatgcgacaa ttgctggagc cgtcctgtac ataaagaagg aattcaacct gcagagcgag    360
cctctgatcg aaggcctcat cgtcgccatg ttcctcattg gggcaacagt catcacaaca    420
tctccggggc caagggctga ctgcgttggt aggaggccca tgctggtcgc ctcggctgtc    480
ctctacttcg tcagtgggct ggtgatgctt gggcgccaa ttgtgtacat cttgctcctc     540
gcaaggctca ttgatgggtt cggtatcggt ttggcggtca cacttgttcc tctctacatc    600
tccgaaactg caccgcacag anattcttgg ggctgntnga acacgttgcc gcagttcatt    660
ggggtcagng gagggatgtt cctctcctac tgcatggtgt ttgggatgtc cctcatgccc    720
aaacctgatt ggaggctcat gcttggagtt ctgtcgatcc cgtcacttat ntactttgga    780
ctgactgtct tctacttgcc tgaatcacca aggtggcttg tnagcaaagg aaggatggcg    840
gaggcgaaga gagtgntgca aaggctgcgg ggaagagaag atgtctcang ggaganggct    900
cttctagttg aaggtttggg ggtcggtaaa gatacacgta tttnagagta catcattgga    960
cctgccaccg aggcagccga tgatcttgta actgacggtg ataaggaaca aatcacactt   1020
tatgggcctg aagaaggcca gtcatggatt gctcgacctt ctaagggacc catcatgctt   1080
ggaagtgtgc tttctcttgc atctcgtcat gggagcatgg tgaaccagag tgtacccctt   1140
atggatccga ttgtgacact ttttggtagt gtccatgaga atatgcctca agctggagga   1200
agtatgagga gcacattgtt tccaaacttt ggaagtatgt tcagtgtcac agatcagcat   1260
gccaaaaatg agcagtggga tgaagagaat cttcataggg atgacgagga gtacgcatct   1320
gatggtgcag gaggtgacta tgaggacaat ctccatagcc cattgctgtc caggcaggca   1380
acaggtgcga aagggaagga cattgtgcac catggtcacc gtggaagtgc tttgagcatg   1440
agaaggcaaa gcctcttagg ggagggtgga gatggtgtga gcagcactga tatcggtggg   1500
ggatggcagc ttgcttggaa atggtcagag aaggaaggtg agaatggtag aaaggaaggt   1560
ggtttcaaaa gagtctactt gcaccaagag ggagttcctg gctcaagaag gggctcaatt   1620
gtttcacttc ccgtggtgg cgatgttctt gagggtagta agtttgtaca tgctgctgct    1680
ttagtaagtc agtcagcact tttctcaaag ggtcttgctg aaccacgcat gtcagatgct   1740
gccatggttc acccatctga ggtagctgcc aaaggttcac gttggaaaga tttgtttgaa   1800
cctggagtga ggcgtgccct gttagtcggt gttggaattc agatccttca acagtttgct   1860
ggaataaacg tgttctgta ctatacccca caaattcttg agcaagctgg tgtggcagtt   1920 attcttttcca aatttggtct cagctcggca tcagcatcca tcttgatcag ttctctcact   1980
accttactaa tgcttccttg cattggcttt gccatgctgc ttatggatct ttccggaaga   2040 aggttttttgc tgctaggcac aattccaatc ttgatagcat ctctagttat cctggttgtg   2100
tccaatctaa ttgatttggg tacactagcc catgctttgc tctccaccat cagtgttatc   2160
gtctacttct gctgcttcgt tatgggattt ggtcccatcc ccaacatttt atgtgcagag   2220
atctttccaa ccagggttcg tggcctctgt attgccattt gtgcctttac attctggatc   2280
ggagatatca tcgtcaccta cagccttcct gtgatgctga atgctattgg actggcgggt   2340
gttttcagca tatatgcagt cgtatgcttg atttccttg tgttcgtctt ccttaaggtc    2400
cctgagacaa aggggatgcc ccttgaggtt attaccgaat tctttgcagt tggtgcgaag   2460
```

-continued

```
caagcggctg caaaagccta atttctttgg tacctttgtg tgcaactatt gcactgtaag      2520
ttagaaactt gaaggggttt caccaagaag ctcggagaat tactttggat ttgtgtaaat      2580
gttaagggaa cgaacatctg ctcatgctcc tcaaacggta aaaagagtc cctcaatggc       2640 aaataggagt cgttaagttg tcaatgtcat ttaccatatg ttttacctat ttgtactgta      2700
ttataagtca agctattcaa cgctggttgt tgctagaaat ctttagaaca aagatgataa      2760
tgatctgatc tgatgttata atattcaaat ctcaataaa gaaatatcg tttctcaaaa        2820 aaaa                                                                   2824
```

<210> SEQ ID NO 2
<211> LENGTH: 747
<212> TYPE: PRT
<213> ORGANISM: Zea mays
<220> FEATURE:
<221> NAME/KEY: UNSURE
<222> LOCATION: (129)
<221> NAME/KEY: UNSURE
<222> LOCATION: (133)..(134)
<221> NAME/KEY: UNSURE
<222> LOCATION: (144)
<221> NAME/KEY: UNSURE
<222> LOCATION: (178)
<221> NAME/KEY: UNSURE
<222> LOCATION: (207)
<221> NAME/KEY: UNSURE
<222> LOCATION: (218)
<221> NAME/KEY: UNSURE
<222> LOCATION: (220)
<221> NAME/KEY: UNSURE
<222> LOCATION: (236)

<400> SEQUENCE: 2

```
Met Gly Gly Ala Val Met Val Ala Ile Ala Ala Ser Ile Gly Asn Leu
  1               5                  10                  15

Leu Gln Gly Trp Asp Asn Ala Thr Ile Ala Gly Ala Val Leu Tyr Ile
             20                  25                  30

Lys Lys Glu Phe Asn Leu Gln Ser Glu Pro Leu Ile Glu Gly Leu Ile
         35                  40                  45

Val Ala Met Phe Leu Ile Gly Ala Thr Val Ile Thr Thr Ser Pro Gly
     50                  55                  60

Pro Arg Ala Asp Cys Val Gly Arg Arg Pro Met Leu Val Ala Ser Ala
 65                  70                  75                  80

Val Leu Tyr Phe Val Ser Gly Leu Val Met Leu Trp Ala Pro Ile Val
                 85                  90                  95

Tyr Ile Leu Leu Leu Ala Arg Leu Ile Asp Gly Phe Gly Ile Gly Leu
            100                 105                 110

Ala Val Thr Leu Val Pro Leu Tyr Ile Ser Glu Thr Ala Pro His Arg
        115                 120                 125

Xaa Ser Trp Gly Xaa Xaa Asn Thr Leu Pro Gln Phe Ile Gly Val Xaa
    130                 135                 140

Gly Gly Met Phe Leu Ser Tyr Cys Met Val Phe Gly Met Ser Leu Met
145                 150                 155                 160

Pro Lys Pro Asp Trp Arg Leu Met Leu Gly Val Leu Ser Ile Pro Ser
                165                 170                 175

Leu Xaa Tyr Phe Gly Leu Thr Val Phe Tyr Leu Pro Glu Ser Pro Arg
            180                 185                 190

Trp Leu Val Ser Lys Gly Arg Met Ala Glu Ala Lys Arg Val Xaa Gln
        195                 200                 205

Arg Leu Arg Gly Arg Glu Asp Val Ser Xaa Glu Xaa Ala Leu Leu Val
```

-continued

```
            210                 215                 220
Glu Gly Leu Gly Val Gly Lys Asp Thr Arg Ile Xaa Glu Tyr Ile Ile
225                 230                 235                 240

Gly Pro Ala Thr Glu Ala Ala Asp Asp Leu Val Thr Asp Gly Asp Lys
                245                 250                 255

Glu Gln Ile Thr Leu Tyr Gly Pro Glu Gly Gln Ser Trp Ile Ala
            260                 265                 270

Arg Pro Ser Lys Gly Pro Ile Met Leu Gly Ser Val Leu Ser Leu Ala
                275                 280                 285

Ser Arg His Gly Ser Met Val Asn Gln Ser Val Pro Leu Met Asp Pro
    290                 295                 300

Ile Val Thr Leu Phe Gly Ser Val His Glu Asn Met Pro Gln Ala Gly
305                 310                 315                 320

Gly Ser Met Arg Ser Thr Leu Phe Pro Asn Phe Gly Ser Met Phe Ser
                325                 330                 335

Val Thr Asp Gln His Ala Lys Asn Glu Gln Trp Asp Glu Glu Asn Leu
            340                 345                 350

His Arg Asp Asp Glu Glu Tyr Ala Ser Asp Gly Ala Gly Gly Asp Tyr
    355                 360                 365

Glu Asp Asn Leu His Ser Pro Leu Leu Ser Arg Gln Ala Thr Gly Ala
370                 375                 380

Glu Gly Lys Asp Ile Val His His Gly His Arg Gly Ser Ala Leu Ser
385                 390                 395                 400

Met Arg Arg Gln Ser Leu Leu Gly Glu Gly Gly Asp Gly Val Ser Ser
                405                 410                 415

Thr Asp Ile Gly Gly Gly Trp Gln Leu Ala Trp Lys Trp Ser Glu Lys
            420                 425                 430

Glu Gly Glu Asn Gly Arg Lys Glu Gly Gly Phe Lys Arg Val Tyr Leu
                435                 440                 445

His Gln Glu Gly Val Pro Gly Ser Arg Arg Gly Ser Ile Val Ser Leu
            450                 455                 460

Pro Gly Gly Gly Asp Val Leu Glu Gly Ser Glu Phe Val His Ala Ala
465                 470                 475                 480

Ala Leu Val Ser Gln Ser Ala Leu Phe Ser Lys Gly Leu Ala Glu Pro
                485                 490                 495

Arg Met Ser Asp Ala Ala Met Val His Pro Ser Glu Val Ala Ala Lys
            500                 505                 510

Gly Ser Arg Trp Lys Asp Leu Phe Glu Pro Gly Val Arg Arg Ala Leu
                515                 520                 525

Leu Val Gly Val Gly Ile Gln Ile Leu Gln Gln Phe Ala Gly Ile Asn
530                 535                 540

Gly Val Leu Tyr Tyr Thr Pro Gln Ile Leu Glu Gln Ala Gly Val Ala
545                 550                 555                 560

Val Ile Leu Ser Lys Phe Gly Leu Ser Ser Ala Ser Ala Ser Ile Leu
                565                 570                 575

Ile Ser Ser Leu Thr Thr Leu Leu Met Leu Pro Cys Ile Gly Phe Ala
            580                 585                 590

Met Leu Leu Met Asp Leu Ser Gly Arg Arg Phe Leu Leu Leu Gly Thr
                595                 600                 605

Ile Pro Ile Leu Ile Ala Ser Leu Val Ile Leu Val Val Ser Asn Leu
            610                 615                 620

Ile Asp Leu Gly Thr Leu Ala His Ala Leu Leu Ser Thr Ile Ser Val
625                 630                 635                 640
```

```
Ile Val Tyr Phe Cys Cys Phe Val Met Gly Phe Gly Pro Ile Pro Asn
                645                 650                 655

Ile Leu Cys Ala Glu Ile Phe Pro Thr Arg Val Arg Gly Leu Cys Ile
            660                 665                 670

Ala Ile Cys Ala Phe Thr Phe Trp Ile Gly Asp Ile Val Thr Tyr
        675                 680                 685

Ser Leu Pro Val Met Leu Asn Ala Ile Gly Leu Ala Gly Val Phe Ser
    690                 695                 700

Ile Tyr Ala Val Val Cys Leu Ile Ser Phe Val Phe Val Phe Leu Lys
705                 710                 715                 720

Val Pro Glu Thr Lys Gly Met Pro Leu Glu Val Ile Thr Glu Phe Phe
                725                 730                 735

Ala Val Gly Ala Lys Gln Ala Ala Ala Lys Ala
                740                 745

<210> SEQ ID NO 3
<211> LENGTH: 443
<212> TYPE: DNA
<213> ORGANISM: Oryza sativa
<220> FEATURE:
<221> NAME/KEY: unsure
<222> LOCATION: (193)
<221> NAME/KEY: unsure
<222> LOCATION: (388)
<221> NAME/KEY: unsure
<222> LOCATION: (435)
<221> NAME/KEY: unsure
<222> LOCATION: (439)

<400> SEQUENCE: 3
gaagagctca cccccccccc ctcggccctg gactccctcc tccaaatctc ccctaaaagc      60
ttcccaattt ggcgagaatt ccccatatat ttgccccatc tcggcgtccc aacgagccct     120
tccagattcc cagccgcctc tcttcttgtt aggggatccg aaatctcggt ggacgagaga     180
cttggtggta atnattcgcc ggccatggcg ggcgccgtgc tggtcgccat cgcggcctcc     240
atcggcaact gctgcaggg ctgggataat gcaaccattg caggtgcggt actgtacatc     300
aagaaggaat tcaacttgca tagcgacccc cttatcgaag gtctgatcgt ggccatgtcg     360
ctcattgggg ccaccatcat cacgacgntc tctgcgagca ggtggctgac tcttttggta     420
tggcggccca tgctnatcnc ttc                                             443

<210> SEQ ID NO 4
<211> LENGTH: 131
<212> TYPE: PRT
<213> ORGANISM: Oryza sativa
<220> FEATURE:
<221> NAME/KEY: UNSURE
<222> LOCATION: (65)
<221> NAME/KEY: UNSURE
<222> LOCATION: (130)

<400> SEQUENCE: 4

Glu Glu Leu Thr Pro Pro Ser Ala Leu Asp Ser Leu Leu Gln Ile
 1               5                  10                  15

Ser Pro Lys Ser Phe Pro Ile Trp Arg Glu Phe Pro Ile Tyr Leu Pro
                20                  25                  30

His Leu Gly Val Pro Thr Ser Pro Ser Arg Phe Pro Ala Ala Ser Leu
            35                  40                  45

Leu Val Arg Gly Ser Glu Ile Ser Val Asp Glu Arg Leu Gly Gly Asn
        50                  55                  60
```

```
Xaa Ser Pro Ala Met Ala Gly Ala Val Leu Val Ala Ile Ala Ala Ser
 65                  70                  75                  80

Ile Gly Asn Leu Leu Gln Gly Trp Asp Asn Ala Thr Ile Ala Gly Ala
             85                  90                  95

Val Leu Tyr Ile Lys Lys Glu Phe Asn Leu His Ser Asp Pro Leu Ile
        100                 105                 110

Glu Gly Leu Ile Val Ala Met Ser Leu Ile Gly Ala Thr Ile Ile Thr
        115                 120                 125

Thr Xaa Ser
        130

<210> SEQ ID NO 5
<211> LENGTH: 870
<212> TYPE: DNA
<213> ORGANISM: Oryza sativa

<400> SEQUENCE: 5
gcacgaggtt ctaaccttga ttctggtcaa tattctggat gtggggacca tggttcatgc     60
ctcactgtcc acagtcagtg tcatactcta cttctgcttc tttgtcatgg ggttcgggcc    120
tattccaaac attctctgtg cagagatttt cccgaccacc gttcgtggca tctgcatagc    180
catctgtgcc ctaacattct ggatcggtga tatcattgtg acatacaccc tccccgtgat    240
gctcaacgcc attggactcg ctggagtgtt tggaatctac gcagtggtct gcatactggc    300
tttcctgttt gtcttcatga aggtgccgga gacaaagggc atgcctcttg aagtcatcac    360
cgagttcttc tctgtcggag caaagcaggc caaggaggac tagttgctcg atcaagtga    420 tcaatcagat tgctggtggt aattttgttg cttccaaatc gcgctgcggg ttaaacctgt    480
gatggatgct tgttaaaga atcttggaag agatcaaaat gcagtgagcc taaagagatg    540
atttggctgt acatcatgag ctgaatcct gtcgtagact ggattttgga gcttaggata    600
tgtagatcat ctgttccttt tggtttggtc attttccatt tgtgtttctt tggaattctt    660
ctccctgtaa ctagtggtct atcacagttg tgttactggt tttgccttac tcttgagttt    720
gttttcttct ctcggttgtg agttctgaat attagcatag ccgagtacta gttctgaatt    780
ggtttcctct ctgctgaaca tctttcattg atgcttggat ttcatcaaaa aaaaaaaaa    840 aaaactcgag ggggagcccg gtacacatct                                    870

<210> SEQ ID NO 6
<211> LENGTH: 131
<212> TYPE: PRT
<213> ORGANISM: Oryza sativa

<400> SEQUENCE: 6

Val Leu Thr Leu Ile Leu Val Asn Ile Leu Asp Val Gly Thr Met Val
  1               5                  10                  15

His Ala Ser Leu Ser Thr Val Ser Val Ile Leu Tyr Phe Cys Phe Phe
             20                  25                  30

Val Met Gly Phe Gly Pro Ile Pro Asn Ile Leu Cys Ala Glu Ile Phe
         35                  40                  45

Pro Thr Thr Val Arg Gly Ile Cys Ile Ala Ile Cys Ala Leu Thr Phe
     50                  55                  60

Trp Ile Gly Asp Ile Ile Val Thr Tyr Thr Leu Pro Val Met Leu Asn
 65                  70                  75                  80

Ala Ile Gly Leu Ala Gly Val Phe Gly Ile Tyr Ala Val Val Cys Ile
             85                  90                  95
```

```
Leu Ala Phe Leu Phe Val Phe Met Lys Val Pro Glu Thr Lys Gly Met
            100                 105                 110

Pro Leu Glu Val Ile Thr Glu Phe Phe Ser Val Gly Ala Lys Gln Ala
        115                 120                 125

Lys Glu Asp
    130

<210> SEQ ID NO 7
<211> LENGTH: 2601
<212> TYPE: DNA
<213> ORGANISM: Glycine max

<400> SEQUENCE: 7
```

| | | | | |
|---|---|---|---|---|
| gttgcttaac | ccttgttgag | tgaagtgagc | aagggaatg | gcgatctgaa | attcggatac | 60 |
| tttaattgct | tctcgctttc | accgaccgaa | ctcaatttat | agatactccg | tcaacctcaa | 120 |
| tcccaactaa | ctagcagttc | cttgctgctg | ctccttcttc | accatatcgc | agtaatgaaa | 180 |
| ggtgccgtcc | ttgttgctat | tgccgcttcc | attggtaatt | tcctccaagg | atgggataat | 240 |
| gctaccatcg | ccggggctaa | tggttacatt | aagaaagacc | ttgctttggg | aacaactatg | 300 |
| gaaaggcttg | tggtgggcat | gtccctgatt | ggagcaacgg | taatcaccac | atgctctggt | 360 |
| cctatagcgg | attggctcgg | tcggcgaccc | atgatgataa | tctcatctgt | gctctatttc | 420 |
| ttgggtggtt | tggtgatgct | gtggtcccca | atgtgtatg | tgttgtgctt | ggcgaggcta | 480 |
| cttgatggat | ttgggattgg | ccttgctgtg | actcttgtcc | cggtctatat | atctgaaacg | 540 |
| gcgccgtctg | aaataagggg | tcgttgaat | acgcttcctc | agttcagtgg | ctctggagga | 600 |
| atgttttgt | cgtactgtat | ggttttggc | atgtcattga | gtcccgcgcc | tagctggagg | 660 |
| ctcatgcttg | gggttctgtc | tattccttct | ctcttgtatt | ttgcattgac | cattttttc | 720 |
| ttgcccgagt | ctcctcggtg | gctggtcagc | aaaggaagga | tgctcgaggc | taagaaggtg | 780 |
| ctccaaagat | gcgcggaag | ggaggatgtg | tcaggcgaga | tggcattgct | ggttgaaggt | 840 |
| ctcgggattg | ggggtgatac | atctatcgaa | gagtacataa | ttggccctgc | tgacgatgtg | 900 |
| gctgatggtc | atgaacatgc | aacagagaaa | gataaaattc | gattatatgg | atcccaagca | 960 |
| ggcctttctt | ggttatcaaa | acctgtcact | ggacagagtt | ctattggcct | tgcgtcacac | 1020 |
| catggaagca | tcatcaacca | aagcatgccc | ctcatggatc | ctctggtgac | actgtttggt | 1080 |
| agcattcatg | agaagctccc | cgagacagga | gcaagaggaa | gcatgcgaag | cactctgttt | 1140 |
| ccaaattttg | gaagcatgtt | cagcactgct | gagccgcatg | ctaaaattga | acaatgggat | 1200 |
| gaagaaagct | tacaaaggga | acgtgaggac | tacatgtcag | atgcaacccg | tggggactcc | 1260 |
| gatgataatt | tgcacagtcc | tttaatctca | cgccaaacaa | caagccttga | aaagactta | 1320 |
| cctcctcctc | cttcccatgg | cagtatcctt | ggcagcatga | ggcgtcacag | tagtctcatg | 1380 |
| caagggtcag | gtgagcaagg | tggtagtaca | ggtattggtg | gtggctggca | actggcatgg | 1440 |
| aaatggactg | ataaaggtga | ggatggaaaa | caacaaggag | ggtttaaaag | gatttattta | 1500 |
| catgaggagg | gagtttctgc | atctcgtcgt | ggatccattg | tatcgattcc | cggtgaaggc | 1560 |
| gaatttgtcc | aggctgctgc | cttggtaagc | caacccgctc | tttactccaa | ggagcttatt | 1620 |
| gatggacacc | cagttgggcc | tgcaatggtt | cacccatctg | agacagcttc | aaggggcca | 1680 |
| agttggaaag | ctcttcttga | accagggggtt | aagcatgcat | tggttgttgg | agttggaata | 1740 |
| caaatacttc | agcagttttc | agggataaat | ggggttctat | attacacacc | tcaaatcctt | 1800 |
| gaagaggccg | gtgttgaagt | tcttctttca | gatataggca | ttggctcaga | gtcggcatca | 1860 |

-continued

```
ttccttatca gtgctttcac aaccttcttg atgcttccct gtataggcgt agccatgaag    1920
ctcatggatg tttcaggcag aaggcagttg ctacttacta caatccccgt gctgattgtg    1980
tcactcatta ttttggtcat tggaagcctg gtaaattttg caatgtcgc ccatgcagca     2040 atctcaacag tatgcgttgt ggtttatttc tgctgctttg tgatgggtta tggaccaatt    2100
ccaaacatcc tttgctcaga gattttcccc actagggtgc gtggcctctg cattgctatc    2160
tgtgcattag tgttctggat tggagacatc atcatcacat actcgctgcc tgtgatgctc    2220
ggctctttag gacttggtgg tgtattcgcc atttacgcag ttgtttgttt catctcgtgg    2280
atatttgtgt ttttgaaggt tccagaaaca aagggcatgc cccttgaagt catctctgaa    2340 ttctttctg ttggagcaaa gcaggctgct tctgccaaga atgagtgaca caacacaagt     2400
ccgttatata ctctgtaact ttagttgtta aagccatcat ctctcgtctt tacagatttt    2460
gcttttcata gtttatttg gaggaagata ttttgaaaca tatgggtttt tttttctttc     2520
ataaaaataa aacccttccc ttttgggtg gggaaaagaa aaaaaaaaa aaaaaaaaa       2580 aaaaaaaaaa aaaaaaaaaa a                                              2601
```

<210> SEQ ID NO 8
<211> LENGTH: 737
<212> TYPE: PRT
<213> ORGANISM: Glycine max

<400> SEQUENCE: 8

```
Met Lys Gly Ala Val Leu Val Ala Ile Ala Ser Ile Gly Asn Phe
 1               5                  10                  15

Leu Gln Gly Trp Asp Asn Ala Thr Ile Ala Gly Ala Asn Gly Tyr Ile
                20                  25                  30

Lys Lys Asp Leu Ala Leu Gly Thr Thr Met Glu Arg Leu Val Val Gly
            35                  40                  45

Met Ser Leu Ile Gly Ala Thr Val Ile Thr Thr Cys Ser Gly Pro Ile
        50                  55                  60

Ala Asp Trp Leu Gly Arg Arg Pro Met Met Ile Ile Ser Ser Val Leu
    65                  70                  75                  80

Tyr Phe Leu Gly Gly Leu Val Met Leu Trp Ser Pro Asn Val Tyr Val
                    85                  90                  95

Leu Cys Leu Ala Arg Leu Leu Asp Gly Phe Gly Ile Gly Leu Ala Val
                100                 105                 110

Thr Leu Val Pro Val Tyr Ile Ser Glu Thr Ala Pro Ser Glu Ile Arg
            115                 120                 125

Gly Ser Leu Asn Thr Leu Pro Gln Phe Ser Gly Ser Gly Met Phe
        130                 135                 140

Leu Ser Tyr Cys Met Val Phe Gly Met Ser Leu Ser Pro Ala Pro Ser
145                 150                 155                 160

Trp Arg Leu Met Leu Gly Val Leu Ser Ile Pro Ser Leu Leu Tyr Phe
                    165                 170                 175

Ala Leu Thr Ile Phe Phe Leu Pro Glu Ser Pro Arg Trp Leu Val Ser
                180                 185                 190

Lys Gly Arg Met Leu Glu Ala Lys Lys Val Leu Gln Arg Leu Arg Gly
            195                 200                 205

Arg Glu Asp Val Ser Gly Glu Met Ala Leu Leu Val Glu Gly Leu Gly
        210                 215                 220

Ile Gly Gly Asp Thr Ser Ile Glu Glu Tyr Ile Ile Gly Pro Ala Asp
225                 230                 235                 240
```

-continued

```
Asp Val Ala Asp Gly His Glu His Ala Thr Glu Lys Asp Lys Ile Arg
                245                 250                 255

Leu Tyr Gly Ser Gln Ala Gly Leu Ser Trp Leu Ser Lys Pro Val Thr
            260                 265                 270

Gly Gln Ser Ser Ile Gly Leu Ala Ser His His Gly Ser Ile Ile Asn
        275                 280                 285

Gln Ser Met Pro Leu Met Asp Pro Leu Val Thr Leu Phe Gly Ser Ile
    290                 295                 300

His Glu Lys Leu Pro Glu Thr Gly Ala Arg Gly Ser Met Arg Ser Thr
305                 310                 315                 320

Leu Phe Pro Asn Phe Gly Ser Met Phe Ser Thr Ala Glu Pro His Ala
                325                 330                 335

Lys Ile Glu Gln Trp Asp Glu Glu Ser Leu Gln Arg Glu Arg Glu Asp
            340                 345                 350

Tyr Met Ser Asp Ala Thr Arg Gly Asp Ser Asp Asp Asn Leu His Ser
        355                 360                 365

Pro Leu Ile Ser Arg Gln Thr Thr Ser Leu Glu Lys Asp Leu Pro Pro
    370                 375                 380

Pro Pro Ser His Gly Ser Ile Leu Gly Ser Met Arg Arg His Ser Ser
385                 390                 395                 400

Leu Met Gln Gly Ser Gly Glu Gln Gly Ser Thr Gly Ile Gly Gly
                405                 410                 415

Gly Trp Gln Leu Ala Trp Lys Trp Thr Asp Lys Gly Glu Asp Gly Lys
            420                 425                 430

Gln Gln Gly Gly Phe Lys Arg Ile Tyr Leu His Glu Glu Gly Val Ser
        435                 440                 445

Ala Ser Arg Arg Gly Ser Ile Val Ser Ile Pro Gly Glu Gly Glu Phe
    450                 455                 460

Val Gln Ala Ala Ala Leu Val Ser Gln Pro Ala Leu Tyr Ser Lys Glu
465                 470                 475                 480

Leu Ile Asp Gly His Pro Val Gly Pro Ala Met Val His Pro Ser Glu
                485                 490                 495

Thr Ala Ser Lys Gly Pro Ser Trp Lys Ala Leu Leu Glu Pro Gly Val
            500                 505                 510

Lys His Ala Leu Val Val Gly Val Gly Ile Gln Ile Leu Gln Gln Phe
        515                 520                 525

Ser Gly Ile Asn Gly Val Leu Tyr Tyr Thr Pro Gln Ile Leu Glu Glu
    530                 535                 540

Ala Gly Val Glu Val Leu Leu Ser Asp Ile Gly Ile Gly Ser Glu Ser
545                 550                 555                 560

Ala Ser Phe Leu Ile Ser Ala Phe Thr Thr Phe Leu Met Leu Pro Cys
                565                 570                 575

Ile Gly Val Ala Met Lys Leu Met Asp Val Ser Gly Arg Arg Gln Leu
            580                 585                 590

Leu Leu Thr Thr Ile Pro Val Leu Ile Val Ser Leu Ile Ile Leu Val
        595                 600                 605

Ile Gly Ser Leu Val Asn Phe Gly Asn Val Ala His Ala Ala Ile Ser
    610                 615                 620

Thr Val Cys Val Val Val Tyr Phe Cys Cys Phe Val Met Gly Tyr Gly
625                 630                 635                 640

Pro Ile Pro Asn Ile Leu Cys Ser Glu Ile Phe Pro Thr Arg Val Arg
                645                 650                 655
```

```
Gly Leu Cys Ile Ala Ile Cys Ala Leu Val Phe Trp Ile Gly Asp Ile
            660                 665                 670

Ile Ile Thr Tyr Ser Leu Pro Val Met Leu Gly Ser Leu Gly Leu Gly
        675                 680                 685

Gly Val Phe Ala Ile Tyr Ala Val Val Cys Phe Ile Ser Trp Ile Phe
    690                 695                 700

Val Phe Leu Lys Val Pro Glu Thr Lys Gly Met Pro Leu Glu Val Ile
705                 710                 715                 720

Ser Glu Phe Phe Ser Val Gly Ala Lys Gln Ala Ala Ser Ala Lys Asn
                725                 730                 735

Glu

<210> SEQ ID NO 9
<211> LENGTH: 1692
<212> TYPE: DNA
<213> ORGANISM: Glycine max

<400> SEQUENCE: 9
gcacgaggga tccgtccaga gaaaaagatc aaattaagtt gtatggacca gaacaaggcc      60
agtcctgggt tgctagacct gttgctggac caaattctgt tggccttgta tctaggaaag     120
gaagcatggc aaatccaagc agtctagtgg accctctagt gaccctcttt ggtagtgtac     180
atgagaagct cccagaaaca ggaagcaccc ttttccaca ctttgggagt atgttcagtg      240
ttggggggaaa tcagccaagg aatgaagatt gggatgagga agcctagcc agagagggtg     300
atgattatgt ctctgatgct ggtgattctg atgacaattt gcagagtcca ttgatctcac     360
gtcaaacaac gagtctggat aaggacatac ctcctcatgc ccatagtaac cttgcaagca     420
tgaggcaagg tagtctttta catggaaatt caggagaacc cactggtagt actgggattg     480
gtggtggttg gcagctagca tggaaatggt ctgaaagaga gggcccagat ggaaagaagg     540
aaggtggctt caagagaata tatttacacc aagatggtgg ttctggatct agacgtgggt     600
ctgtggtttc actccctggc ggtgatttac caactgacag tgaggttgta caggctgctg     660
ctctggtgag tcagcctgcc ctttataatg aggaccttat gcgtcaacgg ccagttggac     720
cagctatgat tcatccctct gaaacaattg caaagggcc aagttggagt gatcttttg      780
aacctggggt gaagcatgca ttgattgtgg ggtgggaat gcaaattctt cagcagttct     840
ctggtataaa tggggtcctc tactatacgc ctcaaattct tgagcaggca ggtgttggtt     900
atcttctttc aagcctaggc cttggttcta cttcttcatc ctttcttatt agtgcggtga     960
caaccttgtt gatgcttcct tgtatagcca ttgccatgag gctcatggat atttcaggca    1020
gaaggacttt gctgctcagt acaatccccg tcctaatagc agctcttctc atattagtcc    1080
tgggaagtct tgtggatttg ggatccactg caaatgcatc aatctcaacc attagtgtta    1140
ttgtctatt ctgtttcttt gtcatgggat ttggaccaat tcctaatata ctttgtgcag    1200
agatcttccc cactcgagtt cgtggtctct gcattgctat ttgtgccctt accttttgga    1260
tctgtgatat cattgtcacc tacacactcc cagttatgct caattctgta ggcctcgctg    1320
gtgttttttgg tatttatgct gtcgtgtgct tcatagcatg ggtgtttgtc tttttgaaag    1380
ttccagaaac caagggcatg ccactggaag tgatcattga gttcttctct gtcggagcaa    1440
aacagtttga cgatgccaag cacaactgac ccaaggacat gataaattca aagttttgac    1500
ggtaccttct aattattttc aatctacggc tgtttgaaat ttcccctct tttaaaattt     1560
tatttctat ttattctctc ttttccgtgg gttgagattg agaacaagaa aactttgttt    1620
```

```
ctgtaaagaa aaatgttcat tttctggttc atttatggaa ctttatatac ttcctaaaaa      1680
aaaaaaaaaa aa                                                          1692

<210> SEQ ID NO 10
<211> LENGTH: 486
<212> TYPE: PRT
<213> ORGANISM: Glycine max

<400> SEQUENCE: 10

Asp Pro Ser Arg Glu Lys Asp Gln Ile Lys Leu Tyr Gly Pro Glu Gln
  1               5                  10                  15

Gly Gln Ser Trp Val Ala Arg Pro Val Ala Gly Pro Asn Ser Val Gly
             20                  25                  30

Leu Val Ser Arg Lys Gly Ser Met Ala Asn Pro Ser Ser Leu Val Asp
         35                  40                  45

Pro Leu Val Thr Leu Phe Gly Ser Val His Glu Lys Leu Pro Glu Thr
     50                  55                  60

Gly Ser Thr Leu Phe Pro His Phe Gly Ser Met Phe Ser Val Gly Gly
 65                  70                  75                  80

Asn Gln Pro Arg Asn Glu Asp Trp Asp Glu Ser Leu Ala Arg Glu
                 85                  90                  95

Gly Asp Asp Tyr Val Ser Asp Ala Gly Asp Ser Asp Asp Asn Leu Gln
            100                 105                 110

Ser Pro Leu Ile Ser Arg Gln Thr Thr Ser Leu Asp Lys Asp Ile Pro
        115                 120                 125

Pro His Ala His Ser Asn Leu Ala Ser Met Arg Gln Gly Ser Leu Leu
    130                 135                 140

His Gly Asn Ser Gly Glu Pro Thr Gly Ser Thr Gly Ile Gly Gly Gly
145                 150                 155                 160

Trp Gln Leu Ala Trp Lys Trp Ser Glu Arg Glu Gly Pro Asp Gly Lys
                165                 170                 175

Lys Glu Gly Gly Phe Lys Arg Ile Tyr Leu His Gln Asp Gly Gly Ser
            180                 185                 190

Gly Ser Arg Arg Gly Ser Val Val Ser Leu Pro Gly Gly Asp Leu Pro
        195                 200                 205

Thr Asp Ser Glu Val Val Gln Ala Ala Leu Val Ser Gln Pro Ala
    210                 215                 220

Leu Tyr Asn Glu Asp Leu Met Arg Gln Arg Pro Val Gly Pro Ala Met
225                 230                 235                 240

Ile His Pro Ser Glu Thr Ile Ala Lys Gly Pro Ser Trp Ser Asp Leu
                245                 250                 255

Phe Glu Pro Gly Val Lys His Ala Leu Ile Val Gly Val Gly Met Gln
            260                 265                 270

Ile Leu Gln Gln Phe Ser Gly Ile Asn Gly Val Leu Tyr Tyr Thr Pro
        275                 280                 285

Gln Ile Leu Glu Gln Ala Gly Val Gly Tyr Leu Leu Ser Ser Leu Gly
    290                 295                 300

Leu Gly Ser Thr Ser Ser Ser Phe Leu Ile Ser Ala Val Thr Thr Leu
305                 310                 315                 320

Leu Met Leu Pro Cys Ile Ala Ile Ala Met Arg Leu Met Asp Ile Ser
                325                 330                 335

Gly Arg Arg Thr Leu Leu Leu Ser Thr Ile Pro Val Leu Ile Ala Ala
            340                 345                 350

Leu Leu Ile Leu Val Leu Gly Ser Leu Val Asp Leu Gly Ser Thr Ala
```

```
                355                 360                 365
Asn Ala Ser Ile Ser Thr Ile Ser Val Ile Val Tyr Phe Cys Phe Phe
    370                 375                 380

Val Met Gly Phe Gly Pro Ile Pro Asn Ile Leu Cys Ala Glu Ile Phe
385                 390                 395                 400

Pro Thr Arg Val Arg Gly Leu Cys Ile Ala Ile Cys Ala Leu Thr Phe
                405                 410                 415

Trp Ile Cys Asp Ile Ile Val Thr Tyr Thr Leu Pro Val Met Leu Asn
                420                 425                 430

Ser Val Gly Leu Ala Gly Val Phe Gly Ile Tyr Ala Val Val Cys Phe
                435                 440                 445

Ile Ala Trp Val Phe Val Phe Leu Lys Val Pro Glu Thr Lys Gly Met
    450                 455                 460

Pro Leu Glu Val Ile Ile Glu Phe Phe Ser Val Gly Ala Lys Gln Phe
465                 470                 475                 480

Asp Asp Ala Lys His Asn
                485

<210> SEQ ID NO 11
<211> LENGTH: 510
<212> TYPE: DNA
<213> ORGANISM: Triticum aestivum
<220> FEATURE:
<221> NAME/KEY: unsure
<222> LOCATION: (421)
<221> NAME/KEY: unsure
<222> LOCATION: (434)
<221> NAME/KEY: unsure
<222> LOCATION: (441)
<221> NAME/KEY: unsure
<222> LOCATION: (458)
<221> NAME/KEY: unsure
<222> LOCATION: (483)
<221> NAME/KEY: unsure
<222> LOCATION: (493)
<221> NAME/KEY: unsure
<222> LOCATION: (498)

<400> SEQUENCE: 11
cggtggcagc cggggcagtg aaggagtggt agctcttggc tcctatttga ggcggcttcg     60
ctcggttctg atctaccgca ccacaccacc acaccacacc aggggcctgc cgcttcttgg    120
gcttctccat ctcatctcct tggttggttc tctactagag aggcgcagct gcagggatcc    180
ttggtggaga ggagggaaga agatgtcggg tgctgcactg gtcgcgattg cggcttccat    240
tggcaatctg ctgcaggggt gggacaatgc caccatcgct ggtgctgttc tgtacatcaa    300
gaaggaattc cagctcgaaa ataatccgac tgtggagggg ctcatcgtgg catgtcctca    360
tcgggtgcaa catcatcaca cattctccgg gccagtatca aactggggttg ccgggcccta    420 ngccatctcc ttgntttcaa ntcccaaggg ctaatcanct aggcaccaat gtcaatgtgc    480
gcnccggaac ctntcaaggg ttggaacgtt                                     510

<210> SEQ ID NO 12
<211> LENGTH: 117
<212> TYPE: PRT
<213> ORGANISM: Triticum aestivum

<400> SEQUENCE: 12

Gly Gly Ser Arg Gly Ser Glu Gly Gly Val Ala Leu Gly Ser Tyr Leu
  1               5                  10                  15

Arg Arg Leu Arg Ser Val Leu Ile Tyr Arg Thr Thr Pro Pro His His
```

```
                  20                  25                  30
Thr Arg Gly Leu Pro Leu Leu Gly Leu Leu His Leu Ile Ser Leu Val
         35                  40                  45
Gly Ser Leu Leu Glu Arg Arg Ser Cys Arg Asp Pro Trp Trp Arg Gly
     50                  55                  60
Gly Lys Lys Met Ser Gly Ala Ala Leu Val Ala Ile Ala Ala Ser Ile
 65                  70                  75                  80
Gly Asn Leu Leu Gln Gly Trp Asp Asn Ala Thr Ile Ala Gly Ala Val
                 85                  90                  95
Leu Tyr Ile Lys Lys Glu Phe Gln Leu Glu Asn Asn Pro Thr Val Glu
             100                 105                 110
Gly Leu Ile Val Ala
         115

<210> SEQ ID NO 13
<211> LENGTH: 1487
<212> TYPE: DNA
<213> ORGANISM: Triticum aestivum

<400> SEQUENCE: 13
```

| | | | | | |
|---|---|---|---|---|---|
| tctcttggaa | agagggtggg | gaggcagtca | gcagcactgg | tattggtggg | gggtggcaac | 60 |
| tcgcatggaa | atggtcggag | cgacaaggcg | aggatggcaa | gaaggaagga | ggcttcaaaa | 120 |
| gaatctactt | gcaccaagag | ggggtggccg | actcaagaag | gggctctgtt | gtttcacttc | 180 |
| ctggtggggg | tgatgccacg | caaggggca | gtgggtttat | acatgctgct | gctttggtaa | 240 |
| gccactcggc | tctttactcc | aaggatctta | tggaagagcg | tatggcggcc | ggtccagcca | 300 |
| tgattcatcc | attggaggca | gctcccaaag | gttcaatctg | aaagatctg | tttgaacctg | 360 |
| gtgtgaggcg | tgcattgttc | gtcggtgttg | gaattcagat | gcttcagcag | tttgctggaa | 420 |
| taaatggagt | tctctactat | actcctcaaa | ttctggagca | agctggtgtg | gctgttcttc | 480 |
| tttccaatct | tggcctcagt | tcagcatcag | catccatctt | gatcagttct | ctcaccacct | 540 |
| tactcatgct | cccaagcatt | ggtgtagcca | tgagacttat | ggatatatct | ggaagaaggt | 600 |
| ttctgctact | gggcacaatt | cccatcttga | tagcatccct | aattgttttg | ggtgtggtca | 660 |
| atgttatcaa | cttgagtacg | gtgccccacg | ctgtgctctc | cacagttagc | gtcattgtct | 720 |
| acttctgctg | ctttgtcatg | ggctttggcc | cgatccccaa | cattctatgt | gcagagattt | 780 |
| tccccaccag | agtccgtggt | gtctgcatcg | ctatttgcgc | cctcacattc | tggatttgtg | 840 |
| acattattgt | tacctacagc | ctgcctgtga | tgctgaatgc | tattggtcta | gcgggtgtct | 900 |
| ttggtatata | tgcagtcgtt | tgctgcattg | cctttgtgtt | cgtctaccta | aaggtcccag | 960 |
| agacaaaggg | catgcccctc | gaggtcatca | ccgagttctt | tgcggttggg | gcgaagcaag | 1020 |
| cgcaggccac | cattgcctga | ttcatcatgg | agctttgttt | tcagtttgca | cactgcggtc | 1080 |
| tgcgctgaaa | attgcaaatt | ggacgggtcc | tcgtgaggaa | cggaaaaact | tttgagttgt | 1140 |
| aaatgagaca | gctacccaaa | gagctcatca | cgaggaacgg | gaagctgtaa | aagtaggagg | 1200 |
| atctcatgcc | cccatttcat | cgtctattat | tgcttattag | tactgtactg | taatcgtcat | 1260 |
| tagttgctgt | agggttgttc | aacttgctaa | tctgattctg | aactaccatg | ctgatgtccg | 1320 |
| aaataaagaa | aaagcatgtt | ttttttttgtg | tcaacttgca | aactttcttt | taaacattgt | 1380 |
| gcaatgtatt | gtaaatttct | ttatcaactt | ccctcgattc | agagagaagc | acttgtttgt | 1440 |
| aagtcatgaa | agattttttct | cgacaaaaaa | aaaaaaaaaa | aaaaaaa | | 1487 |

```
<210> SEQ ID NO 14
<211> LENGTH: 345
<212> TYPE: PRT
<213> ORGANISM: Triticum aestivum

<400> SEQUENCE: 14

Ser Trp Lys Glu Gly Gly Glu Ala Val Ser Thr Gly Ile Gly Gly
 1               5                  10                  15

Gly Trp Gln Leu Ala Trp Lys Trp Ser Glu Arg Gln Gly Glu Asp Gly
                 20                  25                  30

Lys Lys Glu Gly Gly Phe Lys Arg Ile Tyr Leu His Gln Glu Gly Val
             35                  40                  45

Ala Asp Ser Arg Arg Gly Ser Val Val Ser Leu Pro Gly Gly Gly Asp
         50                  55                  60

Ala Thr Gln Gly Gly Ser Gly Phe Ile His Ala Ala Leu Val Ser
 65                  70                  75                  80

His Ser Ala Leu Tyr Ser Lys Asp Leu Met Glu Glu Arg Met Ala Ala
                 85                  90                  95

Gly Pro Ala Met Ile His Pro Leu Glu Ala Ala Pro Lys Gly Ser Ile
            100                 105                 110

Trp Lys Asp Leu Phe Glu Pro Gly Val Arg Arg Ala Leu Phe Val Gly
        115                 120                 125

Val Gly Ile Gln Met Leu Gln Gln Phe Ala Gly Ile Asn Gly Val Leu
    130                 135                 140

Tyr Tyr Thr Pro Gln Ile Leu Glu Gln Ala Gly Val Ala Val Leu Leu
145                 150                 155                 160

Ser Asn Leu Gly Leu Ser Ser Ala Ser Ala Ser Ile Leu Ile Ser Ser
                165                 170                 175

Leu Thr Thr Leu Leu Met Leu Pro Ser Ile Gly Val Ala Met Arg Leu
            180                 185                 190

Met Asp Ile Ser Gly Arg Arg Phe Leu Leu Gly Thr Ile Pro Ile
        195                 200                 205

Leu Ile Ala Ser Leu Ile Val Leu Gly Val Val Asn Val Ile Asn Leu
    210                 215                 220

Ser Thr Val Pro His Ala Val Leu Ser Thr Val Ser Val Ile Val Tyr
225                 230                 235                 240

Phe Cys Cys Phe Val Met Gly Phe Gly Pro Ile Pro Asn Ile Leu Cys
                245                 250                 255

Ala Glu Ile Phe Pro Thr Arg Val Arg Gly Val Cys Ile Ala Ile Cys
            260                 265                 270

Ala Leu Thr Phe Trp Ile Cys Asp Ile Ile Val Thr Tyr Ser Leu Pro
        275                 280                 285

Val Met Leu Asn Ala Ile Gly Leu Ala Gly Val Phe Gly Ile Tyr Ala
    290                 295                 300

Val Val Cys Cys Ile Ala Phe Val Phe Val Tyr Leu Lys Val Pro Glu
305                 310                 315                 320

Thr Lys Gly Met Pro Leu Glu Val Ile Thr Glu Phe Phe Ala Val Gly
                325                 330                 335

Ala Lys Gln Ala Gln Ala Thr Ile Ala
            340                 345

<210> SEQ ID NO 15
<211> LENGTH: 1009
<212> TYPE: DNA
<213> ORGANISM: Triticum aestivum
```

<400> SEQUENCE: 15

```
tgaacctgga gtgaagcatg cactgttcgt tggcatagga ttacagatcc tgcagcagtt     60
tgcgggtatc aatggagtcc tctactacac acctcagata cttgagcaag caggtgtcgg    120
ggttcttcta tcaaacattg gactaagctc ttcctcagca tctattctta ttagtgcctt    180
gacaaccttg ctgatgcttc ccagcattgg catcgccatg agactcatgg atatgtcagg    240
aagaaggttt cttctccttt caacaatccc tgtcttgata gtagcgctag ctgtcttggt    300
tttagtgaat gttctggatg tcggaaccat ggtgcacgct gcgctctcaa cgatcagcgt    360
catcgtctat ttctgcttct tcgtcatggg gtttgggcct atcccaaata ttctctgcgc    420
ggagattttc cccacctctg tccgtggcat ctgcatagcc atctgcgcgc taaccttctg    480
gatcggcgac atcatcgtga catacactct ccccgtgatg ctcaatgcca ttggtctcgc    540
tggagtcttc ggcatatatg ccatcgtttg tgtactagcc tttgtattcg tctacatgaa    600
ggtccctgag acaaagggca tgcccctgga ggtcatcacc gagttcttct ctgtcggggc    660
aaagcagggc aaggaagcca cggactagtt gctctgatcc ggtgatccgc gtcgctggtg    720
gtaattttgt ggtgtcataa ctactactac actggttaac ctgcgatgct ttggtgaaga    780
aacttcaaag agagcagata cggaagactt tacatcgtga ggctgaattg tgtcgtcgta    840
ggccggcttt tggaagtagg atatgtactt agatcatctg ctcttttcgc tttgaacttt    900
tctatttgtg ttattcagaa tttcttgccc atgtaactag tgctgttatc acaatttatg    960
tcgattatgt gtttgcctaa aaaaaaaaaa aaaaaaaaaa aaaaaaaa                1009
```

<210> SEQ ID NO 16
<211> LENGTH: 228
<212> TYPE: PRT
<213> ORGANISM: Triticum aestivum

<400> SEQUENCE: 16

```
Glu Pro Gly Val Lys His Ala Leu Phe Val Gly Ile Gly Leu Gln Ile
  1               5                  10                  15

Leu Gln Gln Phe Ala Gly Ile Asn Gly Val Leu Tyr Tyr Thr Pro Gln
             20                  25                  30

Ile Leu Glu Gln Ala Gly Val Gly Val Leu Leu Ser Asn Ile Gly Leu
         35                  40                  45

Ser Ser Ser Ala Ser Ile Leu Ile Ser Ala Leu Thr Thr Leu Leu
     50                  55                  60

Met Leu Pro Ser Ile Gly Ile Ala Met Arg Leu Met Asp Met Ser Gly
 65                  70                  75                  80

Arg Arg Phe Leu Leu Leu Ser Thr Ile Pro Val Leu Ile Val Ala Leu
                 85                  90                  95

Ala Val Leu Val Leu Val Asn Val Leu Asp Val Gly Thr Met Val His
            100                 105                 110

Ala Ala Leu Ser Thr Ile Ser Val Ile Val Tyr Phe Cys Phe Phe Val
        115                 120                 125

Met Gly Phe Gly Pro Ile Pro Asn Ile Leu Cys Ala Glu Ile Phe Pro
    130                 135                 140

Thr Ser Val Arg Gly Ile Cys Ile Ala Ile Cys Ala Leu Thr Phe Trp
145                 150                 155                 160

Ile Gly Asp Ile Ile Val Thr Tyr Thr Leu Pro Val Met Leu Asn Ala
                165                 170                 175

Ile Gly Leu Ala Gly Val Phe Gly Ile Tyr Ala Ile Val Cys Val Leu
            180                 185                 190
```

Ala Phe Val Phe Val Tyr Met Lys Val Pro Glu Thr Lys Gly Met Pro
        195                 200                 205

Leu Glu Val Ile Thr Glu Phe Phe Ser Val Gly Ala Lys Gln Gly Lys
        210                 215                 220

Glu Ala Thr Asp
225

<210> SEQ ID NO 17
<211> LENGTH: 615
<212> TYPE: DNA
<213> ORGANISM: Zea mays
<220> FEATURE:
<221> NAME/KEY: unsure
<222> LOCATION: (149)
<221> NAME/KEY: unsure
<222> LOCATION: (271)
<221> NAME/KEY: unsure
<222> LOCATION: (304)
<221> NAME/KEY: unsure
<222> LOCATION: (334)
<221> NAME/KEY: unsure
<222> LOCATION: (357)
<221> NAME/KEY: unsure
<222> LOCATION: (476)
<221> NAME/KEY: unsure
<222> LOCATION: (599)
<221> NAME/KEY: unsure
<222> LOCATION: (602)

<400> SEQUENCE: 17
gaaacgaact ctcttgagta ccacaaaaaa aaacattggc attctctgta gtagagcaca      60
gagcgaaccg tcaacgatgg cttccgctcc gctgccggcg gccatcgagc ccgggaagaa     120
aggcaacgtc aagttcgcct tcgcctgcnc catcctcgcc tcaatgacct ccatccttct     180
cggctatgat atcggagtga tgagcggcgc gtcgttgtac atcaagaagg acctgaaaat     240
cagcgacgtg aagctggaga tcctgatggg natcctcaac gtgtactcgc tcatcggctc     300
gttngcggca gggcggacgt ccgactggat cggncgccgt acaccatcgt gttcgcngcg     360
gtgatcttct tcgcgggcgc ttcctcatgg gcttcgccgt gaactactgg atgctcatgt     420
tcgggcgctt cgtggccggg atcggcgtgg gctacgcgct catgatcgca accgtntaca     480
cggccgaagt gtccccgcat cggccgcgcg cttcctgacg tcgttcccgg aggtgttcat     540
cacttcggca tcctctaggt acgtgtcaat aaggcttttc cgcttccgtt cgctggatng     600
cnctaatgtc ggcat                                                     615

<210> SEQ ID NO 18
<211> LENGTH: 167
<212> TYPE: PRT
<213> ORGANISM: Zea mays
<220> FEATURE:
<221> NAME/KEY: UNSURE
<222> LOCATION: (34)
<221> NAME/KEY: UNSURE
<222> LOCATION: (85)
<221> NAME/KEY: UNSURE
<222> LOCATION: (98)
<221> NAME/KEY: UNSURE
<222> LOCATION: (112)
<221> NAME/KEY: UNSURE
<222> LOCATION: (151)

<400> SEQUENCE: 18

Ser Arg Ala Gln Ser Glu Pro Ser Thr Met Ala Ser Ala Pro Leu Pro
1               5                   10                  15

-continued

```
Ala Ala Ile Glu Pro Gly Lys Lys Gly Asn Val Lys Phe Ala Phe Ala
         20                  25                  30

Cys Xaa Ile Leu Ala Ser Met Thr Ser Ile Leu Leu Gly Tyr Asp Ile
             35                  40                  45

Gly Val Met Ser Gly Ala Ser Leu Tyr Ile Lys Lys Asp Leu Lys Ile
 50                  55                  60

Ser Asp Val Lys Leu Glu Ile Leu Met Gly Ile Leu Asn Val Tyr Ser
 65                  70                  75                  80

Leu Ile Gly Ser Xaa Ala Ala Gly Arg Thr Ser Asp Trp Ile Gly Arg
                 85                  90                  95

Arg Xaa Thr Ile Val Phe Ala Ala Val Ile Phe Ala Gly Ala Xaa
             100                 105                 110

Leu Met Gly Phe Ala Val Asn Tyr Trp Met Leu Met Phe Gly Arg Phe
             115                 120                 125

Val Ala Gly Ile Gly Val Gly Tyr Ala Leu Met Ile Ala Thr Val Tyr
 130                 135                 140

Thr Ala Glu Val Ser Pro Xaa Ser Ala Arg Gly Phe Leu Thr Ser Phe
 145                 150                 155                 160

Pro Glu Val Phe Ile Thr Ser
             165
```

<210> SEQ ID NO 19
<211> LENGTH: 1914
<212> TYPE: DNA
<213> ORGANISM: Zea mays

<400> SEQUENCE: 19

```
gcacgaggca cgccacctta tctctaaccg gagatcaaag aagtagccgt taacgatggc      60
ttccgacgag ctcgcaaagg ccgtcgagcc caggaagaag ggcaacgtca gtatgcctc     120
catatgtgcc atcctggcct ccatggcctc tgtcatcctt ggctatgaca ttggggtgat    180
gagtggagcg gccatgtaca tcaagaagga cctgaatatc acggacgtgc agctggagat    240
cctgatcggg atcctcagtc tctactcgct gttcggatcc ttcgctggcg cgcggacgtc    300
cgacaggatc gggcgccgct tgaccgtcgt gttcgccgct gtcatcttct tcgtgggctc    360
gttgctcatg ggttttcgcc gtcaactacg catgctcatg gcgggccgct tcgtggccgg    420
agtcggtgtg ggctacgggg gcatgatcgc gcccgtgtac acggccgaga tctcgcctgc    480
ggcgtcccgt ggcttcctga ccaccttccc ggaggtgttc atcaacatcg gcatcctgct    540
tggctacctg tccaacttcg cgttcgcgcg cctcccgctc cacctcggct ggcgcgtcat    600
gctcgccatt ggcgcagttc cgtccggcct gctcgcgctc ctggtgttct gcatgcccga    660
gtcgcctcgg tggctggtct tgaagggccg cctcgcggac gccagggctg tgctagagaa    720
gacctctgcc acgccagagg aggccgccga gcggctggcc gacatcaagg ccgcggcggg    780
gattccgaag ggcctcgacg gggacgtagt caccgtaccc ggcaaggagc aaggcggcgg    840
tgagttgcag gtgtggaaga agctcatcct gtccccgacc ccggctgtcc gacgcatact    900
gctctcggcc gtgggtctcc acttcttcca gcaggcttct ggcagcgact ccgtcgtcca    960
gtacagcgcc cgcctgttca gagcgcgggg gatcaccgac gacaacaagc tcctgggcgt   1020
cacctgcgcg gtgggcgtga ccaagacgtt cttcatcctg gtggccacgt tcctgctgga   1080
ccgcgcgggg cgtcggcctc tgctgctgat cagcacgggc gggatgattg tctcgctcat   1140
ctgcctcggg tcgggctca ccgtcgcggg gcatcacccg gacaccaagg tcgcgtgggc   1200
cgtcgccctg tgcatcgcgt caaccctgtc ctacatcgcc ttcttctcca tcggcctcgg   1260
```

```
gcccatcacg gccgtgtaca cctcggaaat attcccgctg caggtgcgcg cgctgggctt    1320
cgcggtgggt gtggcgagca accgcgtcac cagcgccgtc atctccatga ccttcctgtc    1380
cctctccaag gccatcacca tcggcggcag cttcttcctc tactccggca tcgccgcggt    1440
cgcttgggtt ttcttcttca cgtgcctccc ggagacacgc ggccggacgc tggaggagat    1500
gggcaagctg ttcggcatgc cagacacggg catggctgaa gaagcagaag acgccgcagc    1560
caaggagaag gtggtggaac tgcctagcag caagtaggtg gctatcccag agcacaggtc    1620
aagtgaagta gatggacaag atcattgtct tttcaactaa ttagatgggc aagaataact    1680
aagactgccc tatgaggtgt cgtggttcaa ccagagatca ttctgctcct tttcttttcc    1740
cttccttttt cgagtaccat tcccattcgt cgtggtcagt acgatgttgg gtcgttggga    1800
gttagtggtg tcagagtccg cgtgtgcttt gcaagccagg gctgaaccca caatcatcag    1860
taacaaaaat tcttccgttt gctttgcaag ccaaaaaaaa aaaaaaaaaa aaaa           1914
```

<210> SEQ ID NO 20
<211> LENGTH: 513
<212> TYPE: PRT
<213> ORGANISM: Zea mays

<400> SEQUENCE: 20

```
Met Ala Ser Asp Glu Leu Ala Lys Ala Val Glu Pro Arg Lys Lys Gly
  1               5                  10                  15

Asn Val Lys Tyr Ala Ser Ile Cys Ala Ile Leu Ala Ser Met Ala Ser
                 20                  25                  30

Val Ile Leu Gly Tyr Asp Ile Gly Val Met Ser Gly Ala Ala Met Tyr
             35                  40                  45

Ile Lys Lys Asp Leu Asn Ile Thr Asp Val Gln Leu Glu Ile Leu Ile
         50                  55                  60

Gly Ile Leu Ser Leu Tyr Ser Leu Phe Gly Ser Phe Ala Gly Ala Arg
 65                  70                  75                  80

Thr Ser Asp Arg Ile Gly Arg Arg Leu Thr Val Val Phe Ala Ala Val
                 85                  90                  95

Ile Phe Phe Val Gly Ser Leu Leu Met Gly Phe Ala Val Asn Tyr Gly
            100                 105                 110

Met Leu Met Ala Gly Arg Phe Val Ala Gly Val Gly Val Gly Tyr Gly
            115                 120                 125

Gly Met Ile Ala Pro Val Tyr Thr Ala Glu Ile Ser Pro Ala Ala Ser
        130                 135                 140

Arg Gly Phe Leu Thr Thr Phe Pro Glu Val Phe Ile Asn Ile Gly Ile
145                 150                 155                 160

Leu Leu Gly Tyr Leu Ser Asn Phe Ala Phe Ala Arg Leu Pro Leu His
                165                 170                 175

Leu Gly Trp Arg Val Met Leu Ala Ile Gly Ala Val Pro Ser Gly Leu
            180                 185                 190

Leu Ala Leu Leu Val Phe Cys Met Pro Glu Ser Pro Arg Trp Leu Val
        195                 200                 205

Leu Lys Gly Arg Leu Ala Asp Ala Arg Ala Val Leu Glu Lys Thr Ser
    210                 215                 220

Ala Thr Pro Glu Glu Ala Glu Arg Leu Asp Ile Lys Ala Ala
225                 230                 235                 240

Ala Gly Ile Pro Lys Gly Leu Asp Gly Asp Val Val Thr Val Pro Gly
                245                 250                 255
```

```
Lys Glu Gln Gly Gly Glu Leu Gln Val Trp Lys Lys Leu Ile Leu
            260                 265                 270
Ser Pro Thr Pro Ala Val Arg Arg Ile Leu Leu Ser Ala Val Gly Leu
        275                 280                 285
His Phe Phe Gln Gln Ala Ser Gly Ser Asp Ser Val Val Gln Tyr Ser
    290                 295                 300
Ala Arg Leu Phe Lys Ser Ala Gly Ile Thr Asp Asp Asn Lys Leu Leu
305                 310                 315                 320
Gly Val Thr Cys Ala Val Gly Val Thr Lys Thr Phe Phe Ile Leu Val
                325                 330                 335
Ala Thr Phe Leu Leu Asp Arg Ala Gly Arg Arg Pro Leu Leu Leu Ile
            340                 345                 350
Ser Thr Gly Gly Met Ile Val Ser Leu Ile Cys Leu Gly Ser Gly Leu
        355                 360                 365
Thr Val Ala Gly His His Pro Asp Thr Lys Val Ala Trp Ala Val Ala
    370                 375                 380
Leu Cys Ile Ala Ser Thr Leu Ser Tyr Ile Ala Phe Phe Ser Ile Gly
385                 390                 395                 400
Leu Gly Pro Ile Thr Gly Val Tyr Thr Ser Glu Ile Phe Pro Leu Gln
                405                 410                 415
Val Arg Ala Leu Gly Phe Ala Val Gly Val Ala Ser Asn Arg Val Thr
            420                 425                 430
Ser Ala Val Ile Ser Met Thr Phe Leu Ser Leu Ser Lys Ala Ile Thr
        435                 440                 445
Ile Gly Gly Ser Phe Phe Leu Tyr Ser Gly Ile Ala Ala Val Ala Trp
    450                 455                 460
Val Phe Phe Thr Cys Leu Pro Glu Thr Arg Gly Arg Thr Leu Glu
465                 470                 475                 480
Glu Met Gly Lys Leu Phe Gly Met Pro Asp Thr Gly Met Ala Glu Glu
                485                 490                 495
Ala Glu Asp Ala Ala Ala Lys Glu Lys Val Val Glu Leu Pro Ser Ser
            500                 505                 510
Lys
```

<210> SEQ ID NO 21
<211> LENGTH: 2017
<212> TYPE: DNA
<213> ORGANISM: Oryza sativa

<400> SEQUENCE: 21

| | | | | |
|---|---|---|---|---|
| cttacatgta agctcgtgcc ggcacgagct tacactcgac cgccactact gtacacggcc | 60 |
| cagagcgagc ctcctcctcc tctgcaccac cggagatggc ttccgccgcg ctgccggagg | 120 |
| ccgtcgcgcc gaagaagaag ggcaacgtcc ggttcgcctt cgcctgcgcc atcctcgcct | 180 |
| ccatgacctc catcctcctc ggctacgata tcggggtgat gagcggggcg tcgctgtaca | 240 |
| tcaagaagga cttcaacatc agtgacggga aggtggaggt tctcatgggc atactgaacc | 300 |
| tctactcgct catcggctcc ttcgcggcgg ggcggacgtc ggactggatc ggccggcggt | 360 |
| acaccatcgt gttcgccgcc gtcatattct tcgcgggggs gttcctcatg gggttcgccg | 420 |
| tcaactacgc catgctcatg ttcggccgct tcgtggccgg catcggcgtg ggctacgcgc | 480 |
| tcatgatcgc gccggtgtac accgccgagg tgtcgccggc gtcggcgcgt ggcttcctga | 540 |
| cgtcgttccc ggaggtgttc atcaacttcg gcatcctgct cgggtacgtc tcgaactatg | 600 |
| cttctctccg cttgccgctg aacctcgggt ggcgcatcat gctcggcatc ggcgcggcgc | 660 |

-continued

```
cgtccgtgct gctcgcgctc atggtgctcg gcatgccgga gtcgccgcgg tggctggtca       720
tgaagggacg cctcgcggac gccaaggtgg tgctggagaa gacctccgac acggcggagg       780
aggccgcgga gcgcctggcc gacatcaagg ccgccgccgg catccctgag gagctcgacg       840
gcgacgtggt gaccgtcccc aagagaggga gcggaaacga gaagcgggtg tggaaggagc       900
tcatcctgtc cccgaccccg gccatgcggc gcatcctgct gtccgggatc ggcatccact       960
tcttccagca tgcgttgggc attcactccg tcgtcttcta cagccctctc gtgttcaaga      1020
gccccggatt aacgaacgac aaacacttct tgggcaccac ttggccgttc ggtgtcacca      1080
agaggctttt catcttgttg gcgactttct tcatcgacgg cgtcgggcgg cggccgctgt      1140
tgctgggcag cacgggcggg ataatcctct ccctcatcgg cctcggcgcc gggctcaccg      1200
tcgtcggcca gcaccccgac gccaagatac cttgggccat cggcctaagc atcgcctcca      1260
ccctcgccta cgtcgccttc ttctccatcg gccttggccc catcacgtgg gtgtacagct      1320
cggagatctt cccgctccag gtgcgcgcgc tgggctgctc gctcggcgtc gccgccaacc      1380
gcgtcaccag cggcgtcatc tccatgacct cctgtcgct gtccaaggcc atcaccatcg      1440
gcggcagctt cttcctctac tccggcatcg ccgcgctcgc ctgggtgttc ttctacacct      1500 acctccccgga acccgcggc cggacgctgg aggagatgag caagctgttc ggcgacacgg      1560
ccgccgcctc ggaatcagac gagccagcca aggagaagaa gaaggtggaa atggccgcca      1620
ctaactgatc aaactaaccg caaaatcacc aaatcctaag ggttttcttg caaaaacgtg      1680
tgctgtactg gctagctagc aagtagtagc agcaacgtgg gaagattcgc tgatccggcg      1740
ttgctggaga gcgacggccg gcgacgacaa agctgagctc cagctcgaga cttcttaaaa      1800
tcatcttcaa gtacatggat tttattttgc tctttgcttt gtccgtaaaa gttgtactat      1860
gcgatgaaga ataccagtat gtagcaaggc tgaggttgtg tgtagctact agaagtgtca      1920
gtcacgttgt tcttgtaaga aatgtttaac tgttaattaa gcagtattgt tgcagtaatc      1980
aaaaaaaaaa aaaaaaaaaa aaaaaaaaaa aaaaaaa                               2017
```

<210> SEQ ID NO 22
<211> LENGTH: 510
<212> TYPE: PRT
<213> ORGANISM: Oryza sativa
<220> FEATURE:
<221> NAME/KEY: UNSURE
<222> LOCATION: (102)

<400> SEQUENCE: 22

```
Met Ala Ser Ala Ala Leu Pro Glu Ala Val Ala Pro Lys Lys Lys Gly
 1               5                  10                  15

Asn Val Arg Phe Ala Phe Ala Cys Ala Ile Leu Ala Ser Met Thr Ser
            20                  25                  30

Ile Leu Leu Gly Tyr Asp Ile Gly Val Met Ser Gly Ala Ser Leu Tyr
        35                  40                  45

Ile Lys Lys Asp Phe Asn Ile Ser Asp Gly Lys Val Glu Val Leu Met
    50                  55                  60

Gly Ile Leu Asn Leu Tyr Ser Leu Ile Gly Ser Phe Ala Ala Gly Arg
65                  70                  75                  80

Thr Ser Asp Trp Ile Gly Arg Arg Tyr Thr Ile Val Phe Ala Ala Val
                85                  90                  95

Ile Phe Phe Ala Gly Xaa Phe Leu Met Gly Phe Ala Val Asn Tyr Ala
            100                 105                 110
```

```
Met Leu Met Phe Gly Arg Phe Val Ala Gly Ile Gly Val Gly Tyr Ala
        115                 120                 125
Leu Met Ile Ala Pro Val Tyr Thr Ala Glu Val Ser Pro Ala Ser Ala
    130                 135                 140
Arg Gly Phe Leu Thr Ser Phe Pro Glu Val Phe Ile Asn Phe Gly Ile
145                 150                 155                 160
Leu Leu Gly Tyr Val Ser Asn Tyr Ala Phe Ser Arg Leu Pro Leu Asn
                165                 170                 175
Leu Gly Trp Arg Ile Met Leu Gly Ile Gly Ala Ala Pro Ser Val Leu
            180                 185                 190
Leu Ala Leu Met Val Leu Gly Met Pro Glu Ser Pro Arg Trp Leu Val
        195                 200                 205
Met Lys Gly Arg Leu Ala Asp Ala Lys Val Val Leu Glu Lys Thr Ser
    210                 215                 220
Asp Thr Ala Glu Glu Ala Ala Glu Arg Leu Ala Asp Ile Lys Ala Ala
225                 230                 235                 240
Ala Gly Ile Pro Glu Glu Leu Asp Gly Asp Val Val Thr Val Pro Lys
                245                 250                 255
Arg Gly Ser Gly Asn Glu Lys Arg Val Trp Lys Glu Leu Ile Leu Ser
            260                 265                 270
Pro Thr Pro Ala Met Arg Arg Ile Leu Leu Ser Gly Ile Gly Ile His
        275                 280                 285
Phe Phe Gln His Ala Leu Gly Ile His Ser Val Val Phe Tyr Ser Pro
    290                 295                 300
Leu Val Phe Lys Ser Pro Gly Leu Thr Asn Asp Lys His Phe Leu Gly
305                 310                 315                 320
Thr Thr Trp Pro Phe Gly Val Thr Lys Arg Leu Phe Ile Leu Leu Ala
                325                 330                 335
Thr Phe Phe Ile Asp Gly Val Gly Arg Arg Pro Leu Leu Leu Gly Ser
            340                 345                 350
Thr Gly Gly Ile Ile Leu Ser Leu Ile Gly Leu Gly Ala Gly Leu Thr
        355                 360                 365
Val Val Gly Gln His Pro Asp Ala Lys Ile Pro Trp Ala Ile Gly Leu
    370                 375                 380
Ser Ile Ala Ser Thr Leu Ala Tyr Val Ala Phe Phe Ser Ile Gly Leu
385                 390                 395                 400
Gly Pro Ile Thr Trp Val Tyr Ser Ser Glu Ile Phe Pro Leu Gln Val
                405                 410                 415
Arg Ala Leu Gly Cys Ser Leu Gly Val Ala Ala Asn Arg Val Thr Ser
            420                 425                 430
Gly Val Ile Ser Met Thr Phe Leu Ser Leu Ser Lys Ala Ile Thr Ile
        435                 440                 445
Gly Gly Ser Phe Phe Leu Tyr Ser Gly Ile Ala Ala Leu Ala Trp Val
    450                 455                 460
Phe Phe Tyr Thr Tyr Leu Pro Glu Thr Arg Gly Arg Thr Leu Glu Glu
465                 470                 475                 480
Met Ser Lys Leu Phe Gly Asp Thr Ala Ala Ala Ser Glu Ser Asp Glu
                485                 490                 495
Pro Ala Lys Glu Lys Lys Val Glu Met Ala Ala Thr Asn
            500                 505                 510

<210> SEQ ID NO 23
<211> LENGTH: 1853
<212> TYPE: DNA
```

<213> ORGANISM: Glycine max

<400> SEQUENCE: 23

```
gcacgagagt ttctctcttc acatatcatc atacttagat agtcagatac atcacccaat    60
aattaaatta atacatgct agcactttaa cagtactcct ttctctaata tctctctcat   120
attttccttt ctgcggatat tcagctaatt aaactaagtc actaagatga ctgagggaaa   180
gctagttgaa gctgcagaag ctcataagac acttcaggat ttcgatcctc caaagaagcg   240
caaaaggaac aagtatgctt ttgcttgtgc tatgctggcc tccatgactt ccatcttgct   300
tggttatgat attggagtga tgagtggagc agccatatac ataaaaaggg acctgaaagt   360
ctcggacgag caaatcgaga tcctgctcgg aatcatcaac ctatactctc tgataggctc   420
atgtctcgcc ggcagaacct ccgactggat aggtccccgt tacacgattg ttttcgccgg   480
caccatcttc tttgtcggag cacttctcat gggtttctcc cccaattatt cctttctcat   540
gtttggccgt tcgtcgctg gcattggcat cggctacgcc ctcatgatag cccccgtcta   600
caccgccgag gtctccccgg cctcctctcg tggcttcctc acttccttcc ctgaggtatt   660
tattaatgga gggatattaa ttggatacat atcaaactat gcattttcga agctgacact   720
aaaggtggga tggcgaatga tgcttggagt tggtgcaata ccttcggtac tcctaacagt   780
aggagtgttg gcgatgccgg agtccccaag gtggcttgtg atgagggtc gtttgggaga   840
ggcaagaaaa gtgcttaaca aaacctcaga cagcaaggaa gaggcccaac taaggctagc   900
ggaaatcaaa caagccgcag ggatccccga gagttgcaac gacgacgtcg ttcaggtaaa   960
taaacaaagc aacggtgaag gtgtatggaa agagctcttc ctctatccaa cgcccgcaat  1020
tcgtcacatc gtaatcgctg cccttggtat tcacttcttc caacaagcgt cgggcgtaga  1080
cgccgtcgtt ttgtacagcc ccaggatctt cgaaaaggct gggattacaa acgacacgca  1140
taagcttctt gcaaccgtgg ccgttggatt cgttaagacc gtgttcatct ggcggctac  1200
gtttacgttg gaccgcgtgg gtcgtcgtcc gttgttattg tctagtgtcg gcggcatggt  1260
gctctcgctt ctcacgcttg cgatcagcct cactgttatt gatcattcgg agaggaaatt  1320
aatgtgggcc gttggatcga gcatagccat ggtgttggct tacgtggcca cgttctccat  1380
cggtgcgggt cccatcacgt gggtctatag ttctgagatc ttcccgttga ggctgcgggc  1440
gcarggtgcg gccgcgggag ttgcggtgaa taggaccact agcgcggttg tctcaatgac  1500
ttttctgtcc ctcactagag ccatcactat tggtggagct ttcttccttt attgtggcat  1560
tgctactgtt gggtggatat tcttttacac cgtcttgcct gagacccggg gaaaaacgct  1620
cgaagacatg gaagggtctt ttggtacttt taggtccaaa tccaacgcca gcaaggctgt  1680
agaaaatgag aatgggcaag tagcacaagt ccagctagga accaatgtcc aaacttgaaa  1740
aatgagtatt gggacatcca gtaatagtga agtaatttcg tgatttttt tttgtttttt  1800
acttttaga ctagttcttc aaatcaaaac gagaagttaa agtgaaaaaa aaa          1853
```

<210> SEQ ID NO 24
<211> LENGTH: 523
<212> TYPE: PRT
<213> ORGANISM: Glycine max

<400> SEQUENCE: 24

```
Met Thr Glu Gly Lys Leu Val Glu Ala Ala Glu Ala His Lys Thr Leu
 1               5                  10                  15

Gln Asp Phe Asp Pro Pro Lys Lys Arg Lys Arg Asn Lys Tyr Ala Phe
            20                  25                  30
```

```
Ala Cys Ala Met Leu Ala Ser Met Thr Ser Ile Leu Leu Gly Tyr Asp
         35                  40                  45

Ile Gly Val Met Ser Gly Ala Ala Ile Tyr Ile Lys Arg Asp Leu Lys
         50                  55                  60

Val Ser Asp Glu Gln Ile Glu Ile Leu Leu Gly Ile Ile Asn Leu Tyr
65                  70                  75                  80

Ser Leu Ile Gly Ser Cys Leu Ala Gly Arg Thr Ser Asp Trp Ile Gly
                 85                  90                  95

Pro Arg Tyr Thr Ile Val Phe Ala Gly Thr Ile Phe Val Gly Ala
                100                 105                 110

Leu Leu Met Gly Phe Ser Pro Asn Tyr Ser Phe Leu Met Phe Gly Arg
            115                 120                 125

Phe Val Ala Gly Ile Gly Ile Gly Tyr Ala Leu Met Ile Ala Pro Val
            130                 135                 140

Tyr Thr Ala Glu Val Ser Pro Ala Ser Ser Arg Gly Phe Leu Thr Ser
145                 150                 155                 160

Phe Pro Glu Val Phe Ile Asn Gly Gly Ile Leu Ile Gly Tyr Ile Ser
                    165                 170                 175

Asn Tyr Ala Phe Ser Lys Leu Thr Leu Lys Val Gly Trp Arg Met Met
            180                 185                 190

Leu Gly Val Gly Ala Ile Pro Ser Val Leu Leu Thr Val Gly Val Leu
            195                 200                 205

Ala Met Pro Glu Ser Pro Arg Trp Leu Val Met Arg Gly Arg Leu Gly
            210                 215                 220

Glu Ala Arg Lys Val Leu Asn Lys Thr Ser Asp Ser Lys Glu Glu Ala
225                 230                 235                 240

Gln Leu Arg Leu Ala Glu Ile Lys Gln Ala Ala Gly Ile Pro Glu Ser
                    245                 250                 255

Cys Asn Asp Asp Val Val Gln Val Asn Lys Gln Ser Asn Gly Glu Gly
                    260                 265                 270

Val Trp Lys Glu Leu Phe Leu Tyr Pro Thr Pro Ala Ile Arg His Ile
            275                 280                 285

Val Ile Ala Ala Leu Gly Ile His Phe Phe Gln Gln Ala Ser Gly Val
290                 295                 300

Asp Ala Val Val Leu Tyr Ser Pro Arg Ile Phe Glu Lys Ala Gly Ile
305                 310                 315                 320

Thr Asn Asp Thr His Lys Leu Leu Ala Thr Val Ala Val Gly Phe Val
                    325                 330                 335

Lys Thr Val Phe Ile Leu Ala Ala Thr Phe Thr Leu Asp Arg Val Gly
                340                 345                 350

Arg Arg Pro Leu Leu Leu Ser Ser Val Gly Gly Met Val Leu Ser Leu
            355                 360                 365

Leu Thr Leu Ala Ile Ser Leu Thr Val Ile Asp His Ser Glu Arg Lys
            370                 375                 380

Leu Met Trp Ala Val Gly Ser Ser Ile Ala Met Val Leu Ala Tyr Val
385                 390                 395                 400

Ala Thr Phe Ser Ile Gly Ala Gly Pro Ile Thr Trp Val Tyr Ser Ser
                405                 410                 415

Glu Ile Phe Pro Leu Arg Leu Arg Ala Gln Gly Ala Ala Gly Val
                420                 425                 430

Ala Val Asn Arg Thr Thr Ser Ala Val Val Ser Met Thr Phe Leu Ser
            435                 440                 445
```

```
Leu Thr Arg Ala Ile Thr Ile Gly Gly Ala Phe Phe Leu Tyr Cys Gly
        450                 455                 460

Ile Ala Thr Val Gly Trp Ile Phe Phe Tyr Thr Val Leu Pro Glu Thr
465                 470                 475                 480

Arg Gly Lys Thr Leu Glu Asp Met Glu Gly Ser Phe Gly Thr Phe Arg
                485                 490                 495

Ser Lys Ser Asn Ala Ser Lys Ala Val Glu Asn Glu Asn Gly Gln Val
            500                 505                 510

Ala Gln Val Gln Leu Gly Thr Asn Val Gln Thr
            515                 520

<210> SEQ ID NO 25
<211> LENGTH: 2089
<212> TYPE: DNA
<213> ORGANISM: Triticum aestivum

<400> SEQUENCE: 25
agcaccacta aactatacac aaggaggacc tcgtcggcat aatcctcagg cagcgagcag      60
aggggcgtcg tcgacgatgg accgcgccgc actcccggcg gccgtcgagc caagaagaa     120 gggcaacgtg aggttcgcct tcgcctgcgc catcctcgcc tccatgacct ccatcctcct     180
cggctacgac atcggcgtga tgagcggagc gtcgctgtac atccagaagg atctgaagat     240
caacgacacc cagctggagg tcctcatggg catcctcaac gtgtactcgc tcattggctc     300
cttcgcggcg gggcggacgt ccgactggat cggccggcgc ttcaccatcg tcttcgccgc     360
cgtcatcttc ttcgcgggcg ccctcatcat gggcttctcc gtcaactacg ccatgctcat     420
gttcgggcgc ttcgtggccg catcggcgt ggggtacgct ctcatgatcg cgcccgtgaa     480
cacgggcgag gtgtcccccg cgtctgcccg tgggggttctc acatccttcc ggaggtgtt     540 catcaacttc ggcatcctcc tcggatatgt ctccaacttc gccttcgccc gcctctccct     600
ccgcctcggc tggcgcatta tgctcggcat aggcgcggtg ccgtccgtcc tgctcgcgtt     660
catggtgctc ggcatgcccg agtctccccg gtggctcgtc atgaagggcc gtctcgcgga     720
cgccaaggtt gtgcttgcca agacgtccga cacgccggaa gaggccgccg agcgcatcgc     780
cgacattaag actgccgccg gcatccctct gggcctcgac ggcgacgtgg tccccgtgcc     840
caaaaacaaa ggaagcagcg aggagaagcg cgtttttgaag gacctcatcc tgtcaccgac     900
catagccatg cgccacatcc tcatcgcggg aatcggcatc cacttcttcc agcagtcttc     960
gggcatcgac gccgtcgtgc tctacagccc gctagttttc aagagcgccg gcatcacggg    1020
cgacagccgt ctccgcggca ccaccgtggc ggtcggggcc accaatacgg tcttcatcct    1080
ggtggccacc ttcctcctcg accgcatccg cggcggccg ctggtgctga ccagcacggg    1140
cggcatgctc gtctccttag tgggcctcgc gacgggctc accgtcatca gccgccaccc    1200
ggacgagaag atcacctggg ccatcgtcct gtgcatcttc tgcatcatgg cctacgtggc    1260
cttcttctcc atcggcctcg gccccatcac gtgggtgtac agctcggaga tcttcccgct    1320
gcacgtgcgc gcgctgggct gctccctggg cgtggccgtc aaccgcctga ccagcggcgt    1380
gatctccatg accttcattt cgctgtccaa ggccatgacc atcggcggcg ccttcttcct    1440
cttcgccggc atcgcctcat tcgcatgggt gttcttcttc gcctacctgc cggagacccg    1500
cggccgcacg ctggaggaca tgagctcgct gttcggcaac acggcacgc acaagcaggg    1560 cgccgcggaa gccgacgacg acgccgggga agaaggtg gaaatggccg ccaccaactg    1620
accgcaagtt ggcagatcgc gatgcgaaga cttcgcgctgt atccgtctcg gctagctagc    1680
```

-continued

```
tgccacaagg ccacatagat gacgaagtag cgtgggaaga ttcgctgatc cggccggagc    1740
tgccggaggg cgacggcaag ctccagctcg atcgagacgt taatggcttc ttaaatgtgc    1800
taagtttaat gtttcgctct ttggttttgt ccgggtaggt cgtgagcaat ccggtagtgc    1860
cgatgccaag gctaatcgac gccggacgga ctagactact gtagtagact gtagaggtgt    1920
accgttgcta cttccgtggc gtttgtctgc atgattagga gagaaactg gcggtggttc     1980 gaggactcta cctgccgatc gagtgagtca agcgagccac ggaaaatgtg taagaaaaaa    2040
atattaagta tgtgtattgt aaaaaaaaaa aaaaaaaaaa aaaaaaaa                 2089
```

<210> SEQ ID NO 26
<211> LENGTH: 539
<212> TYPE: PRT
<213> ORGANISM: Triticum aestivum

<400> SEQUENCE: 26

```
Ala Pro Leu Asn Tyr Thr Gln Gly Gly Pro Arg Arg His Asn Pro Gln
  1               5                  10                  15

Ala Ala Ser Arg Gly Ala Ser Ser Thr Met Asp Arg Ala Ala Leu Pro
             20                  25                  30

Ala Ala Val Glu Pro Lys Lys Lys Gly Asn Val Arg Phe Ala Phe Ala
         35                  40                  45

Cys Ala Ile Leu Ala Ser Met Thr Ser Ile Leu Leu Gly Tyr Asp Ile
     50                  55                  60

Gly Val Met Ser Gly Ala Ser Leu Tyr Ile Gln Lys Asp Leu Lys Ile
 65                  70                  75                  80

Asn Asp Thr Gln Leu Glu Val Leu Met Gly Ile Leu Asn Val Tyr Ser
                 85                  90                  95

Leu Ile Gly Ser Phe Ala Ala Gly Arg Thr Ser Asp Trp Ile Gly Arg
            100                 105                 110

Arg Phe Thr Ile Val Phe Ala Ala Val Ile Phe Phe Ala Gly Ala Leu
        115                 120                 125

Ile Met Gly Phe Ser Val Asn Tyr Ala Met Leu Met Phe Gly Arg Phe
    130                 135                 140

Val Ala Gly Ile Gly Val Gly Tyr Ala Leu Met Ile Ala Pro Val Asn
145                 150                 155                 160

Thr Gly Glu Val Ser Pro Ala Ser Ala Arg Gly Val Leu Thr Ser Phe
                165                 170                 175

Pro Glu Val Phe Ile Asn Phe Gly Ile Leu Leu Gly Tyr Val Ser Asn
            180                 185                 190

Phe Ala Phe Ala Arg Leu Ser Leu Arg Leu Gly Trp Arg Ile Met Leu
        195                 200                 205

Gly Ile Gly Ala Val Pro Ser Val Leu Leu Ala Phe Met Val Leu Gly
    210                 215                 220

Met Pro Glu Ser Pro Arg Trp Leu Val Met Lys Gly Arg Leu Ala Asp
225                 230                 235                 240

Ala Lys Val Val Leu Ala Lys Thr Ser Asp Thr Pro Glu Glu Ala Ala
                245                 250                 255

Glu Arg Ile Ala Asp Ile Lys Thr Ala Ala Gly Ile Pro Leu Gly Leu
            260                 265                 270

Asp Gly Asp Val Val Pro Val Pro Lys Asn Lys Gly Ser Ser Glu Glu
        275                 280                 285

Lys Arg Val Leu Lys Asp Leu Ile Leu Ser Pro Thr Ile Ala Met Arg
    290                 295                 300
```

-continued

```
His Ile Leu Ile Ala Gly Ile Gly Ile His Phe Phe Gln Gln Ser Ser
305                 310                 315                 320

Gly Ile Asp Ala Val Val Leu Tyr Ser Pro Leu Val Phe Lys Ser Ala
            325                 330                 335

Gly Ile Thr Gly Asp Ser Arg Leu Arg Gly Thr Thr Val Ala Val Gly
            340                 345                 350

Ala Thr Asn Thr Val Phe Ile Leu Val Ala Thr Phe Leu Leu Asp Arg
        355                 360                 365

Ile Arg Arg Arg Pro Leu Val Leu Thr Ser Thr Gly Met Leu Val
370                 375                 380

Ser Leu Val Gly Leu Ala Thr Gly Leu Thr Val Ile Ser Arg His Pro
385                 390                 395                 400

Asp Glu Lys Ile Thr Trp Ala Ile Val Leu Cys Ile Phe Cys Ile Met
                405                 410                 415

Ala Tyr Val Ala Phe Phe Ser Ile Gly Leu Gly Pro Ile Thr Trp Val
            420                 425                 430

Tyr Ser Ser Glu Ile Phe Pro Leu His Val Arg Ala Leu Gly Cys Ser
        435                 440                 445

Leu Gly Val Ala Val Asn Arg Leu Thr Ser Gly Val Ile Ser Met Thr
    450                 455                 460

Phe Ile Ser Leu Ser Lys Ala Met Thr Ile Gly Gly Ala Phe Leu
465                 470                 475                 480

Phe Ala Gly Ile Ala Ser Phe Ala Trp Val Phe Phe Ala Tyr Leu
            485                 490                 495

Pro Glu Thr Arg Gly Arg Thr Leu Glu Asp Met Ser Ser Leu Phe Gly
        500                 505                 510

Asn Thr Ala Thr His Lys Gln Gly Ala Ala Glu Ala Asp Asp Ala
    515                 520                 525

Gly Glu Lys Lys Val Glu Met Ala Ala Thr Asn
530                 535
```

<210> SEQ ID NO 27
<211> LENGTH: 1872
<212> TYPE: DNA
<213> ORGANISM: Triticum aestivum

<400> SEQUENCE: 27

```
gcacgagctc atcactaggc tgtcagtctg tctgttcaac gaacgatcag ttcgtcctaa    60
gcagatgaaa atgtctccgg aaagaaaagg agcggaggac aaggaagaag gatcgaggat   120
ggcttctgct gcgctcccgg agccgggggc agtccatcca aggaacaagg caatttcaa    180
gtacgccttc acctgcgccc tctgtgcttc catggccacc atcgtcctcg gctacgacgt   240
tggggtgatg agcggtgcgt cgctgtacat caagagggac ctgcagatca cggacgtgca   300
gctggagatc atgatgggca tcctgagcgt gtacgcgctc atcgggtcct tcctcggcgc   360
gaggacgtcc gactgggtcg ccgccgcgt caccgtcgtc ttcgcggccg ccatcttcaa   420
caacggctcc ttgctcatgg gcttcgcggt caactacgcc atgctcatgg tcgggcgctt   480
cgtcaccgga atcggcgtgg gctacgccat catggtcgcg ccagtgtaca cgcccgaggt   540
gtccccggcg tcggcccgcg gcttcctcac gtctttcacc gaggtgttca tcaatgtggg   600
catcctcctt ggctacgtct ccaactacgc cttcgcgcgc ctcccgctcc acctcagctg   660
gcgcgtcatg ctcggcatcg gcgccgtccc gtccgccctg cttgcgctca tggtgttcgg   720
catgccggag tctcctcgct ggctcgtcat gaaaggccgc ctcgcggacg ccagggccgt   780
```

```
tctggccaag acctccgaca cgccggagga ggccgtggag cgccttgacc agatcaaggc    840
tgccgccggc atccctaggg aacttgacgg cgacgtggtc gtcatgccta agacaaaagg    900
cggccaggag aagcaggtgt ggaaggagct catcttttcg ccgacccag ccatgcggcg     960
catactgctc gcggcgctcg gcatccattt ctttcagcag gcgacgggct ccgactccgt   1020
cgtgctctat agcccacgcg tgttccagag cgcgggcatc accggcgaca accacctgct   1080
cggcgccaca tgcgccatgg gggtcatgaa gacgctcttc atcctggtgg ccacgttcca   1140
gctcgaccgc gtcggcaggc ggccgctgct gctgaccagc acggccggca tgctcgcctg   1200
tctcatcggc ctcgggacgg gcctcaccgt cgtgggtcgg cacccggacg ccaaggtccc   1260
gtgggccatc ggcctgtgca tcgtgtccat cttggcctac gtgtccttct ctccatcgg    1320
cctcgggccc ctcaccagcg tgtacacctc ggaggtcttc ccactgcggg tgcgcgcgct   1380
gggcttcgcg ctgggcacgt catgcaaccg cgtcaccagc gccgcggtct ccatgtcctt   1440
cctgtccttg tccaaggcca tcaccatcgg cggcagcttc ttcctgtacg ccggcatcgc   1500
ggcgatagga tggattttct tcttcacctt cattccggag acgcgtggcc tgccgctcga   1560
ggagataggg aagcttttcg gcatgacgga cacggccgtc gaagcccaag acaccgccac   1620
gaaagacaag gcgaaagtag gggagatgaa ctagtgagct agacgtcaac caactgttac   1680
cgatgtacta ccatagagat gtatctgatc aacgtggcaa tataagtgtc acggactctt   1740
ggtgctcatt gatggattgt ttggataaaa tttcaagaga attgtttcaa gtttggatcc   1800
aaaaaaaaaa aaaaaaaaaa aaaaaaaaaa aaaaaaaaaa aaaaaaaaaa aaaaaaaaaa   1860
aaaaaaaaaa aa                                                      1872
```

<210> SEQ ID NO 28
<211> LENGTH: 529
<212> TYPE: PRT
<213> ORGANISM: Triticum aestivum

<400> SEQUENCE: 28

```
Met Lys Met Ser Pro Glu Arg Lys Gly Ala Glu Asp Lys Glu Glu Gly
 1               5                  10                  15

Ser Arg Met Ala Ser Ala Ala Leu Pro Glu Pro Gly Ala Val His Pro
            20                  25                  30

Arg Asn Lys Gly Asn Phe Lys Tyr Ala Phe Thr Cys Ala Leu Cys Ala
        35                  40                  45

Ser Met Ala Thr Ile Val Leu Gly Tyr Asp Val Gly Val Met Ser Gly
    50                  55                  60

Ala Ser Leu Tyr Ile Lys Arg Asp Leu Gln Ile Thr Asp Val Gln Leu
65                  70                  75                  80

Glu Ile Met Met Gly Ile Leu Ser Val Tyr Ala Leu Ile Gly Ser Phe
                85                  90                  95

Leu Gly Ala Arg Thr Ser Asp Trp Val Gly Arg Val Thr Val Val
            100                 105                 110

Phe Ala Ala Ala Ile Phe Asn Asn Gly Ser Leu Leu Met Gly Phe Ala
        115                 120                 125

Val Asn Tyr Ala Met Leu Met Val Gly Arg Phe Val Thr Gly Ile Gly
    130                 135                 140

Val Gly Tyr Ala Ile Met Val Ala Pro Val Tyr Thr Pro Glu Val Ser
145                 150                 155                 160

Pro Ala Ser Ala Arg Gly Phe Leu Thr Ser Phe Thr Glu Val Phe Ile
                165                 170                 175
```

```
Asn Val Gly Ile Leu Leu Gly Tyr Val Ser Asn Tyr Ala Phe Ala Arg
            180                 185                 190

Leu Pro Leu His Leu Ser Trp Arg Val Met Leu Gly Ile Gly Ala Val
        195                 200                 205

Pro Ser Ala Leu Leu Ala Leu Met Val Phe Gly Met Pro Glu Ser Pro
    210                 215                 220

Arg Trp Leu Val Met Lys Gly Arg Leu Ala Asp Ala Arg Ala Val Leu
225                 230                 235                 240

Ala Lys Thr Ser Asp Thr Pro Glu Glu Ala Val Glu Arg Leu Asp Gln
                245                 250                 255

Ile Lys Ala Ala Ala Gly Ile Pro Arg Glu Leu Asp Gly Asp Val Val
                260                 265                 270

Val Met Pro Lys Thr Lys Gly Gly Gln Glu Lys Gln Val Trp Lys Glu
            275                 280                 285

Leu Ile Phe Ser Pro Thr Pro Ala Met Arg Arg Ile Leu Leu Ala Ala
    290                 295                 300

Leu Gly Ile His Phe Phe Gln Gln Ala Thr Gly Ser Asp Ser Val Val
305                 310                 315                 320

Leu Tyr Ser Pro Arg Val Phe Gln Ser Ala Gly Ile Thr Gly Asp Asn
                325                 330                 335

His Leu Leu Gly Ala Thr Cys Ala Met Gly Val Met Lys Thr Leu Phe
                340                 345                 350

Ile Leu Val Ala Thr Phe Gln Leu Asp Arg Val Gly Arg Arg Pro Leu
            355                 360                 365

Leu Leu Thr Ser Thr Ala Gly Met Leu Ala Cys Leu Ile Gly Leu Gly
    370                 375                 380

Thr Gly Leu Thr Val Val Gly Arg His Pro Asp Ala Lys Val Pro Trp
385                 390                 395                 400

Ala Ile Gly Leu Cys Ile Val Ser Ile Leu Ala Tyr Val Ser Phe Phe
                405                 410                 415

Ser Ile Gly Leu Gly Pro Leu Thr Ser Val Tyr Thr Ser Glu Val Phe
                420                 425                 430

Pro Leu Arg Val Arg Ala Leu Gly Phe Ala Leu Gly Thr Ser Cys Asn
            435                 440                 445

Arg Val Thr Ser Ala Ala Val Ser Met Ser Phe Leu Ser Leu Ser Lys
450                 455                 460

Ala Ile Thr Ile Gly Gly Ser Phe Phe Leu Tyr Ala Gly Ile Ala Ala
465                 470                 475                 480

Ile Gly Trp Ile Phe Phe Thr Phe Ile Pro Glu Thr Arg Gly Leu
                485                 490                 495

Pro Leu Glu Glu Ile Gly Lys Leu Phe Gly Met Thr Asp Thr Ala Val
            500                 505                 510

Glu Ala Gln Asp Thr Ala Thr Lys Asp Lys Ala Lys Val Gly Glu Met
        515                 520                 525

Asn

<210> SEQ ID NO 29
<211> LENGTH: 729
<212> TYPE: PRT
<213> ORGANISM: Arabidopsis thaliana

<400> SEQUENCE: 29

Met Ser Gly Ala Val Leu Val Ala Ile Ala Ala Val Gly Asn Leu
  1               5                  10                 15
```

-continued

```
Leu Gln Gly Trp Asp Asn Ala Thr Ile Ala Gly Ala Val Leu Tyr Ile
            20                  25                  30

Lys Lys Glu Phe Asn Leu Glu Ser Asn Pro Ser Val Glu Gly Leu Ile
            35                  40                  45

Val Ala Met Ser Leu Ile Gly Ala Thr Leu Ile Thr Thr Cys Ser Gly
            50                  55                  60

Gly Val Ala Asp Trp Leu Gly Arg Arg Pro Met Leu Ile Leu Ser Ser
 65                  70                  75                  80

Ile Leu Tyr Phe Val Gly Ser Leu Val Met Leu Trp Ser Pro Asn Val
                85                  90                  95

Tyr Val Leu Leu Leu Gly Arg Leu Leu Asp Gly Phe Gly Val Gly Leu
            100                 105                 110

Val Val Thr Leu Val Pro Ile Tyr Ile Ser Glu Thr Ala Pro Pro Glu
            115                 120                 125

Ile Arg Gly Leu Leu Asn Thr Leu Pro Gln Phe Thr Gly Ser Gly Gly
 130                 135                 140

Met Phe Leu Ser Tyr Cys Met Val Phe Gly Met Ser Leu Met Pro Ser
145                 150                 155                 160

Pro Ser Trp Arg Leu Met Leu Gly Val Leu Phe Ile Pro Ser Leu Val
            165                 170                 175

Phe Phe Phe Leu Thr Val Phe Phe Leu Pro Glu Ser Pro Arg Trp Leu
            180                 185                 190

Val Ser Lys Gly Arg Met Leu Glu Ala Lys Arg Val Leu Gln Arg Leu
            195                 200                 205

Arg Gly Arg Glu Asp Val Ser Gly Glu Met Ala Leu Leu Val Glu Gly
 210                 215                 220

Leu Gly Ile Gly Gly Glu Thr Thr Ile Glu Glu Tyr Ile Ile Gly Pro
225                 230                 235                 240

Ala Asp Glu Val Thr Asp Asp His Asp Ile Ala Val Asp Lys Asp Gln
            245                 250                 255

Ile Lys Leu Tyr Gly Ala Glu Glu Gly Leu Ser Trp Val Ala Arg Pro
            260                 265                 270

Val Lys Gly Gly Ser Thr Met Ser Val Leu Ser Arg His Gly Ser Thr
            275                 280                 285

Met Ser Arg Arg Gln Gly Ser Leu Ile Asp Pro Leu Val Thr Leu Phe
 290                 295                 300

Gly Ser Val His Glu Lys Met Pro Asp Thr Gly Ser Met Arg Ser Ala
305                 310                 315                 320

Leu Phe Pro His Phe Gly Ser Met Phe Ser Val Gly Asn Gln Pro
            325                 330                 335

Arg His Glu Asp Trp Asp Glu Glu Asn Leu Val Gly Glu Gly Glu Asp
            340                 345                 350

Tyr Pro Ser Asp His Gly Asp Asp Ser Glu Asp Leu His Ser Pro
            355                 360                 365

Leu Ile Ser Arg Gln Thr Thr Ser Met Glu Lys Asp Met Pro His Thr
 370                 375                 380

Ala His Gly Thr Leu Ser Thr Phe Arg His Gly Ser Gln Val Gln Gly
385                 390                 395                 400

Ala Gln Gly Glu Gly Ala Gly Ser Met Gly Ile Gly Gly Trp Gln
            405                 410                 415

Val Ala Trp Lys Trp Thr Glu Arg Glu Asp Glu Ser Gly Gln Lys Glu
            420                 425                 430

Glu Gly Phe Pro Gly Ser Arg Arg Gly Ser Ile Val Ser Leu Pro Gly
```

```
                435                 440                 445
Gly Asp Gly Thr Gly Glu Ala Asp Phe Val Gln Ala Ser Ala Leu Val
            450                 455                 460

Ser Gln Pro Ala Leu Tyr Ser Lys Asp Leu Leu Lys Glu His Thr Ile
465                 470                 475                 480

Gly Pro Ala Met Val His Pro Ser Glu Thr Thr Lys Gly Ser Ile Trp
                485                 490                 495

His Asp Leu His Asp Pro Gly Val Lys Arg Ala Leu Val Val Gly Val
            500                 505                 510

Gly Leu Gln Ile Leu Gln Phe Ser Gly Ile Asn Gly Val Leu Tyr
            515                 520                 525

Tyr Thr Pro Gln Ile Leu Glu Gln Ala Gly Val Gly Ile Leu Leu Ser
        530                 535                 540

Asn Met Gly Ile Ser Ser Ser Ala Ser Leu Leu Ile Ser Ala Leu
545                 550                 555                 560

Thr Thr Phe Val Met Leu Pro Ala Ile Ala Val Ala Met Arg Leu Met
                565                 570                 575

Asp Leu Ser Gly Arg Arg Thr Leu Leu Leu Thr Thr Ile Pro Ile Leu
            580                 585                 590

Ile Ala Ser Leu Leu Val Leu Val Ile Ser Asn Leu Val His Met Asn
        595                 600                 605

Ser Ile Val His Ala Val Leu Ser Thr Val Ser Val Val Leu Tyr Phe
    610                 615                 620

Cys Phe Phe Val Met Gly Phe Gly Pro Ala Pro Asn Ile Leu Cys Ser
625                 630                 635                 640

Glu Ile Phe Pro Thr Arg Val Arg Gly Ile Cys Ile Ala Ile Cys Ala
                645                 650                 655

Leu Thr Phe Trp Ile Cys Asp Ile Ile Val Thr Tyr Ser Leu Pro Val
            660                 665                 670

Leu Leu Lys Ser Ile Gly Leu Ala Gly Val Phe Gly Met Tyr Ala Ile
        675                 680                 685

Val Cys Cys Ile Ser Trp Val Phe Val Phe Ile Lys Val Pro Glu Thr
    690                 695                 700

Lys Gly Met Pro Leu Glu Val Ile Thr Glu Phe Phe Ser Val Gly Ala
705                 710                 715                 720

Arg Gln Ala Glu Ala Ala Lys Asn Glu
                725
```

<210> SEQ ID NO 30
<211> LENGTH: 549
<212> TYPE: PRT
<213> ORGANISM: Beta vulgaris

<400> SEQUENCE: 30

```
Met Ser Glu Gly Thr Asn Lys Ala Met Ser Asp Pro Pro Thr Thr
  1               5                  10                  15

Ala Ser Lys Val Ile Ala Asp Phe Asp Pro Leu Lys Pro Pro Lys
                 20                  25                  30

Arg Asn Lys Phe Ala Phe Ala Cys Ala Thr Leu Ala Ser Met Thr Ser
             35                  40                  45

Val Leu Leu Gly Tyr Asp Ile Gly Val Met Ser Gly Ala Ile Ile Tyr
         50                  55                  60

Leu Lys Glu Asp Trp His Ile Ser Asp Thr Gln Ile Gly Val Leu Val
 65                  70                  75                  80
```

-continued

```
Gly Ile Leu Asn Ile Tyr Cys Leu Phe Gly Ser Phe Ala Ala Gly Arg
                 85                  90                  95

Thr Ser Asp Trp Ile Gly Arg Arg Tyr Thr Ile Val Leu Ala Gly Ala
            100                 105                 110

Ile Phe Phe Val Gly Ala Leu Leu Met Gly Phe Ala Thr Asn Tyr Ala
        115                 120                 125

Phe Leu Met Val Gly Arg Phe Val Thr Gly Ile Gly Val Gly Tyr Ala
    130                 135                 140

Leu Met Ile Ala Pro Val Tyr Thr Ala Glu Val Ser Pro Ala Ser Ser
145                 150                 155                 160

Arg Gly Phe Leu Thr Ser Phe Pro Glu Val Phe Ile Asn Ala Gly Ile
                165                 170                 175

Leu Leu Gly Tyr Ile Ser Asn Leu Ala Phe Ser Ser Leu Pro Thr His
            180                 185                 190

Leu Ser Trp Arg Phe Met Leu Gly Ile Gly Ala Ile Pro Ser Ile Phe
        195                 200                 205

Leu Ala Ile Gly Val Leu Ala Met Pro Glu Ser Pro Arg Trp Leu Val
    210                 215                 220

Met Gln Gly Arg Leu Gly Asp Ala Lys Lys Val Leu Asn Arg Ile Ser
225                 230                 235                 240

Asp Ser Pro Glu Glu Ala Gln Leu Arg Leu Ser Glu Ile Lys Gln Thr
                245                 250                 255

Ala Gly Ile Pro Ala Glu Cys Asp Glu Asp Ile Tyr Lys Val Glu Lys
            260                 265                 270

Thr Lys Ile Lys Ser Gly Asn Ala Val Trp Lys Glu Leu Phe Phe Asn
        275                 280                 285

Pro Thr Pro Ala Val Arg Arg Ala Val Ile Ala Gly Ile Gly Ile His
    290                 295                 300

Phe Phe Gln Gln Ala Ser Gly Ile Asp Ala Val Val Leu Tyr Ser Pro
305                 310                 315                 320

Arg Ile Phe Gln Ser Ala Gly Ile Thr Asn Ala Arg Lys Gln Leu Leu
                325                 330                 335

Ala Thr Val Ala Val Gly Val Val Lys Thr Leu Phe Ile Leu Val Ala
            340                 345                 350

Thr Phe Gln Leu Asp Lys Tyr Gly Arg Arg Pro Leu Leu Leu Thr Ser
        355                 360                 365

Val Gly Gly Met Ile Ile Ala Ile Leu Thr Leu Ala Met Ser Leu Thr
    370                 375                 380

Val Ile Asp His Ser His His Lys Ile Thr Trp Ala Ile Ala Leu Cys
385                 390                 395                 400

Ile Thr Met Val Cys Ala Val Val Ala Ser Phe Ser Ile Gly Leu Gly
                405                 410                 415

Pro Ile Thr Trp Val Tyr Ser Ser Glu Val Phe Pro Leu Arg Leu Arg
            420                 425                 430

Ala Gln Gly Thr Ser Met Gly Val Ala Val Asn Arg Val Val Ser Gly
        435                 440                 445

Val Ile Ser Ile Phe Phe Leu Pro Leu Ser His Lys Ile Thr Thr Gly
    450                 455                 460

Gly Ala Phe Phe Leu Phe Gly Ile Ala Ile Ala Trp Phe Phe
465                 470                 475                 480

Phe Leu Thr Phe Leu Pro Glu Thr Arg Gly Arg Thr Leu Glu Asn Met
                485                 490                 495

His Glu Leu Phe Glu Asp Phe Arg Trp Arg Glu Ser Phe Pro Gly Asn
```

```
                500               505               510
Lys Ser Asn Asn Asp Glu Asn Ser Thr Arg Lys Gln Ser Asn Gly Asn
            515                   520                   525

Asp Lys Ser Gln Val Gln Leu Gly Glu Thr Thr Thr Ser Thr Thr Val
        530                   535                   540

Thr Asn Asp Asn His
545

<210> SEQ ID NO 31
<211> LENGTH: 2777
<212> TYPE: DNA
<213> ORGANISM: Zea mays

<400> SEQUENCE: 31
```

| | | | | | |
|---|---|---|---|---|---|
| cacggggtta | gattcggagc | ggctcttggc | ttgcagtcca | aacgcccttc | acccctgatc | 60 |
| tggaccggag | ggagcggctc | cttccgtcag | ttgttcttgc | tttgcctggg | cctcttccgc | 120 |
| ctgcttcgtg | ttcttcacag | gagccggtga | cctcggacga | tatcttggag | gacaagatgt | 180 |
| cgggggctgt | tcttgtcgcc | atagtcgcct | ccatcggcaa | tctattgcag | ggtgggaca | 240 |
| atgccaccat | cgcagctgct | gttctgtata | taaagaagga | atttcaattg | caaaatgagc | 300 |
| ccactgtgga | gggactaatt | gtgtcaatgt | cacttatcgg | cgccaccatc | gttactacat | 360 |
| tctccgggcc | attatcagac | tcgattggcc | gacgccctat | gcttattctc | tcttcaattc | 420 |
| tgtacttctt | cagcggcctc | atcatgctat | ggtctcctaa | tgtctatgtc | ctgctgttgg | 480 |
| cacgcttcgt | agatggattt | ggtattggct | ggctgtcac | gcttgtgcct | ttgtacattt | 540 |
| cagaaatagc | cccttcggag | attagaggtt | tgctgaatac | actaccacaa | ttcagtggat | 600 |
| caggaggaat | gttcttgtca | tactgcatgg | tgtttgggat | gtccctgtcg | ccatcacccg | 660 |
| attggagaat | tatgcttggt | gtgctcgcga | taccttcatt | gttcttcttt | ggtttgacaa | 720 |
| tattttatct | tcctgaatct | ccaagatggc | tcgttagcaa | aggtcggatg | gcagaggcaa | 780 |
| aaaaggtgtt | gcaaaagtta | cgggggaaag | acgatgtctc | aggtgaattg | tcccttcttc | 840 |
| tcgaagggtt | ggaggttgga | ggagacactt | ccattgaaga | gtacatcatt | ggacctgcca | 900 |
| ccgaggcagc | cgatgatctt | gttactgacg | gtgataagga | acaaatcaca | ctttatgggc | 960 |
| ctgaagaagg | ccagtcatgg | attgctcgac | cttctaaggg | acccatcatg | cttggaagtg | 1020 |
| tgctttctct | tgcatctcgt | catgggagca | tggtgaacca | gagtgtaccc | cttatggatc | 1080 |
| cgattgtgac | acttttggt | agtgtccatg | agaatatgcc | tcaagctgga | ggaagtatga | 1140 |
| ggagcacatt | gtttccaaac | tttggaagta | tgttcagtgt | cacagatcag | catgccaaaa | 1200 |
| atgagcagtg | ggatgaagag | aatcttcata | gggatgacga | ggagtacgca | tctgatggtg | 1260 |
| caggaggtga | ctatgaggac | aatctccata | gcccattgct | gtccaggcag | gcaacaggtg | 1320 |
| cggaagggaa | ggacattgtg | caccatggtc | accgtggaag | tgctttgagc | atgagaaggc | 1380 |
| aaaccctctt | aggggagggt | ggagatggtg | tgagcagcac | tgatatcggt | ggggatggc | 1440 |
| agcttgcttg | gaaatggtca | gagaaggaag | gtgagaatgg | tagaaaggaa | ggtggtttca | 1500 |
| aaagagtcta | cttgcaccaa | gagggagttc | ctggctcaag | aaggggctca | attgtttcac | 1560 |
| ttcccgtgg | tggcgatgtt | tttgaggta | gtgagtttgt | acatgctgct | gctttagtaa | 1620 |
| gtcagtcagc | acttttctca | aagggtcttg | ctgaaccacg | catgtcagat | gctgccatgg | 1680 |
| ttcacccatc | tgaggtagct | gccaaaggtt | cacgttggaa | agatttgttt | gaacctggag | 1740 |
| tgaggcgtgc | cctgttagtc | ggtgttggaa | ttcagatcct | tcaacagttt | gctggaataa | 1800 |

-continued

```
acggtgttct gtactatacc ccacaaattc ttgagcaagc tggtgtggca gttattcttt    1860
ccaaatttgg tctcagctcg gcatcagcat ccatcttgat cagttctctc actaccttac    1920
taatgcttcc ttgcattggc tttgccatgc tgcttatgga tctttccgga agaaggtttt    1980
tgctgctagg cacaattcca atcttgatag catctctagt tatcctggtt gtgtccaatc    2040
taattgattt gggtacacta gcccatgctt tgctctccac cgtcagtgtt atcgtctact    2100
tctgctgctt cgttatggga tttggtccca tccccaacat tttatgtgca gagatctttc    2160
caaccagggt tcgtggcctc tgtattgcca tttgtgcctt acattctgg atcggagata     2220 tcatcgtcac ctacagcctt cctgtgatgc tgaatgctat tggactggcg ggtgttttca    2280
gcatatatgc agtcgtatgc ttgatttcct ttgtgttcgt cttccttaag gtccctgaga    2340 caaagggat gcccttgag gttattaccg aattctttgc agttggtgcg aagcaagcgg      2400
ctgcaaaagc ctaatttctt tggtaccttt gtgtgcaact attgcactgt aagttagaaa    2460
cttgaagggg tttcaccaag aagctcggag aattactttg gatttgtgta aatgttaagg    2520
gaacgaacat ctgctcatgc tcctcaaacg gtaaaaaaga gtccctcaat ggcaaatagg    2580
agtcgttaag ttgtcaatgt catttaccat atgttttacc tatttgtact gtattataag    2640
tcaagctatt caacgctggt tgttgctaga aatctttaga acaaagatga taatgatctg    2700
atctgatgtt ataatattca aatctcaaat aaagaaaata tcgtttctca aaaaaaaaa     2760 aaaaaaaaaa aaaaaaa                                                    2777
```

<210> SEQ ID NO 32
<211> LENGTH: 800
<212> TYPE: PRT
<213> ORGANISM: Zea mays

<400> SEQUENCE: 32

```
Ile Arg Ser Gly Ser Trp Leu Ala Val Gln Thr Pro Phe Thr Pro Asp
  1               5                  10                  15

Leu Asp Arg Arg Glu Arg Leu Leu Pro Ser Val Val Leu Ala Leu Pro
             20                  25                  30

Gly Pro Leu Pro Pro Ala Ser Cys Ser Ser Gln Glu Pro Val Thr Ser
         35                  40                  45

Asp Asp Ile Leu Glu Asp Lys Met Ser Gly Ala Val Leu Val Ala Ile
     50                  55                  60

Val Ala Ser Ile Gly Asn Leu Leu Gln Gly Trp Asp Asn Ala Thr Ile
 65                  70                  75                  80

Ala Ala Ala Val Leu Tyr Ile Lys Lys Glu Phe Gln Leu Gln Asn Glu
                 85                  90                  95

Pro Thr Val Glu Gly Leu Ile Val Ser Met Ser Leu Ile Gly Ala Thr
            100                 105                 110

Ile Val Thr Thr Phe Ser Gly Pro Leu Ser Asp Ser Ile Gly Arg Arg
        115                 120                 125

Pro Met Leu Ile Leu Ser Ser Ile Leu Tyr Phe Phe Ser Gly Leu Ile
    130                 135                 140

Met Leu Trp Ser Pro Asn Val Tyr Val Leu Leu Ala Arg Phe Val
145                 150                 155                 160

Asp Gly Phe Gly Ile Gly Leu Ala Val Thr Leu Val Pro Leu Tyr Ile
                165                 170                 175

Ser Glu Ile Ala Pro Ser Glu Ile Arg Gly Leu Leu Asn Thr Leu Pro
            180                 185                 190

Gln Phe Ser Gly Ser Gly Gly Met Phe Leu Ser Tyr Cys Met Val Phe
```

-continued

```
            195                 200                 205
Gly Met Ser Leu Ser Pro Ser Pro Asp Trp Arg Ile Met Leu Gly Val
            210                 215                 220
Leu Ala Ile Pro Ser Leu Phe Phe Phe Gly Leu Thr Ile Phe Tyr Leu
225                 230                 235                 240
Pro Glu Ser Pro Arg Trp Leu Val Ser Lys Gly Arg Met Ala Glu Ala
                    245                 250                 255
Lys Lys Val Leu Gln Lys Leu Arg Gly Lys Asp Val Ser Gly Glu
                260                 265                 270
Leu Ser Leu Leu Glu Gly Leu Glu Val Gly Gly Asp Thr Ser Ile
            275                 280                 285
Glu Glu Tyr Ile Ile Gly Pro Ala Thr Glu Ala Ala Asp Asp Leu Val
290                 295                 300
Thr Asp Gly Asp Lys Glu Gln Ile Thr Leu Tyr Gly Pro Glu Glu Gly
305                 310                 315                 320
Gln Ser Trp Ile Ala Arg Pro Ser Lys Gly Pro Ile Met Leu Gly Ser
                325                 330                 335
Val Leu Ser Leu Ala Ser Arg His Gly Ser Met Val Asn Gln Ser Val
                340                 345                 350
Pro Leu Met Asp Pro Ile Val Thr Leu Phe Gly Ser Val His Glu Asn
                355                 360                 365
Met Pro Gln Ala Gly Gly Ser Met Arg Ser Thr Leu Phe Pro Asn Phe
            370                 375                 380
Gly Ser Met Phe Ser Val Thr Asp Gln His Ala Lys Asn Glu Gln Trp
385                 390                 395                 400
Asp Glu Glu Asn Leu His Arg Asp Asp Glu Glu Tyr Ala Ser Asp Gly
                405                 410                 415
Ala Gly Gly Asp Tyr Glu Asp Asn Leu His Ser Pro Leu Leu Ser Arg
                420                 425                 430
Gln Ala Thr Gly Ala Glu Gly Lys Asp Ile Val His His Gly His Arg
                435                 440                 445
Gly Ser Ala Leu Ser Met Arg Arg Gln Thr Leu Leu Gly Glu Gly Gly
450                 455                 460
Asp Gly Val Ser Ser Thr Asp Ile Gly Gly Gly Trp Gln Leu Ala Trp
465                 470                 475                 480
Lys Trp Ser Glu Lys Glu Gly Glu Asn Gly Arg Lys Glu Gly Gly Phe
                485                 490                 495
Lys Arg Val Tyr Leu His Gln Glu Gly Val Pro Gly Ser Arg Arg Gly
                500                 505                 510
Ser Ile Val Ser Leu Pro Gly Gly Gly Asp Val Phe Glu Gly Ser Glu
                515                 520                 525
Phe Val His Ala Ala Ala Leu Val Ser Gln Ser Ala Leu Phe Ser Lys
                530                 535                 540
Gly Leu Ala Glu Pro Arg Met Ser Asp Ala Ala Met Val His Pro Ser
545                 550                 555                 560
Glu Val Ala Ala Lys Gly Ser Arg Trp Lys Asp Leu Phe Glu Pro Gly
                565                 570                 575
Val Arg Arg Ala Leu Leu Val Gly Val Gly Ile Gln Ile Leu Gln Gln
                580                 585                 590
Phe Ala Gly Ile Asn Gly Val Leu Tyr Tyr Thr Pro Gln Ile Leu Glu
            595                 600                 605
Gln Ala Gly Val Ala Val Ile Leu Ser Lys Phe Gly Leu Ser Ser Ala
            610                 615                 620
```

```
Ser Ala Ser Ile Leu Ile Ser Ser Leu Thr Thr Leu Leu Met Leu Pro
625                 630                 635                 640

Cys Ile Gly Phe Ala Met Leu Leu Met Asp Leu Ser Gly Arg Arg Phe
            645                 650                 655

Leu Leu Leu Gly Thr Ile Pro Ile Leu Ile Ala Ser Leu Val Ile Leu
            660                 665                 670

Val Val Ser Asn Leu Ile Asp Leu Gly Thr Leu Ala His Ala Leu Leu
            675                 680                 685

Ser Thr Val Ser Val Ile Val Tyr Phe Cys Cys Phe Val Met Gly Phe
690                 695                 700

Gly Pro Ile Pro Asn Ile Leu Cys Ala Glu Ile Phe Pro Thr Arg Val
705                 710                 715                 720

Arg Gly Leu Cys Ile Ala Ile Cys Ala Phe Thr Phe Trp Ile Gly Asp
            725                 730                 735

Ile Ile Val Thr Tyr Ser Leu Pro Val Met Leu Asn Ala Ile Gly Leu
            740                 745                 750

Ala Gly Val Phe Ser Ile Tyr Ala Val Val Cys Leu Ile Ser Phe Val
            755                 760                 765

Phe Val Phe Leu Lys Val Pro Glu Thr Lys Gly Met Pro Leu Glu Val
770                 775                 780

Ile Thr Glu Phe Phe Ala Val Gly Ala Lys Gln Ala Ala Ala Lys Ala
785                 790                 795                 800

<210> SEQ ID NO 33
<211> LENGTH: 2063
<212> TYPE: DNA
<213> ORGANISM: Zea mays

<400> SEQUENCE: 33
gtgttgtaag cctactaaaa tttgctgtta ttgattttg gaccctttca tttcatcagg      60
tgcacgcgtc gatgtcgttg ccagcacgga acaatcacca ccgttattaa gaagatgatg     120
cgctgcgctg caacgggcgg cgggtgcgtc gcttcgtgga gcggcgatcg gagattgccg     180
gcggtcaacc cctgcagcgt gcggatgccg acgggcaacg atgggtggtg cgccggcctg     240
aggtcgcggg cggcggatct cgccggcctc gagatggcca acctgcgcgg cggcgtcggg     300
gggctcttcc gcgcgagccc gcgctacggg cgcttgcaag ccacggcggc agttgaccct     360
gaagatattc cattggagaa ggttcaagtt aaatcctcag acatgttct gccatatgtt      420 ggcgttgctt gttttgggggc tattctgttt ggttaccatc ttggtgtggt caatggcgca     480
cttgaatatc tcgcgaagga tcttgggatt gctgaaaatg ctgtcttgca ggggtgggtg     540
gttagcacat ccttggctgg tgcaacacta ggttcttta ctgggggttc tttggcagat       600
aaatttgggc ggacaagaac attcatcctg gatgcagtcc cacttgctct aggtgcattc     660
ttgagtgcaa cagctcaaga tatccgcaca atgattattg ccgattgct tgctggaatt       720 ggtatcgggg tctcatctgc tcttgtaccc ctttacatat ctgagatctc accaactgaa      780
attcgtggaa cacttggtac cgttaatcaa ctttttattt gcattggaat tcttgcagct     840
ttgttagctg gattgcctct ggcaggaaat cctgcctggt ggaggacaat gtttggaatt      900
gctgtagttc catccattct gctggctgta ggaatggcct tttcgcctga aagccctcgt      960
tggctattcc agcaaggaaa ggttactcaa gcagaattag ctgtaaaaag actgtatgga     1020
aaagaaatgg ttaccgaaat tatgtttgat ctgagagcta gtggccaaag ttcttcggag     1080
tccgaagccg gctggtttga tcttttcagc aagcgttact ggaaagttgt gagtgtgggg     1140
```

```
gcagcactgt ttttgttcca gcagcttgct ggtataaacg ctgttgtata ttactctaca    1200
tcggtgttcc gtagtgcagg cattgcatct gatgttgctg ctagtgctct tgttggagca    1260
gccaatgttt ttggtactat ggttgcatct tctctaatgg acaaacaagg aaggaaaagc    1320
cttctgataa caagcttttc tggaatgggt gcttcaatgc tactcctagc attgtccttc    1380
acctggaaag ctctggcacc ttattctggt actcttgctg ttgttggcac tgttctgtac    1440
gtgctgtcat ttgctctagg agcgggccct gttccagcgc tacttcttcc tgaaatattt    1500
gcctcgagaa taagggccaa ggctgtcgca ttatctctag gcatgcactg ggtatctaac    1560
tttttcattg gcctgtactt cctgagtgtc gtgagcaagt ttgggatcag caacgtgtat    1620
ctgggatttg catcagtatg tgccttgca gttctgtaca tagctgggaa tgtggtcgag    1680
accaagggga gatcacttga agagattgaa agggagctaa gtgtagcaga atgatgtact    1740
tttgctagtc atgctgtggc gccgttttgg ttatcgagaa tgcaaccaag cgctcaaccg    1800
agcatccttg gacctggaga ctctttctag tttcatgtag ttttagaaat aagcgaacgg    1860
caagagtacc aatcttaggt gacttggtgt gggttgtgtc tgaaataagt gaattggatt    1920
gtagaatttc agaaataagt gaattggatt gtagaatttc aaaaagtgtg ttccccttaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaa                                            2063

<210> SEQ ID NO 34
<211> LENGTH: 571
<212> TYPE: PRT
<213> ORGANISM: Zea mays

<400> SEQUENCE: 34

Asn Leu Leu Leu Ile Phe Gly Pro Phe His Phe Ile Arg Cys Thr
  1               5                  10                  15

Arg Arg Cys Arg Cys Gln His Gly Thr Ile Thr Val Ile Lys Lys
                 20                  25                  30

Met Met Arg Cys Ala Ala Thr Gly Gly Gly Cys Val Ala Ser Trp Ser
             35                  40                  45

Gly Asp Arg Arg Leu Pro Ala Val Asn Pro Cys Ser Val Arg Met Pro
         50                  55                  60

Thr Gly Asn Asp Gly Trp Cys Ala Gly Leu Arg Ser Arg Ala Ala Asp
 65                  70                  75                  80

Leu Ala Gly Leu Glu Met Ala Asn Leu Arg Gly Val Gly Gly Leu
                 85                  90                  95

Phe Arg Ala Ser Pro Arg Tyr Gly Arg Leu Gln Ala Thr Ala Ala Val
            100                 105                 110

Asp Pro Glu Asp Ile Pro Leu Glu Lys Val Gln Val Lys Ser Ser Gly
        115                 120                 125

His Val Leu Pro Tyr Val Gly Val Ala Cys Leu Gly Ala Ile Leu Phe
    130                 135                 140

Gly Tyr His Leu Gly Val Val Asn Gly Ala Leu Glu Tyr Leu Ala Lys
145                 150                 155                 160

Asp Leu Gly Ile Ala Glu Asn Ala Val Leu Gln Gly Trp Val Ser
                165                 170                 175

Thr Ser Leu Ala Gly Ala Thr Leu Gly Ser Phe Thr Gly Gly Ser Leu
            180                 185                 190

Ala Asp Lys Phe Gly Arg Thr Arg Thr Phe Ile Leu Asp Ala Val Pro
        195                 200                 205
```

-continued

```
Leu Ala Leu Gly Ala Phe Leu Ser Ala Thr Ala Gln Asp Ile Arg Thr
        210                 215                 220
Met Ile Ile Gly Arg Leu Leu Ala Gly Ile Gly Ile Gly Val Ser Ser
225                 230                 235                 240
Ala Leu Val Pro Leu Tyr Ile Ser Glu Ile Ser Pro Thr Glu Ile Arg
                245                 250                 255
Gly Thr Leu Gly Thr Val Asn Gln Leu Phe Ile Cys Ile Gly Ile Leu
            260                 265                 270
Ala Ala Leu Leu Ala Gly Leu Pro Leu Ala Gly Asn Pro Ala Trp Trp
        275                 280                 285
Arg Thr Met Phe Gly Ile Ala Val Val Pro Ser Ile Leu Leu Ala Val
290                 295                 300
Gly Met Ala Phe Ser Pro Glu Ser Pro Arg Trp Leu Phe Gln Gln Gly
305                 310                 315                 320
Lys Val Thr Gln Ala Glu Leu Ala Val Lys Arg Leu Tyr Gly Lys Glu
                325                 330                 335
Met Val Thr Glu Ile Met Phe Asp Leu Arg Ala Ser Gly Gln Ser Ser
            340                 345                 350
Ser Glu Ser Glu Ala Gly Trp Phe Asp Leu Phe Ser Lys Arg Tyr Trp
        355                 360                 365
Lys Val Val Ser Val Gly Ala Ala Leu Phe Leu Phe Gln Gln Leu Ala
370                 375                 380
Gly Ile Asn Ala Val Val Tyr Tyr Ser Thr Ser Val Phe Arg Ser Ala
385                 390                 395                 400
Gly Ile Ala Ser Asp Val Ala Ala Ser Ala Leu Val Gly Ala Ala Asn
                405                 410                 415
Val Phe Gly Thr Met Val Ala Ser Ser Leu Met Asp Lys Gln Gly Arg
            420                 425                 430
Lys Ser Leu Leu Ile Thr Ser Phe Ser Gly Met Gly Ala Ser Met Leu
        435                 440                 445
Leu Leu Ala Leu Ser Phe Thr Trp Lys Ala Leu Ala Pro Tyr Ser Gly
450                 455                 460
Thr Leu Ala Val Val Gly Thr Val Leu Tyr Val Leu Ser Phe Ala Leu
465                 470                 475                 480
Gly Ala Gly Pro Val Pro Ala Leu Leu Leu Pro Glu Ile Phe Ala Ser
                485                 490                 495
Arg Ile Arg Ala Lys Ala Val Ala Leu Ser Leu Gly Met His Trp Val
            500                 505                 510
Ser Asn Phe Phe Ile Gly Leu Tyr Phe Leu Ser Val Val Ser Lys Phe
        515                 520                 525
Gly Ile Ser Asn Val Tyr Leu Gly Phe Ala Ser Val Cys Ala Leu Ala
530                 535                 540
Val Leu Tyr Ile Ala Gly Asn Val Val Glu Thr Lys Gly Arg Ser Leu
545                 550                 555                 560
Glu Glu Ile Glu Arg Glu Leu Ser Val Ala Glu
                565                 570

<210> SEQ ID NO 35
<211> LENGTH: 1953
<212> TYPE: DNA
<213> ORGANISM: Zea mays
<220> FEATURE:
<221> NAME/KEY: unsure
<222> LOCATION: (1584)
<223> OTHER INFORMATION: n = A, C, G or T
```

<400> SEQUENCE: 35

```
ccttcctcct cgtcctcctt caggccagcg ggcaagaaga agaagaagaa aaatcaaggc    60
ttgcggcgag aggctgtgcc cggccgaccg gcgagcgagc ttcgtacgcg cgtcatgggt   120
ggcggcagca acagaggcgg cgccggcgcc ggcgaggaga gcggcagcga ccacgacggt   180
gtgctgcgga ggccgctgct caacacgggg agctggtacc ggatgagctc gcggcagtcc   240
agctttgccc cggggacctc ctccatggcc gtcctgcgcg agtcccacgt ctccgccttc   300
ctctgcacgc tcatcgtcgc gctcggcccc atccagttcg gcttcaccag cggcttctcc   360
tccccgaccc aggacgccat ggttcgggac ctcaacctct ctatctccga gttctcggcg   420
ttcggatcgc tgtccaacgt cggcggcatg gtcgggcga tcgccagcgg gcagatggcc   480
gagtacattg ccgtaaagg gtcgttgatg attgctgcaa tcccaaatat catcggttgg   540
cttgcgatct cctttgcaaa agatgcctca tttctatata tgggacgatt gcttgaaggg   600
tttggtgtcg gcatcatatc ctacacgta ccggtataca tagcagagat atctcctcag   660
aacatgaggg gagctcttgg ttctgtgaac cagttgtctg tgacctttgg catattcttg   720
gcctatttgc tcggcatgtt tattccttgg agacttcttg ctgtgattgg agccttgccc   780
tgcacaatgt tgattcctgg actattcttc attccagaat ctcccagatg gctggcaaag   840
atgaatttga cggaagattg tgagacgtcc ctacaagtgc tgaggggtt tgagactgac   900
atcacaacag aagtgaatga tataaagagg gcagtggcat catcaagtaa gaggaccaca   960
atcagttttc aagaattaaa ccaaaagaaa taccgcacgc cactacttct agggattggc  1020
ctacttgtac tgcaaaatct tagtggaatc aacggtgtac tgttttatgc aagtagcatc  1080
ttcaaagctg caggggttac aaacagcgac ttggccacct gttcacttgg tgctattcag  1140
gtccttgcta ctggagttac aacatggctg ttagaccgag ctggacgacg catccttctc  1200
attatttcta cctctggcat gactctatgc cttcttgccg tttctgttgt attttttctc  1260
aaggataaca tttcacagga ttctaactca tactacatct taacaatgat ctcccttgtt  1320
ggtattgtgt cttttgtcat taccttctcg ttttggtatgg gtgccattcc atggctcatg  1380
atgtctgaga tcctcccggt tagcatcaag agccttggcg gaagcatcgc aacactggcc  1440
aactggctga catccttcgc cataacaatg acgacgaact tgatgctcac gtggagtgtt  1500
ggaggcactt ttctctcgta catggttgtg agcgccttca ccatcgtttt tgttgtcctt  1560
tgggtgccgg agacgaaggg gagnaactct agaggagata caattttcgt ttcgctgagc  1620
attcagcgtc agctgcaatg gttgcccgag tgtttatctt agggcctgtt tcgatcccat  1680
gagctaaagc aaaagaagc taaaatttag tcactttata aactaaagtt ccaatcagga  1740
ggagctaaaa gtgaataaaa tagcaaaaga atatctttta gtcactttta gcttctaaag  1800
aggagctaga atttagtccc ttgttttagc ttatactcct tccatcctaa aaaaatatag  1860
gtctttctaa ctttttcttt ttctgttcat attcattcga ataatgataa atatagacat  1920
acgtataaac tattcattaa aaaaaaaaaa aaa                                1953
```

<210> SEQ ID NO 36
<211> LENGTH: 553
<212> TYPE: PRT
<213> ORGANISM: Zea mays
<220> FEATURE:
<221> NAME/KEY: UNSURE
<222> LOCATION: (528)
<223> OTHER INFORMATION: Xaa = ANY AMINO ACID -continued

```
<400> SEQUENCE: 36

Pro Ser Ser Ser Ser Phe Arg Pro Ala Gly Lys Lys Lys Lys
 1               5                  10                  15

Lys Asn Gln Gly Leu Arg Arg Glu Ala Val Pro Gly Arg Pro Ala Ser
            20                  25                  30

Glu Leu Arg Thr Arg Val Met Gly Gly Ser Asn Arg Gly Gly Ala
         35                  40                  45

Gly Ala Gly Glu Glu Ser Gly Ser Asp His Asp Gly Val Leu Arg Arg
 50                  55                  60

Pro Leu Leu Asn Thr Gly Ser Trp Tyr Arg Met Ser Ser Arg Gln Ser
 65                  70                  75                  80

Ser Phe Ala Pro Gly Thr Ser Met Ala Val Leu Arg Glu Ser His
             85                  90                  95

Val Ser Ala Phe Leu Cys Thr Leu Ile Val Ala Leu Gly Pro Ile Gln
            100                 105                 110

Phe Gly Phe Thr Ser Gly Phe Ser Ser Pro Thr Gln Asp Ala Met Val
            115                 120                 125

Arg Asp Leu Asn Leu Ser Ile Ser Glu Phe Ser Ala Phe Gly Ser Leu
130                 135                 140

Ser Asn Val Gly Gly Met Val Gly Ala Ile Ala Ser Gly Gln Met Ala
145                 150                 155                 160

Glu Tyr Ile Gly Arg Lys Gly Ser Leu Met Ile Ala Ala Ile Pro Asn
                165                 170                 175

Ile Ile Gly Trp Leu Ala Ile Ser Phe Ala Lys Asp Ala Ser Phe Leu
            180                 185                 190

Tyr Met Gly Arg Leu Leu Glu Gly Phe Gly Val Gly Ile Ile Ser Tyr
        195                 200                 205

Thr Val Pro Val Tyr Ile Ala Glu Ile Ser Pro Gln Asn Met Arg Gly
    210                 215                 220

Ala Leu Gly Ser Val Asn Gln Leu Ser Val Thr Phe Gly Ile Phe Leu
225                 230                 235                 240

Ala Tyr Leu Leu Gly Met Phe Ile Pro Trp Arg Leu Leu Ala Val Ile
                245                 250                 255

Gly Ala Leu Pro Cys Thr Met Leu Ile Pro Gly Leu Phe Phe Ile Pro
            260                 265                 270

Glu Ser Pro Arg Trp Leu Ala Lys Met Asn Leu Thr Glu Asp Cys Glu
        275                 280                 285

Thr Ser Leu Gln Val Leu Arg Gly Phe Glu Thr Asp Ile Thr Thr Glu
    290                 295                 300

Val Asn Asp Ile Lys Arg Ala Val Ala Ser Ser Lys Arg Thr Thr
305                 310                 315                 320

Ile Ser Phe Gln Glu Leu Asn Gln Lys Lys Tyr Arg Thr Pro Leu Leu
                325                 330                 335

Leu Gly Ile Gly Leu Val Leu Gln Asn Leu Ser Gly Ile Asn Gly
            340                 345                 350

Val Leu Phe Tyr Ala Ser Ser Ile Phe Lys Ala Ala Gly Val Thr Asn
        355                 360                 365

Ser Asp Leu Ala Thr Cys Ser Leu Gly Ala Ile Gln Val Leu Ala Thr
    370                 375                 380

Gly Val Thr Thr Trp Leu Leu Asp Arg Ala Gly Arg Arg Ile Leu Leu
385                 390                 395                 400

Ile Ile Ser Thr Ser Gly Met Thr Leu Cys Leu Leu Ala Val Ser Val
                405                 410                 415
```

```
Val Phe Phe Leu Lys Asp Asn Ile Ser Gln Asp Ser Asn Ser Tyr Tyr
            420                 425                 430

Ile Leu Thr Met Ile Ser Leu Val Gly Ile Val Ser Phe Val Ile Thr
            435                 440                 445

Phe Ser Phe Gly Met Gly Ala Ile Pro Trp Leu Met Met Ser Glu Ile
            450                 455                 460

Leu Pro Val Ser Ile Lys Ser Leu Gly Gly Ser Ile Ala Thr Leu Ala
465                 470                 475                 480

Asn Trp Leu Thr Ser Phe Ala Ile Thr Met Thr Thr Asn Leu Met Leu
            485                 490                 495

Thr Trp Ser Val Gly Gly Thr Phe Leu Ser Tyr Met Val Val Ser Ala
            500                 505                 510

Phe Thr Ile Val Phe Val Leu Trp Val Pro Glu Thr Lys Gly Xaa
            515                 520                 525

Asn Ser Arg Gly Asp Thr Ile Phe Val Ser Leu Ser Ile Gln Arg Gln
            530                 535                 540

Leu Gln Trp Leu Pro Glu Cys Leu Ser
545                 550

<210> SEQ ID NO 37
<211> LENGTH: 740
<212> TYPE: PRT
<213> ORGANISM: Oryza sativa

<400> SEQUENCE: 37

Met Ala Gly Ala Val Leu Val Ala Ile Ala Ala Ser Ile Gly Asn Leu
  1               5                  10                  15

Leu Gln Gly Trp Asp Asn Ala Thr Ile Ala Gly Ala Val Leu Tyr Ile
             20                  25                  30

Lys Lys Glu Phe Asn Leu Gln Ser Glu Pro Leu Ile Glu Gly Leu Ile
         35                  40                  45

Val Ala Met Ser Leu Ile Gly Ala Thr Ile Ile Thr Thr Phe Ser Gly
     50                  55                  60

Ala Val Ala Asp Ser Phe Gly Arg Arg Pro Met Leu Ile Ala Ser Ala
 65                  70                  75                  80

Val Leu Tyr Phe Val Ser Gly Leu Val Met Leu Trp Ala Pro Asn Val
                 85                  90                  95

Tyr Val Leu Leu Leu Ala Arg Leu Ile Asp Gly Phe Gly Ile Gly Leu
            100                 105                 110

Ala Val Thr Leu Val Pro Leu Tyr Ile Ser Glu Thr Ala Pro Thr Asp
            115                 120                 125

Ile Arg Gly Leu Leu Asn Thr Leu Pro Gln Phe Ser Gly Ser Gly Gly
        130                 135                 140

Met Phe Leu Ser Tyr Cys Met Val Phe Gly Met Ser Leu Met Pro Gln
145                 150                 155                 160

Pro Asp Trp Arg Ile Met Leu Gly Val Leu Ser Ile Pro Ser Leu Ile
            165                 170                 175

Tyr Phe Ala Leu Thr Ile Phe Tyr Leu Pro Glu Ser Pro Arg Trp Leu
            180                 185                 190

Val Ser Lys Gly Arg Met Ala Glu Ala Lys Arg Val Leu Gln Gly Leu
        195                 200                 205

Arg Gly Arg Glu Asp Val Ser Gly Glu Met Ala Leu Leu Val Glu Gly
    210                 215                 220

Leu Gly Val Gly Lys Asp Thr Lys Ile Glu Glu Tyr Ile Ile Gly Pro
```

```
             225                 230                 235                 240
Asp Asp Glu Leu Ala Asp Glu Gly Leu Ala Pro Asp Pro Glu Lys Ile
                245                 250                 255
Lys Leu Tyr Gly Pro Glu Glu Gly Leu Ser Trp Val Ala Arg Pro Val
                260                 265                 270
His Gly Gln Ser Ala Leu Gly Ser Ala Leu Gly Leu Ile Ser Arg His
                275                 280                 285
Gly Ser Met Val Ser Gln Gly Lys Pro Leu Val Asp Pro Val Val Thr
                290                 295                 300
Leu Phe Gly Ser Val His Glu Lys Met Pro Glu Ile Met Gly Ser Met
305                 310                 315                 320
Arg Ser Thr Leu Phe Pro Asn Phe Gly Ser Met Phe Ser Val Ala Glu
                325                 330                 335
Gln Gln Gln Ala Lys Gly Asp Trp Asp Ala Glu Ser Gln Arg Glu Gly
                340                 345                 350
Glu Asp Tyr Gly Ser Asp His Gly Gly Asp Asp Ile Glu Asp Ser Leu
                355                 360                 365
Gln Ser Pro Leu Ile Ser Arg Gln Ala Thr Ser Val Glu Gly Lys Glu
                370                 375                 380
Ile Ala Ala Pro His Gly Ser Ile Met Gly Ala Val Gly Arg Ser Ser
385                 390                 395                 400
Ser Leu Met Gln Gly Gly Glu Ala Val Ser Ser Met Gly Ile Gly Gly
                405                 410                 415
Gly Trp Gln Leu Ala Trp Lys Trp Thr Glu Arg Glu Gly Ala Asp Gly
                420                 425                 430
Glu Lys Glu Gly Gly Phe Gln Arg Ile Tyr Leu His Glu Glu Gly Val
                435                 440                 445
Thr Gly Asp Arg Arg Gly Ser Ile Leu Ser Leu Pro Gly Gly Asp Val
                450                 455                 460
Pro Pro Gly Gly Glu Phe Val Gln Ala Ala Leu Val Ser Gln Pro
465                 470                 475                 480
Ala Leu Tyr Ser Lys Glu Leu Met Glu Gln Arg Leu Ala Gly Pro Ala
                485                 490                 495
Met Val His Pro Ser Gln Ala Val Ala Lys Gly Pro Lys Trp Ala Asp
                500                 505                 510
Leu Phe Glu Pro Gly Val Lys His Ala Leu Phe Val Gly Ile Gly Ile
                515                 520                 525
Gln Ile Leu Gln Gln Phe Ala Gly Ile Asn Gly Val Leu Tyr Tyr Thr
                530                 535                 540
Pro Gln Ile Leu Glu Gln Ala Gly Val Gly Val Leu Ala Asn Ile
545                 550                 555                 560
Gly Leu Ser Ser Ser Ala Ser Ile Leu Ile Ser Gly Leu Thr Thr
                565                 570                 575
Leu Leu Met Leu Pro Ser Ile Gly Ile Ala Met Arg Leu Met Asp Met
                580                 585                 590
Ser Gly Arg Arg Phe Leu Leu Leu Ala Thr Ile Pro Ile Leu Ile Val
                595                 600                 605
Ala Leu Ala Ile Leu Ile Leu Val Asn Ile Leu Asp Val Gly Thr Met
                610                 615                 620
Val His Ala Ser Leu Ser Thr Val Ser Val Ile Leu Tyr Phe Cys Phe
625                 630                 635                 640
Phe Val Met Gly Phe Gly Pro Ile Pro Asn Ile Leu Cys Ala Glu Ile
                645                 650                 655
```

```
Phe Pro Thr Thr Val Arg Gly Ile Cys Ile Ala Ile Cys Ala Leu Thr
            660                 665                 670

Phe Trp Ile Gly Asp Ile Ile Val Thr Tyr Thr Leu Pro Val Met Leu
        675                 680                 685

Asn Ala Ile Gly Leu Ala Gly Val Phe Gly Ile Tyr Ala Val Val Cys
        690                 695                 700

Ile Leu Ala Phe Leu Phe Val Phe Met Lys Val Pro Glu Thr Lys Gly
705                 710                 715                 720

Met Pro Leu Glu Val Ile Thr Glu Phe Phe Ser Val Gly Ala Lys Gln
                725                 730                 735

Ala Lys Glu Asp
            740

<210> SEQ ID NO 38
<211> LENGTH: 501
<212> TYPE: PRT
<213> ORGANISM: Oryza sativa

<400> SEQUENCE: 38

Met Ser Phe Arg Gly Glu Glu Ser Gly Gly Asp Gly Gly Arg Thr
1               5                   10                  15

Ala Ser Ala Ser Asp Leu Arg Lys Pro Phe Leu His Thr Gly Ser Trp
            20                  25                  30

Tyr Lys Met Ser Ser Ala Gly Gly Gly Gly Met Gly Ser Arg Leu
        35                  40                  45

Gly Ser Ser Ala Tyr Ser Leu Arg Asp Ser Ser Val Ser Ala Val Leu
    50                  55                  60

Cys Thr Leu Ile Val Ala Leu Gly Pro Ile Gln Phe Gly Phe Thr Cys
65                  70                  75                  80

Gly Phe Ser Ser Pro Thr Gln Asp Ala Ile Ile Ser Asp Leu Gly Leu
                85                  90                  95

Thr Leu Ser Glu Phe Ser Leu Phe Gly Ser Leu Ser Asn Val Gly Ala
            100                 105                 110

Met Val Gly Ala Ile Ala Ser Gly Gln Ile Ala Glu Tyr Ile Gly Arg
        115                 120                 125

Lys Gly Ser Leu Met Ile Ala Ala Ile Pro Asn Ile Ile Gly Trp Leu
    130                 135                 140

Ala Ile Ser Phe Ala Lys Asp Ser Ser Phe Leu Phe Met Gly Arg Leu
145                 150                 155                 160

Leu Glu Gly Phe Gly Val Gly Val Ile Ser Tyr Val Val Pro Val Tyr
                165                 170                 175

Ile Ala Glu Ile Ala Pro Gln Thr Met Arg Gly Ala Leu Gly Ser Val
            180                 185                 190

Asn Gln Leu Ser Val Thr Ile Gly Ile Leu Leu Ala Tyr Leu Leu Gly
        195                 200                 205

Met Phe Val Pro Trp Arg Ile Leu Ser Val Leu Gly Ile Leu Pro Cys
    210                 215                 220

Ser Ile Leu Ile Pro Gly Leu Phe Phe Ile Pro Glu Ser Pro Arg Trp
225                 230                 235                 240

Leu Ala Lys Met Gly Lys Met Glu Asp Phe Glu Ser Ser Leu Gln Val
                245                 250                 255

Leu Arg Gly Phe Glu Thr Asp Ile Ala Val Glu Val Asn Glu Ile Lys
            260                 265                 270

Arg Ser Val Gln Ser Ser Arg Arg Arg Thr Thr Ile Arg Phe Ala Asp
```

-continued

```
            275                 280                 285
Ile Lys Gln Lys Arg Tyr Ser Val Pro Leu Met Val Gly Ile Gly Leu
        290                 295                 300

Leu Val Leu Gln Gln Leu Ser Gly Val Asn Gly Ile Leu Phe Tyr Ala
305                 310                 315                 320

Ala Ser Ile Phe Lys Ala Ala Gly Leu Thr Asn Ser Asn Leu Ala Thr
                325                 330                 335

Phe Gly Leu Gly Val Val Gln Val Val Ala Thr Gly Val Thr Thr Trp
                340                 345                 350

Leu Thr Asp Lys Ala Gly Arg Arg Leu Leu Leu Ile Ile Ser Thr Thr
                355                 360                 365

Gly Met Thr Ile Thr Leu Val Val Val Ser Val Ser Phe Phe Val Lys
        370                 375                 380

Asp Asn Ile Thr Asn Gly Ser His Leu Tyr Ser Val Met Ser Met Leu
385                 390                 395                 400

Ser Leu Val Gly Leu Val Ala Phe Val Ile Ser Phe Ser Leu Gly Leu
                405                 410                 415

Gly Ala Ile Pro Trp Ile Ile Met Ser Glu Ile Leu Pro Val Asn Ile
                420                 425                 430

Lys Ser Leu Ala Gly Ser Val Ala Thr Leu Ala Asn Trp Leu Thr Ala
                435                 440                 445

Trp Leu Ile Thr Met Thr Ala Ser Leu Met Leu Ser Trp Ser Asn Gly
        450                 455                 460

Gly Thr Phe Ala Ile Tyr Ala Ala Val Cys Ala Gly Thr Leu Val Phe
465                 470                 475                 480

Val Cys Leu Trp Val Pro Glu Thr Lys Gly Arg Thr Leu Glu Glu Ile
                485                 490                 495

Ala Phe Ser Phe Arg
                500
```